(12) United States Patent
Suto et al.

(10) Patent No.: US 11,905,258 B2
(45) Date of Patent: *Feb. 20, 2024

(54) 2-AMINOARYL-5-ARYLOXAZOLE ANALOGS FOR THE TREATMENT OF NEURODEGENERATIVE DISEASES

(71) Applicant: Southern Research Institute, Birmingham, AL (US)

(72) Inventors: Mark J. Suto, Homewood, AL (US); Bini Mathew, Hoover, AL (US); Rita Cowell, Hoover, AL (US); Corinne E. Augelli-Szafran, Homewood, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/893,091

(22) Filed: Aug. 22, 2022

(65) Prior Publication Data
US 2023/0002331 A1 Jan. 5, 2023

Related U.S. Application Data

(63) Continuation of application No. 16/968,039, filed as application No. PCT/US2019/018834 on Feb. 20, 2019, now Pat. No. 11,472,781.

(60) Provisional application No. 62/633,577, filed on Feb. 21, 2018.

(51) Int. Cl.
C07D 263/48 (2006.01)
C07D 413/04 (2006.01)

(52) U.S. Cl.
CPC ......... *C07D 263/48* (2013.01); *C07D 413/04* (2013.01)

(58) Field of Classification Search
CPC .......................... C07D 263/48; C07D 413/04
See application file for complete search history.

(56) References Cited

U.S. PATENT DOCUMENTS

| | | | |
|---|---|---|---|
| 8,088,806 | B2 | 1/2012 | Zhang et al. |
| 9,095,596 | B2 | 8/2015 | Grimaldi et al. |
| 2007/0004711 | A1 | 1/2007 | Zhang et al. |
| 2008/0146585 | A1 | 6/2008 | Moussy et al. |
| 2013/0102592 | A1 | 4/2013 | Reader et al. |
| 2014/0179698 | A1 | 6/2014 | Benjahad et al. |
| 2016/0221958 | A1 | 8/2016 | Thiele et al. |
| 2016/0263110 | A1 | 9/2016 | Kinet et al. |

FOREIGN PATENT DOCUMENTS

| | | |
|---|---|---|
| CN | 107625766 | 1/2018 |
| DE | 4126937 | 2/1993 |
| JP | 2002/114768 | 4/2002 |
| JP | 2012/051807 | 3/2012 |
| WO | WO 2000/025780 | 4/2000 |
| WO | Wo 2001/074793 | 10/2001 |
| WO | WO 2003/062215 | 7/2003 |
| WO | WO 2009/105712 | 8/2009 |
| WO | WO 2010/098488 | 9/2010 |
| WO | WO 2011/047129 | 9/2010 |
| WO | WO 2012/170371 | 12/2012 |
| WO | WO 2013/014170 | 1/2013 |
| WO | WO 2019/164996 | 8/2019 |
| WO | WO 2019/222497 | 11/2019 |

OTHER PUBLICATIONS

Gakh et al, Bioorganic & Medicinal Chemistry Letters (2013),23(5), 1262-1268.*
Ahmed et al. (2015) "Transcriptional Activation of Inflammatory Genes: Mechanistic Insight into Selectivity and Diversity" *Biomolecules* 5(4):3087-111.
Ballatore et al. (2013) "Carboxylic acid (bio)isosteres in drug design" *ChemMedChem* 8(3):385-95.
Berent-Spillson and Russell (2007) "Metabotropic glutamate receptor 3 protects neurons from glucose-induced oxidative injury by increasing intracellular glutathione concentration" *Journal of neurochemistry* 101(2):342-54.
Blaser, et al. (2016) "TNF and ROS Crosstalk in Inflammation." *Trends in cell biology.* 26(4):249-61.
Bogdanik et al. (2015) "Systemic, postsymptomatic antisense oligonucleotide rescues motor unit maturation delay in a new mouse model for type II/III spinal muscular atrophy" *Proceedings of the National Academy of Sciences of the United States of America* 112(43):E5863-72.
Bursavich, et al. (2001) "2-Anilino-4-aryl-1,3-thiazole inhibitors of valosin-containing protein (VCP or p97)" *Bioorganic & Medicinal Chemistry Letters* 20(5): 1677-1679.
Carri et al. (2015) "Oxidative stress and mitochondrial damage: importance in non-SOD1 ALS" *Frontiers in cellular neuroscience* 9:41.
Chen et al. (2009) "The proteasome-associated deubiquitinating enzyme Usp14 is essential for the maintenance of synaptic ubiquitin levels and the development of neuromuscular junctions" *The Journal of neuroscience: the official journal of the Society for Neuroscience* 29(35):10909-19.
Cowell et al. (2003) "Complement activation contributes to hypoxic-ischemic brain injury in neonatal rats" *The Journal of neuroscience: the official journal of the Society for Neuroscience* 23(28):9459-68.
Cowell et al. (2006) "Microglial expression of chemokine receptor CCR5 during rat forebrain development and after perinatal hypoxia-ischemia" *Journal of neuroimmunology* 173(1-2):155-65.

(Continued)

*Primary Examiner* — Kamal A Saeed
(74) *Attorney, Agent, or Firm* — Ballard Spahr LLP

(57) ABSTRACT

The present disclosure is concerned with 2-aminoaryl-5-aryloxazole compounds that are capable of activating NF-κB signaling. The present disclosure is also concerned with methods of using these compounds for the treatment of neurological disorders such as, for example, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD), and neuromuscular disorders such as, for example, Duchenne muscular dystrophy (DMD). This abstract is intended as a scanning tool for purposes of searching in the particular art and is not intended to be limiting of the present invention.

13 Claims, 19 Drawing Sheets

(56) References Cited

OTHER PUBLICATIONS

Cowell et al. (2007) "Localization of the transcriptional coactivator PGC-1alpha to GABAergic neurons during maturation of the rat brain" *The Journal of comparative neurology* 502(1):1-18.
Cowell et al. (2009) "Identification of novel targets for PGC-1alpha and histone deacetylase inhibitors in neuroblastoma cells" *Biochemical and biophysical research communications* 379(2):578-82.
Dhar, et al. (2002) "A modified approach to 2-(N-aryl)-1,3-oxazoles: application to the synthesis of the IMPDH inhibitor BMS-337197 and analogues" *Organic Letters* 4(12): 2091-2093.
Dhar, et al. (2002) "Discovery of N-[2-[2-[[3-methoxy-4-(5-oxazolyl)phenyl]amino]-5-oxazolyl]phenyl]-N-methyl-4-morpholineacetamide as a novel and potent inhibitor of inosine monophosphate dehydrogenase with excellent in vivo activity" *J. Med. Chem.* 45(11): 2127-2130.
Dougherty et al. (2012) "Disruption of Purkinje cell function prior to huntingtin accumulation and cell loss in an animal model of Huntington disease" *Experimental neurology* 236(1):171-8.
Dougherty et al. (2014) "Hyperactivity and cortical disinhibition in mice with restricted expression of mutant huntingtin to parvalbumin-positive cells" *Neurobiology of disease* 62:160-71.
Dougherty et al. (2014) "Mice lacking the transcriptional coactivator PGC-1α exhibit alterations in inhibitory synaptic transmission in the motor cortex" *Neuroscience* 271:137-48.
Dougherty et al. (2013) "Purkinje cell dysfunction and loss in a knock-in mouse model of Huntington disease" *Experimental neurology* 240:96-102.
Galasso et al. (2000) "Acute excitotoxic injury induces expression of monocyte chemoattractant protein-1 and its receptor, CCR2, in neonatal rat brain" *Experimental neurology* 165(2):295-305.
Gallardo-Godoy et al. (2011) "2-Aminothiazoles as therapeutic leads for prion diseases" *Journal of medicinal chemistry* 54(4):1010-21.
Golubev, et al. (2013) "A simple, three-component synthesis of 2-aminothiazoles using trimethylsilyl isothiocyanate" *Tet. Lett.* 54(36): 4844-4847.
Gurney et al. (1994) "Motor neuron degeneration in mice that express a human Cu,Zn superoxide dismutase mutation" *Science* 264(5166):1772-5.
Guyenet et al. (2010) "A simple composite phenotype scoring system for evaluating mouse models of cerebellar ataxia" *Journal of visualized experiments: JoVE* 21(39).
Hammam et al. (1985) *Egyptian Journal of Chemistry* 27:515-23.
Henkel et al. (2009) "Microglia in ALS: the good, the bad, and the resting" *Journal of neuroimmune pharmacology: the official journal of the Society on NeuroImmune Pharmacology* 4(4):389-98.
Ho et al. (2009) "Regulation of transcription factors by heterotrimeric G proteins" *Current molecular pharmacology* 2(1):19-31.
Hoekman and Ho (2011) "Enhanced analgesic responses after preferential delivery of morphine and fentanyl to the olfactory epithelium in rats" *Anesthesia and analgesia* 113(3):641-51.
Ikiz, et al. (2015) "The Regulatory Machinery of Neurodegeneration in In Vitro Models of Amyotrophic Lateral Sclerosis." *Cell reports.* 12(2):335-45.
Jiang et al. (2013) "Social isolation exacerbates schizophrenia-like phenotypes via oxidative stress in cortical interneurons" *Biological psychiatry* 73(10):1024-34.
Jiang et al. (2013) "Convergence of genetic and environmental factors on parvalbumin-positive interneurons in schizophrenia" *Frontiers in behavioral neuroscience* 7:116.
Kaltschmidt et al. (2005) "Signaling via NF-kappaB in the nervous system" *Biochimica et biophysica acta* 1745(3):287-99.
Kuntzen et al. (2007) "A method for isolating prosurvival targets of NF-kappaB/Rel transcription factors" *Methods in molecular biology* 399:99-124.
Lagoja, et al. (2011) "Substituted 2-aminothiazoles are exceptional inhibitors of neuronal degeneration in tau-driven models of Alzheimer's disease" *European Journal of Pharmaceutical Sciences* 43(5): 386-392.
Landis et al. (2012) "Nasal-to-CNS drug delivery: where are we now and where are we heading? An industrial perspective" *Therapeutic delivery* 3(2):195-208.
Lochhead and Thorne (2012) "Intranasal delivery of biologics to the central nervous system" *Advanced drug delivery reviews* 64(7):614-28.
Lucas et al. (2012) "Developmental alterations in motor coordination and medium spiny neuron markers in mice lacking pgc-1α" *PloS one* 7(8):e42878.
Lucas et al. (2014) "PGC-1α provides a transcriptional framework for synchronous neurotransmitter release from parvalbumin-positive interneurons" *The Journal of neuroscience: the official journal of the Society for Neuroscience* 34(43):14375-87.
Manuvakhova et al. (2011) "Identification of novel small molecule activators of nuclear factor-κB with neuroprotective action via high-throughput screening" *Journal of neuroscience research* 89(1):58-72.
Marini et al. (2004) "Role of brain-derived neurotrophic factor and NF-kappaB in neuronal plasticity and survival: From genes to phenotype" *Restorative neurology and neuroscience* 22(2):121-30.
Martin et al. (2015) "Functional and morphological assessment of diaphragm innervation by phrenic motor neurons" *Journal of visualized experiments: JoVE* 25(99):e52605.
Melanie Leitner PDSM, Ph.D.; Cathleen Lutz, Ph.D. Working with ALS Mice: Guidelines for preclinical testing & colony management. Cambridge, MA: Prize4Life; 2009.
Moehle et al. (2012) "LRRK2 inhibition attenuates microglial inflammatory responses" *The Journal of neuroscience: the official journal of the Society for Neuroscience* 32(5):1602-11.
Nardo et al. (2016) "New Insights on the Mechanisms of Disease Course Variability in ALS from Mutant SOD1 Mouse Models" *Brain pathology* 26(2):237-47.
Neidl et al. (2016) "Late-Life Environmental Enrichment Induces Acetylation Events and Nuclear Factor κB-Dependent Regulations in the Hippocampus of Aged Rats Showing Improved Plasticity and Learning" *The Journal of neuroscience: the official journal of the Society for Neuroscience* 36(15):4351-61.
Periasamy et al. (2016) "An Immature Myeloid/Myeloid-Suppressor Cell Response Associated with Necrotizing Inflammation Mediates Lethal Pulmonary Tularemia" *PLoS pathogens* 12(3):e1005517.
Petrov et al. (2017) "ALS Clinical Trials Review: 20 Years of Failure. Are We Any Closer to Registering a New Treatment?" *Frontiers in aging neuroscience* 9:68.
Philips and Rothstein (2015) "Rodent Models of Amyotrophic Lateral Sclerosis" *Current protocols in pharmacology* 69:5 67 1-21.
Pizzi et al. (2009) "Post-ischemic brain damage: NF-kappaB dimer heterogeneity as a molecular determinant of neuron vulnerability" *The FEBS journal* 276(1):27-35.
Sarnico et al. (2009) "NF-kappaB dimers in the regulation of neuronal survival" *International review of neurobiology* 85:351-62.
Scott et al. (2008) "Design, power, and interpretation of studies in the standard murine model of ALS" *Amyotrophic lateral sclerosis* 9(1):4-15.
Si et al. (2014) "Smads as muscle biomarkers in amyotrophic lateral sclerosis" *Annals of clinical and translational neurology* 1(10):778-87.
Si et al. (2015) "Transforming Growth Factor Beta (TGF-β) Is a Muscle Biomarker of Disease Progression in ALS and Correlates with Smad Expression" *PloS one* 10(9):e0138425.
Skibsbye et al. (2015) "Antiarrhythmic Mechanisms of SK Channel Inhibition in the Rat Atrium" *Journal of cardiovascular pharmacology* 66(2):165-76.
Trstenjak et al. (2013) "Low molecular weight dual inhibitors of factor Xa and fibrinogen binding to GPIIb/IIIa with highly overlapped pharmacophores" *European journal of medicinal chemistry* 64:302-13.
Vaden et al. (2015) "Distinct effects of ubiquitin overexpression on NMJ structure and motor performance in mice expressing catalytically inactive USP14" *Frontiers in molecular neuroscience* 8:11.

(56) References Cited

OTHER PUBLICATIONS

Writing and Edaravone (2017) "Safety and efficacy of edaravone in well-defined patients with amyotrophic lateral sclerosis: a randomised, double-blind, placebo-controlled trial" The Lancet Neurology 16(7):505-12.

Xia et al. (2010) "Dorsal caudal tail and sciatic motor nerve conduction studies in adult mice: technical aspects and normative data" *Muscle & nerve* 41(6):850-6.

Chemical Abstracts Registry No. 324775-74-8, indexed in the Registry File on ACS on STN, Feb. 28, 2001.

Chemical Abstracts Registry No. 303150-09-6, indexed in the Registry File on ACS on STN, Nov. 17, 2000.

Chemical Abstracts Registry No. 1797019-23-8 (https://www.chemicalbook.com/ProductChemicalPropertiesCB73389891_EN.htm).

\* cited by examiner

2-AMINOARYL-5-ARYLOXAZOLE ANALOGS FOR THE TREATMENT OF NEURODEGENERATIVE DISEASES

CROSS-REFERENCE TO RELATED APPLICATIONS

This Application is a continuation of U.S. application Ser. No. 16/968,039, filed on Aug. 6, 2020, which is a national stage filing under 35 U.S.C. § 371 of International Application No. PCT/US2019/018834, filed on Feb. 20, 2019, which claims the benefit of U.S. Provisional Application No. 62/633,577, filed on Feb. 21, 2018, the contents of which are incorporated herein by reference in their entireties.

BACKGROUND

Amyotrophic lateral sclerosis (ALS) is a rare, progressive, and incurable neurodegenerative disease. It affects adults 40 to 60 years of age with an incidence of 2:100,000. ALS causes irreversible degeneration of motor neurons, which is accompanied by paralysis of voluntary muscle leading to respiratory failure. Death occurs within 5 years on average from diagnosis. Abnormalities of the cytosolic enzyme CuZn superoxide dismutase (SOD1) and an increase in reactive oxygen species (ROS) are central to the disease pathogenesis. Mutations in critical regions of SOD1 have been identified in familial ALS (f-ALS), while conformational defects have been identified in sporadic ALS (s-ALS). Transgenic animals carrying high copy number of mutated SOD1 develop a disease similar to human ALS humans. A common feature of ALS is mitochondrial malady due to the excess of ROS and/or the localization of the mutated SOD1 in the outer mitochondrial matrix. SOD1 functional defect and its repercussions on mitochondrial health have led us to hypothesize that SOD2, an inducible mitochondrial enzyme, but spared in the disease, could be targeted to devise a novel approach to ALS treatment. Expression of SOD2 in the brain is uniquely controlled by NF-κB p65 activation.

Neuronal non-cytokine-dependent p50/p65 nuclear factor-κB (the primary NF-κB complex in the brain) activation has been shown to exert neuroprotective actions. Thus, neuronal activation of NF-κB could represent a viable neuroprotective target. However, despite this discovery, the development of potent and selective small molecule activators of NF-κB has remained elusive. Thus, there remains a need for agents capable of strengthening NF-κB signaling and methods of making and using same.

SUMMARY

In accordance with the purpose(s) of the invention, as embodied and broadly described herein, the invention, in one aspect, relates to compounds and compositions for use in the prevention and treatment of neurological disorders such as, for example, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD), and neuromuscular disorders such as, for example, Duchenne muscular dystrophy (DMD).

Disclosed are compounds having a structure represented by a formula selected from:

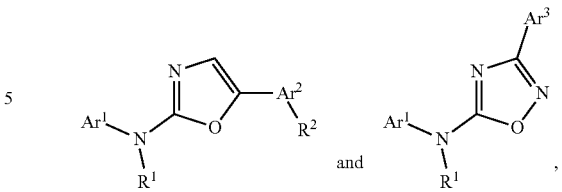

wherein $R^1$ is selected from hydrogen and C1-C4 alkyl; wherein $R^2$, when present, is selected from —C(F)=CHCH$_3$, —C(CN)=NOCH$_3$, —CO$_2R^{21}$, —SO$_2R^{21}$, —NR$^{22a}R^{22b}$, —CH$_2$NR$^{22a}R^{22b}$, —C(O)NR$^{22a}R^{22b}$, —CH(CF$_3$)NR$^{22a}R^{22b}$, —SO$_2$NR$^{22a}R^{22b}$, —NR$^{23}$SO$_2R^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

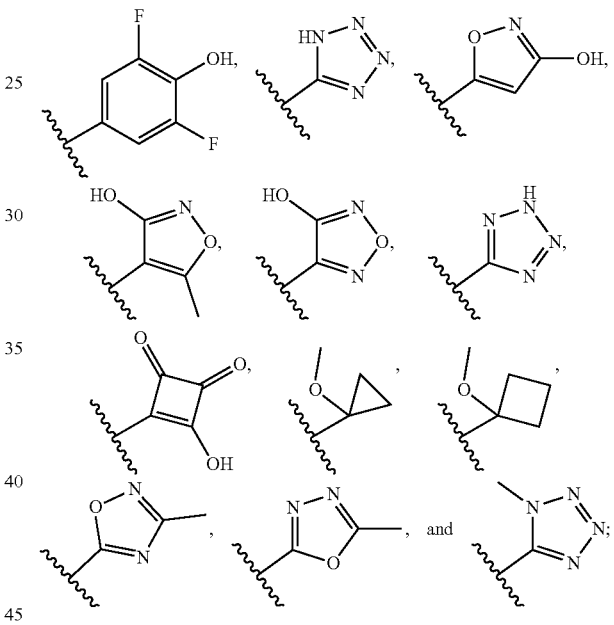

wherein Ar$^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^2$, when present, is selected from monocyclic aryl and pyridinyl, and is substituted with 0, 1, or 2 independently selected $R^4$ groups; wherein each occurrence of $R^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2R^{31}$, —SO$_2R^{31}$, —CO$_2$NR$^{32a}R^{32b}$, —CH(CF$_3$)NR$^{32a}R^{32b}$, —SO$_2$NR$^{32a}R^{32b}$, —NR$^{33}$SO$_2R^{34}$, and Cy$^1$; wherein each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and Cy$^1$; wherein Ar$^3$, when present, is selected from monocyclic aryl and pyridinyl, and is substituted with 0, 1, 2, or 3 $R^4$ groups; provided that when $R^1$ is hydrogen, $R^2$ is —CO$_2$H or —NH$_2$, and Ar$^2$ is monocyclic aryl, then Ar$^1$ is monocyclic aryl substituted with 1, 2, or 3 halogen groups or pyridinyl, and provided that either $Ar^3$ is pyridinyl or when $Ar^3$ is monocyclic aryl, $R^1$ is hydrogen, or a pharmaceutically acceptable salt thereof.

Also disclosed are pharmaceutical compositions comprising a therapeutically effective amount of at least one disclosed compound and a pharmaceutically acceptable carrier.

Also disclosed are methods for the treatment of a neurological disorder in a subject, the method comprising the step of administering to the subject an effective amount of at least one disclosed compound.

Also disclosed are methods for the treatment of a neuromuscular disorder in a subject, the method comprising the step of administering to the subject an effective amount of at least one disclosed compound.

Also disclosed are methods for modifying NF-κB signaling in a subject, the method comprising the step of administering to the subject an effective amount of at least one disclosed compound.

Also disclosed are methods for modifying NF-κB signaling in at least one cell, the method comprising the step of contacting at least one cell with an effective amount of at least one disclosed compound.

Also disclosed are methods for modifying brain-derived neurotrophic factor signaling in a subject, the method comprising the step of administering to the subject an effective amount of at least one disclosed compound.

Also disclosed are methods for modifying brain-derived neurotrophic factor signaling in at least one cell, the method comprising the step of contacting at least one cell with an effective amount of at least one disclosed compound.

Also disclosed are kits comprising at least one disclosed compound and one or more of (a) at least one agent associated with the treatment of a neurological disorder; (b) at least one agent associated with the treatment of a neuromuscular disorder; (c) instructions for administering the compound in connection with treating a neurological disorder; (d) instructions for administering the compound in connection with reducing the risk of a neurological disorder; (e) instructions for treating a neurological disorder; (f) instructions for administering the compound in connection with treating a neuromuscular disorder; (g) instructions for administering the compound in connection with reducing the risk of a neuromuscular disorder; and (h) instructions for treating a neuromuscular disorder.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figures 1A, 1B:
FIG. 1A and FIG. 1B show representative data from a quantitative RT-PCR for Manganese superoxide dismutase (SOD2; FIG. TA) or brain-derived neurotrophic factor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and cosolvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Momson and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$- or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $N_3$.

The term "nitro" as used herein is represented by the formula $NO_2$.

The term "nitrile" or "cyano" as used herein is represented by the formula CN.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

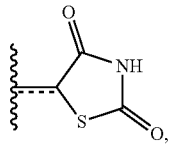

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

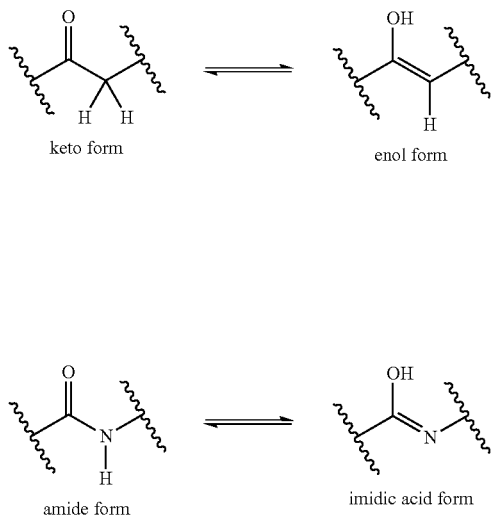

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

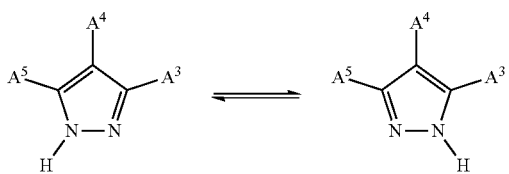

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

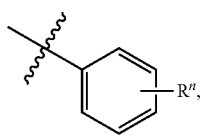

which is understood to be equivalent to a formula:

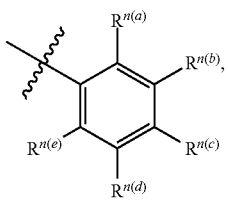

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with a neurological disorder such as, for example, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD), and/or neuromuscular disorders such as, for example, Duchenne muscular dystrophy (DMD).

In one aspect, the disclosed compounds exhibit modification of NF-κB signaling. In a further aspect, the disclosed compounds exhibit activation of NF-κB signaling.

In one aspect, the compounds of the invention are useful in modifying NF-κB signaling in a mammal. In a further aspect, the compounds of the invention are useful in modifying NF-κB signaling in at least one cell.

In one aspect, the compounds of the invention are useful in the treatment of neurological disorders, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

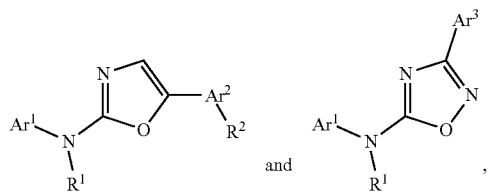

wherein $R^1$ is selected from hydrogen and C1-C4 alkyl; wherein $R^2$, when present, is selected from —C(F)=CHCH$_3$, —C(CN)=NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

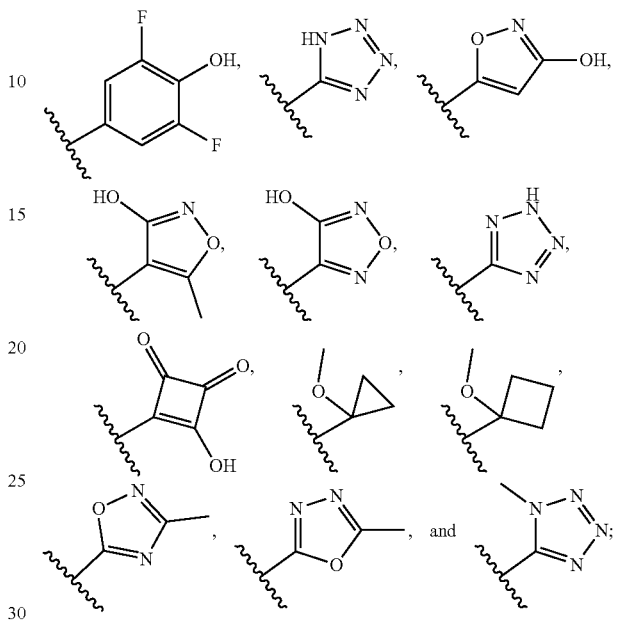

wherein Ar$^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^2$, when present, is selected from monocyclic aryl and pyridinyl, and is substituted with 0, 1, or 2 independently selected R$^4$ groups; wherein each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$; wherein each of R$^{31}$, R$^{32a}$, R$^{32b}$, R$^{33}$, and R$^{34}$, when present, is independently selected from hydrogen, halogen, C1-C4 alkyl, C1-C4 alkoxy, C1-C4 haloalkyl, and Cy$^1$; wherein Ar$^3$, when present, is selected from monocyclic aryl and pyridinyl, and is substituted with 0, 1, 2, or 3 R$^4$ groups; provided that when R$^1$ is hydrogen, R$^2$ is —CO$_2$H or —NH$_2$, and Ar$^2$ is monocyclic aryl, then Ar$^1$ is monocyclic aryl substituted with 1, 2, or 3 halogen groups or pyridinyl, and provided that either Ar$^3$ is pyridinyl or when Ar$^3$ is monocyclic aryl, R$^1$ is hydrogen, or a pharmaceutically acceptable salt thereof.

In a further aspect, the compound has a structure represented by a formula:

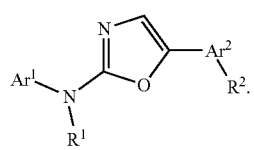

In a further aspect, the compound has a structure represented by a formula:

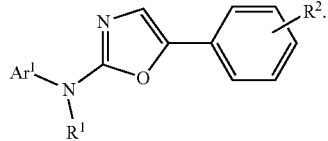

In a further aspect, the compound has a structure represented by a formula:

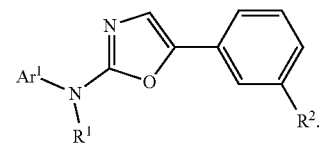

In a further aspect, the compound has a structure represented by a formula:

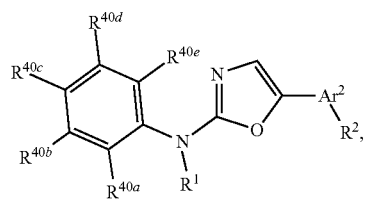

wherein each of $R^{40a}$, $R^{40b}$, $R^{40c}$, $R^{40d}$, and $R^{40e}$ is independently selected from hydrogen, halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkyl amino.

In a further aspect, the compound is selected from:

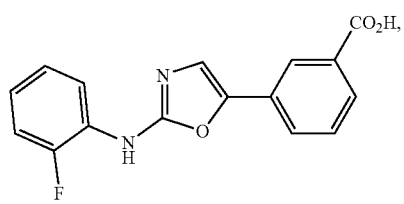

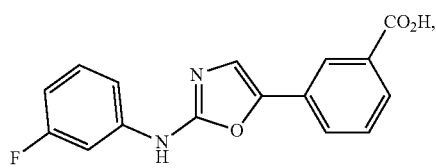

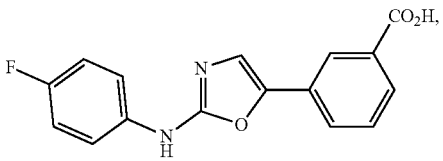

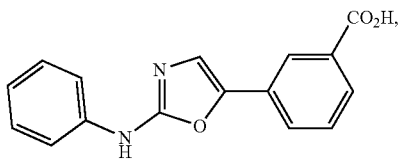

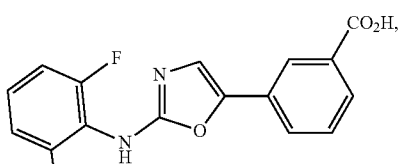

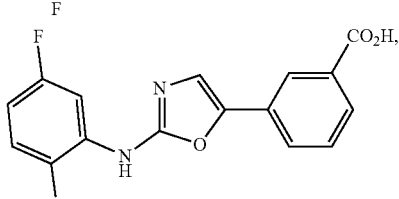

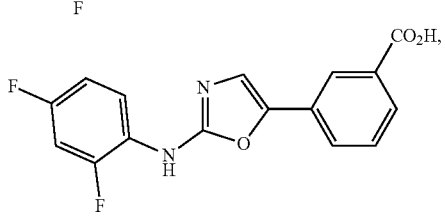

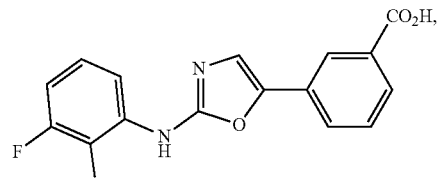

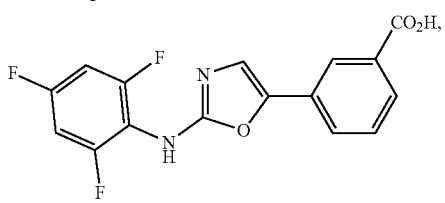

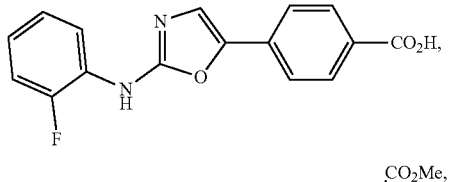

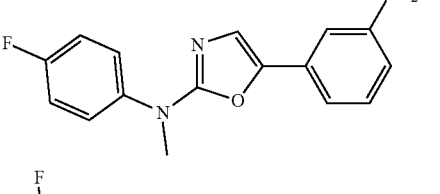

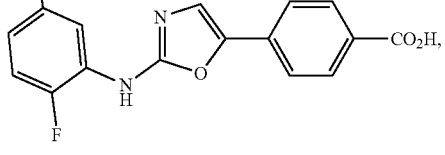

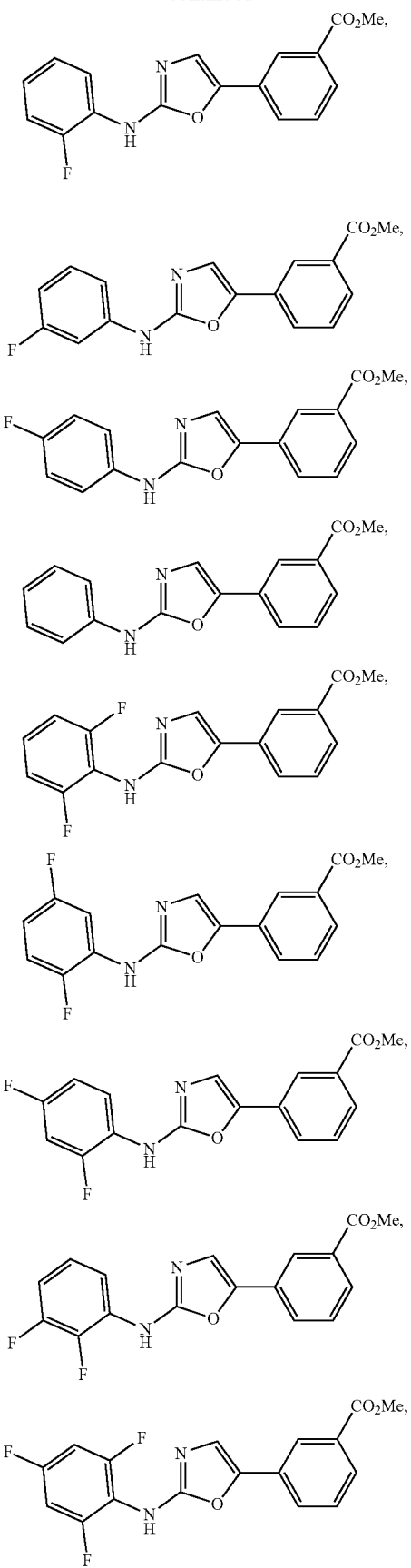
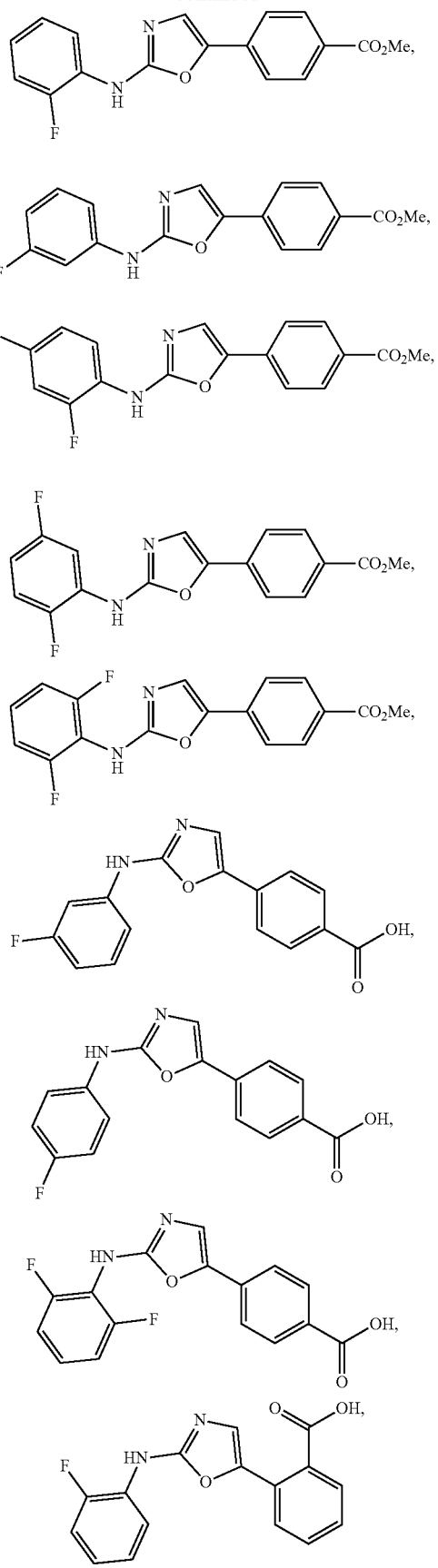

-continued
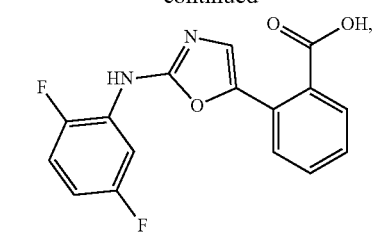
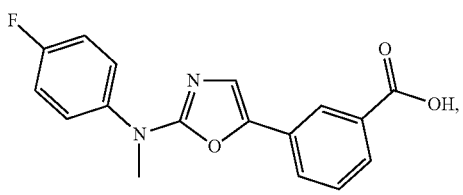
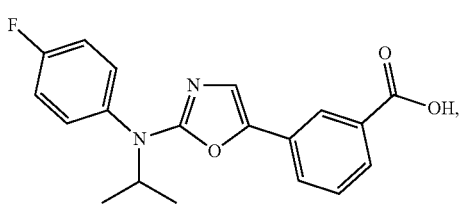
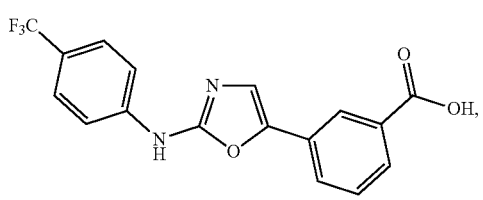
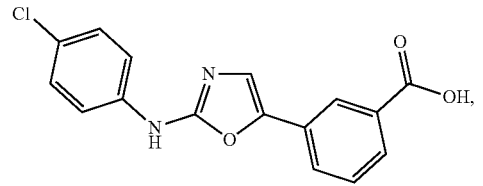
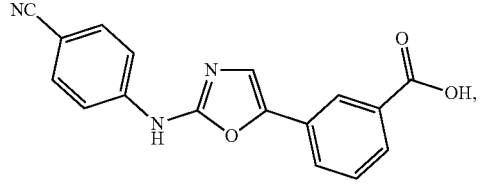
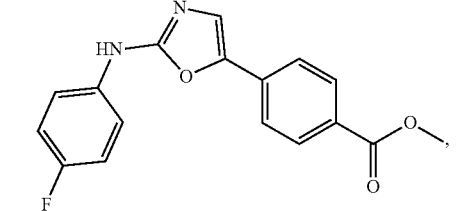
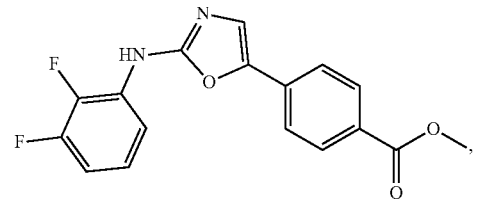
-continued
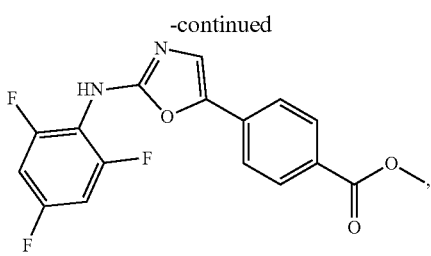
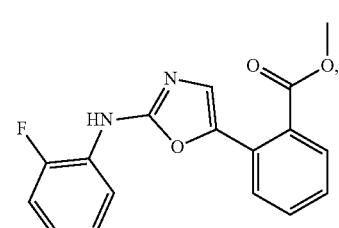
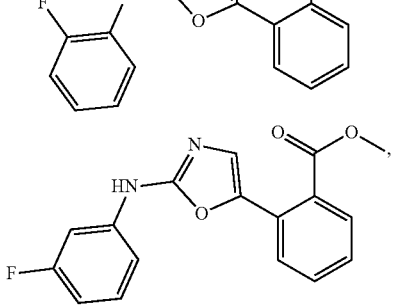
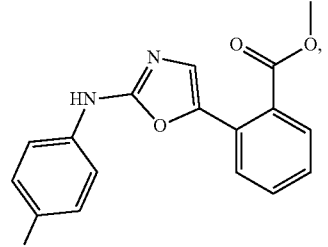
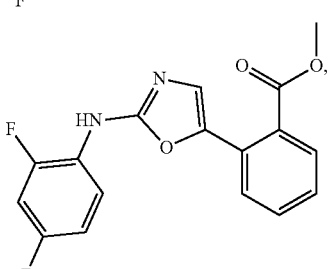
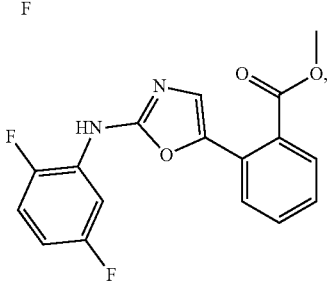
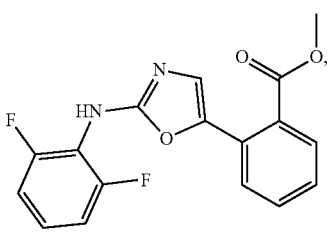

-continued
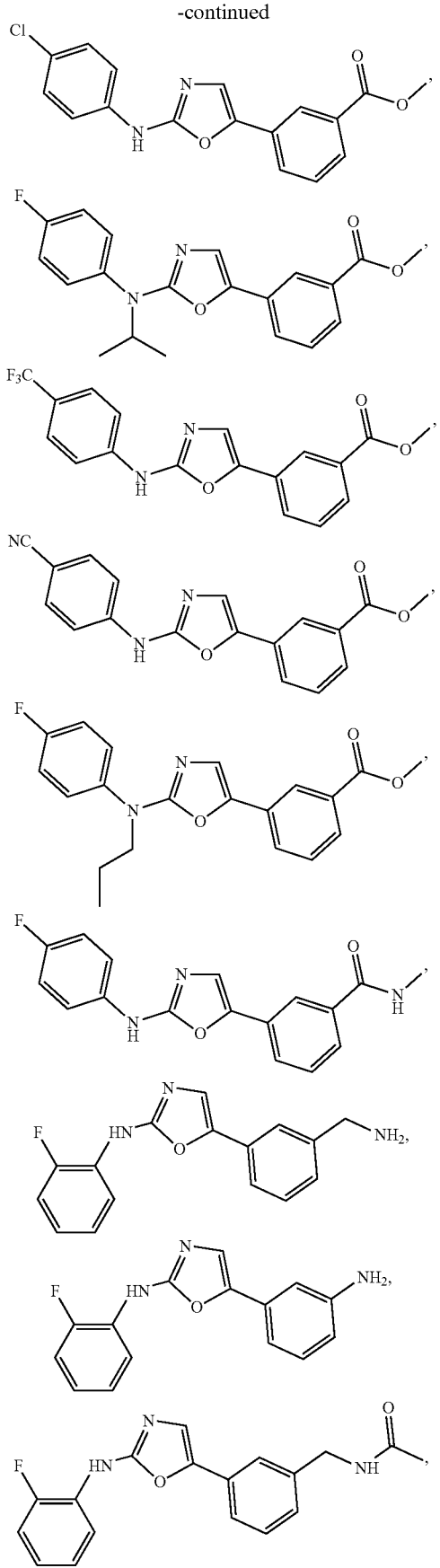
-continued
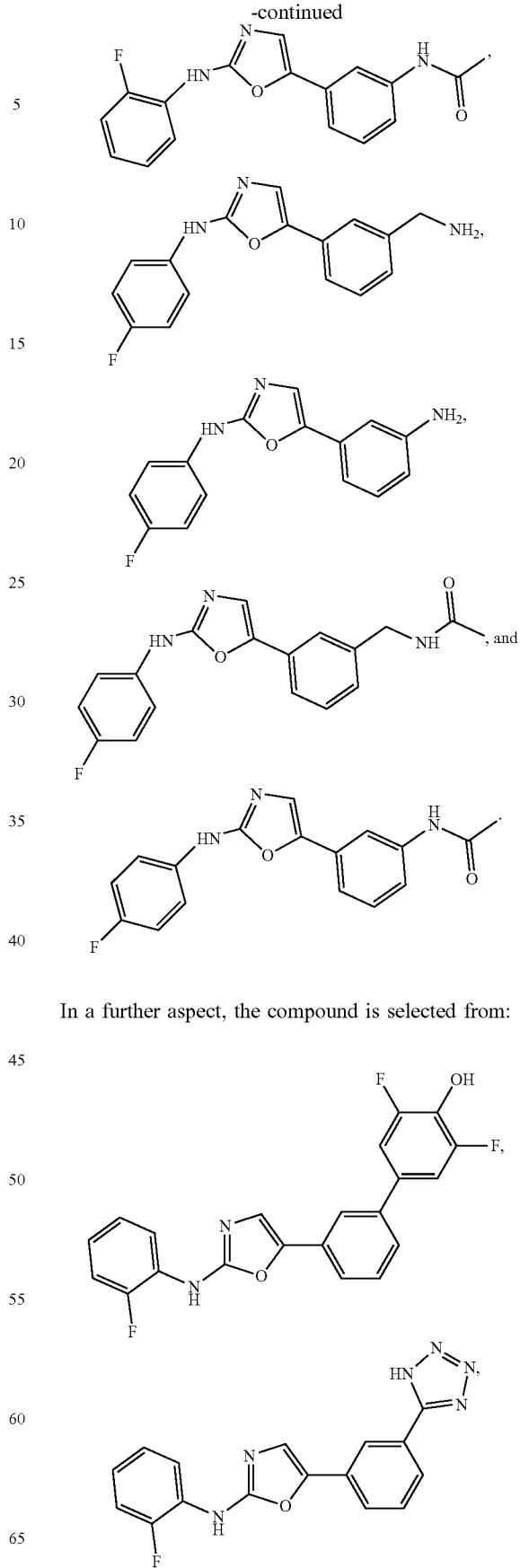
In a further aspect, the compound is selected from:
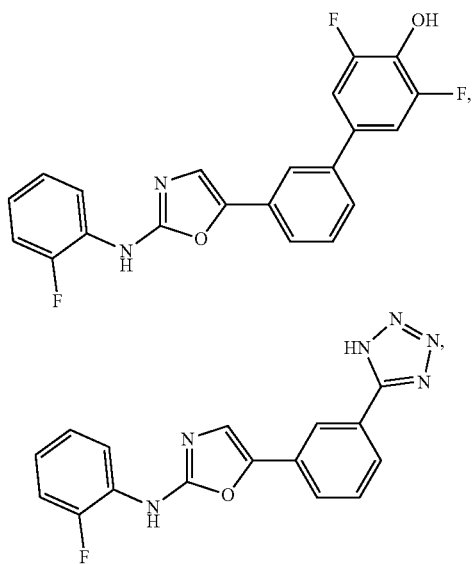

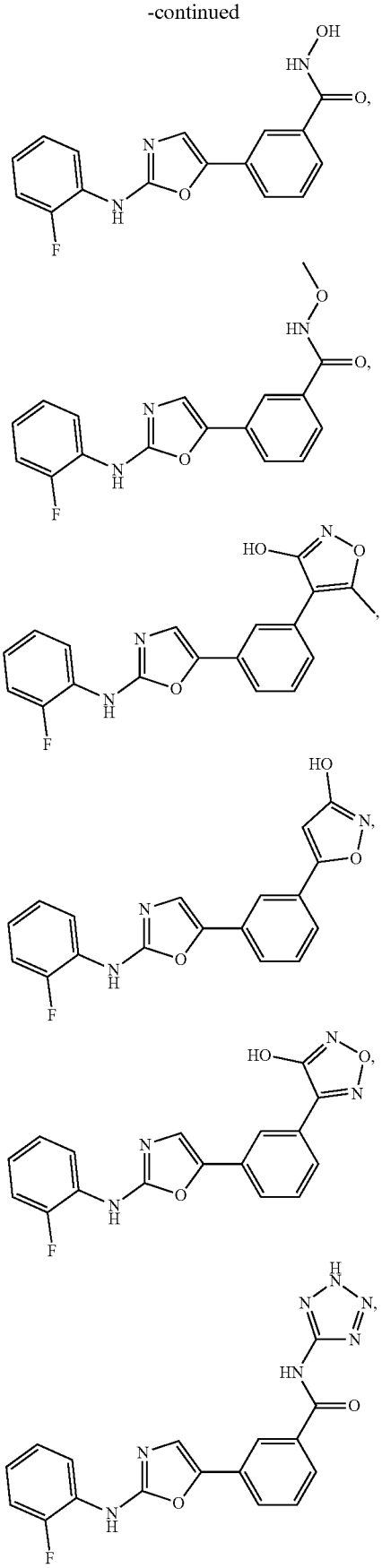
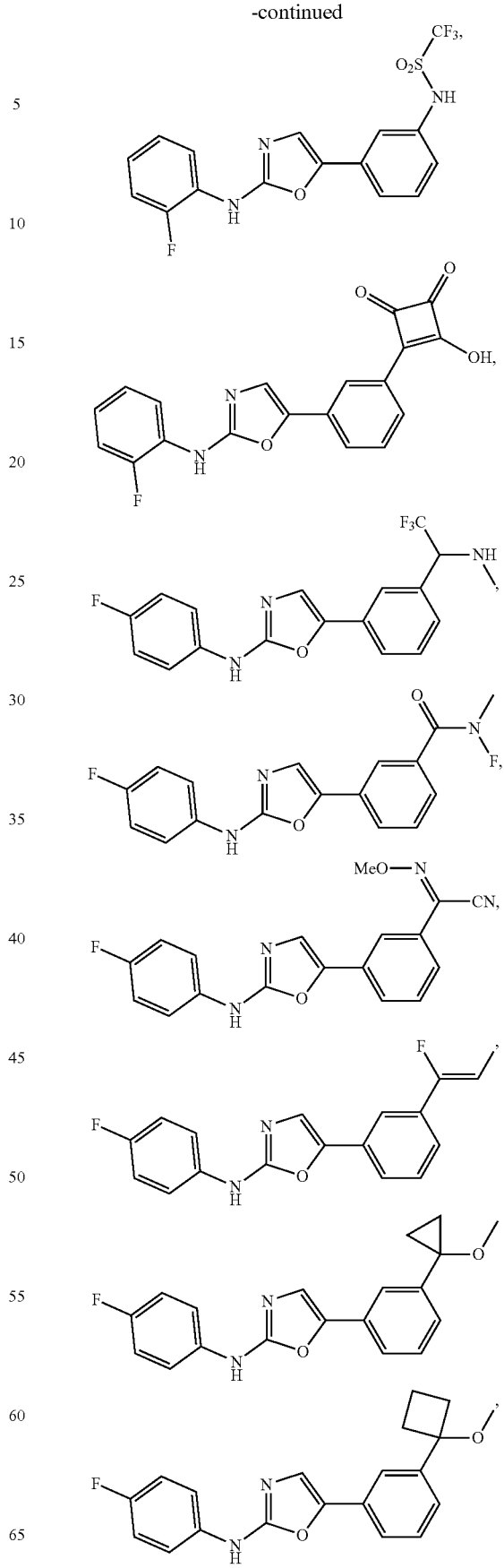

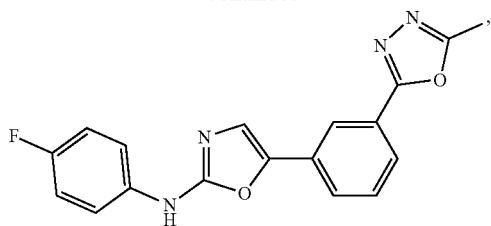

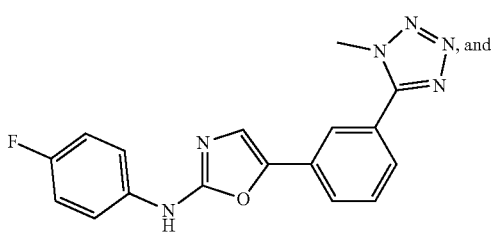

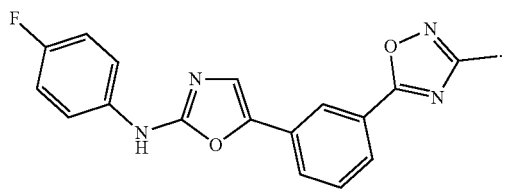

In a further aspect, the compound has a structure represented by a formula:

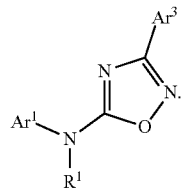

In a further aspect, the compound has a structure represented by a formula:

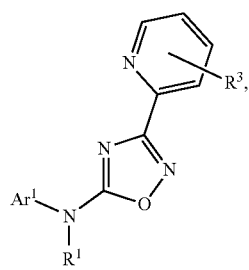

wherein R³ is selected from —C(F)=CHCH₃, —C(CN)=NOCH₃, —CO₂R²¹, —SO₂R²¹, —NR²²ᵃR²²ᵇ, —CH₂NR²²ᵃR²²ᵇ, —C(O)NR²²ᵃR²²ᵇ, —CH(CF₃)NR²²ᵃR²²ᵇ, —SO₂NR²²ᵃR²²ᵇ, —NR²³SO₂R²⁴, and Cy¹.

In a further aspect, the compound has a structure represented by a formula:

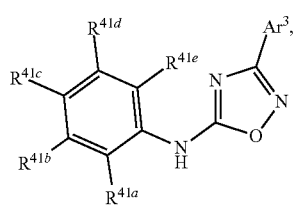

wherein each of R⁴¹ᵃ, R⁴¹ᵇ, R⁴¹ᶜ, R⁴¹ᵈ, and R⁴¹ᵉ, when present, is independently selected from hydrogen, halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, the compound has a structure represented by a formula:

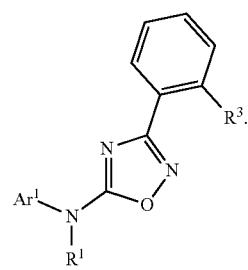

In a further aspect, the compound has a structure represented by a formula selected from:

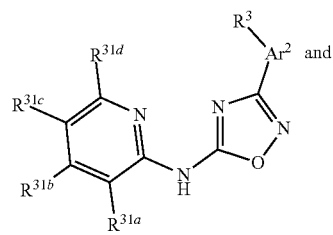

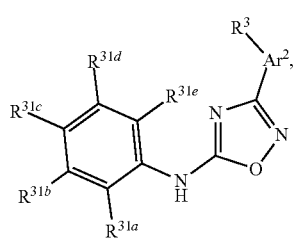

wherein each of R³¹ᵃ, R³¹ᵇ, R³¹ᶜ, R³¹ᵈ, and R³¹ᵉ, when present, is independently selected from hydrogen, halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, the compound is:

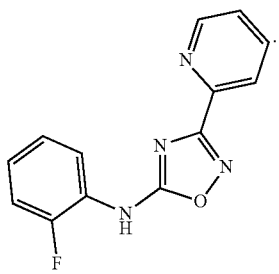 [SMILES: Fc1ccccc1Nc1nc(-c2ccccn2)no1]

In a further aspect, R$^2$, when present, is selected from —C(F)=CHCH$_3$, —C(CN)=NOCH$_3$, —CO$_2$R$^{21}$, —SO$_2$R$^{21}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$, and each of R$^{21}$, R$^{22a}$, R$^{22b}$, R$^{23}$, and R$^{24}$, when present, is independently selected from hydrogen, halogen, C1-C4 alkyl, C1-C4 haloalkyl, and Cy$^1$, provided that R$^{22a}$ and R$^{22b}$ are not simultaneously hydrogen.

In a further aspect, the compound is not:

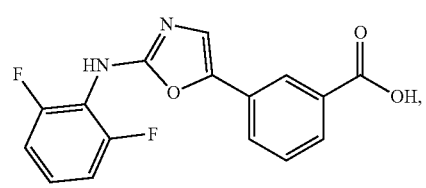

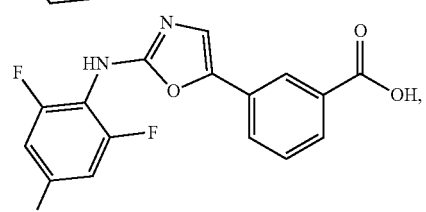

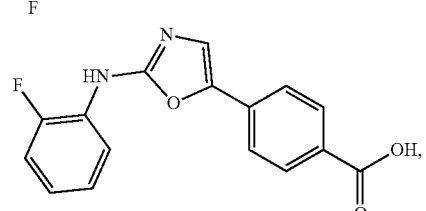

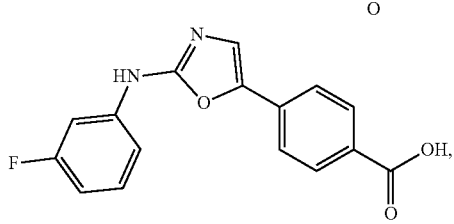

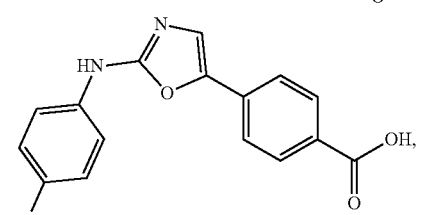

-continued

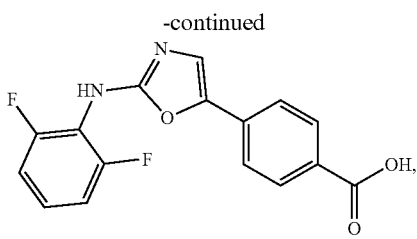

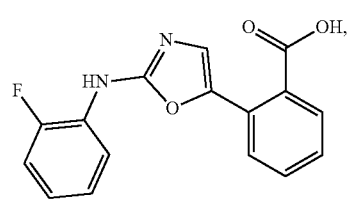

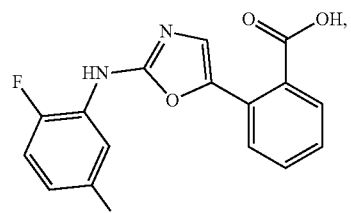

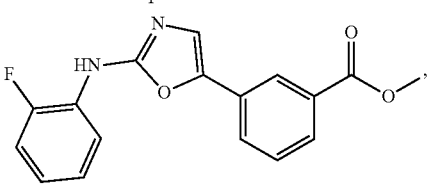

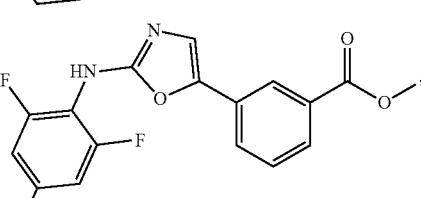

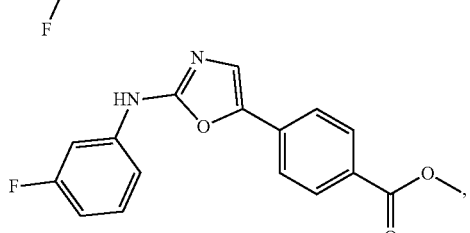

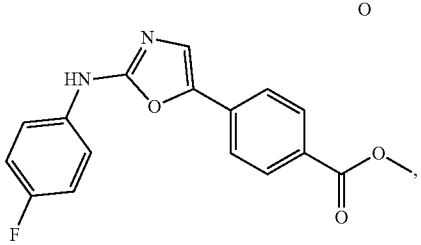

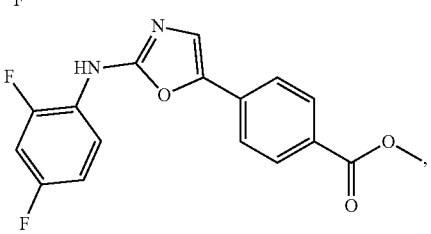

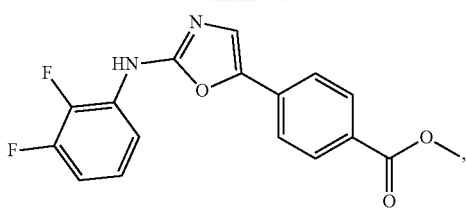
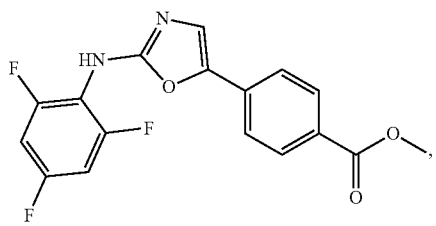
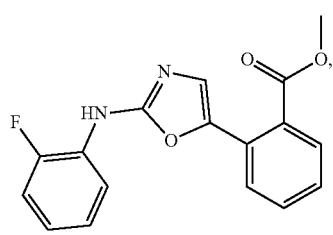
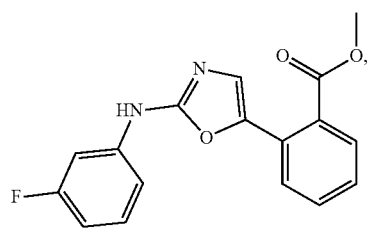
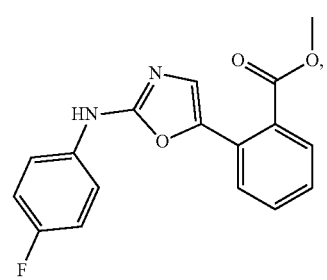
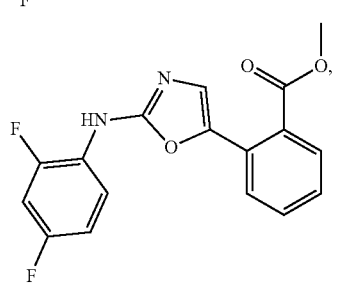
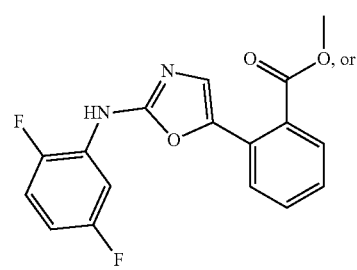
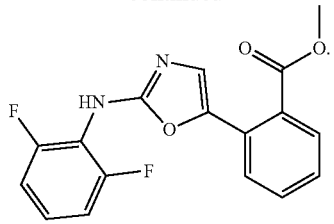

a. $R^1$ Groups

In one aspect, $R^1$ is selected from hydrogen and C1-C4 alkyl. In a further aspect, $R^1$ is hydrogen.

In a further aspect, $R^1$ is selected from hydrogen, methyl, ethyl, n-propyl, i-propyl, n-butyl, i-butyl, and t-butyl. In a still further aspect, $R^1$ is selected from hydrogen, methyl, ethyl, n-propyl, and i-propyl. In yet a further aspect, $R^1$ is selected from hydrogen, methyl, and ethyl. In an even further aspect, $R^1$ is selected from hydrogen and ethyl. In a still further aspect, $R^1$ is selected from hydrogen and methyl.

In a further aspect, $R^1$ is C1-C4 alkyl. In a still further aspect, $R^1$ is selected from methyl, ethyl, n-propyl, and i-propyl. In yet a further aspect, $R^1$ is selected from methyl and ethyl. In an even further aspect, $R^1$ is ethyl. In a still further aspect, $R^1$ is methyl.

b. $R^2$ Groups

In one aspect, $R^2$, when present, is selected from —C(F)=CHCH$_3$, —C(CN)=NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$.

In a further aspect, $R^2$, when present, is selected from —C(F)=CHCH$_3$, —C(CN)=NOCH$_3$, —CO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, and Cy$^1$. In a still further aspect, $R^2$, when present, is selected from —C(F)=CHCH$_3$, —C(CN)=NOCH$_3$, —CO$_2$R$^{21}$, —C(O)NR$^{22a}$R$^{22b}$, —CH(CF$_3$)NR$^{22a}$R$^{22b}$, and Cy$^1$. In yet a further aspect, $R^2$, when present, is selected from —C(F)=CHCH$_3$, —C(CN)=NOCH$_3$, —CH(CF$_3$)NR$^{22a}$R$^{22b}$, and Cy$^1$. In an even further aspect, $R^2$, when present, is selected from —CH(CF$_3$)NR$^{22a}$R$^{22b}$ and Cy$^1$. In a still further aspect, $R^2$, when present, is —CH(CF$_3$)NR$^{22a}$R$^{22b}$. In yet a further aspect, $R^2$, when present, is Cy$^1$.

In a further aspect, $R^2$, when present, is selected from —C(F)=CHCH$_3$, —C(CN)=NOCH$_3$, —CO$_2$R$^{21}$, —SO$_2$R$^{21}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$. In a still further aspect, $R^2$, when present, is selected from —C(F)=CHCH$_3$, —C(CN)=NOCH$_3$, —CO$_2$R$^{21}$, —SO$_2$R$^{21}$, —C(O)NR$^{22a}$R$^{22b}$, —SO$_2$NR$^{22a}$R$^{22b}$, —NR$^{23}$SO$_2$R$^{24}$, and Cy$^1$. In yet a further aspect, $R^2$, when present, is selected from —C(F)=CHCH$_3$, —C(CN)=NOCH$_3$, —CO$_2$R$^{21}$, —C(O)NR$^{22a}$R$^{22b}$, and Cy$^1$. In an even further aspect, $R^2$, when present, is selected from —C(F)=CHCH$_3$, —C(CN)=NOCH$_3$, and Cy$^1$. In a still further aspect, $R^2$, when present, is selected from —C(F)=CHCH$_3$ and —C(CN)=NOCH$_3$. In yet a further aspect, $R^2$, when present, is —C(F)=CHCH$_3$. In an even further aspect, $R^2$, when present, is —C(CN)=NOCH$_3$.

In a further aspect, $R^2$, when present, is selected from —C(F)=CHCH$_3$, —C(CN)=NOCH$_3$, —SO$_2$R$^{21}$, —NR$^{22a}$R$^{22b}$, —CH$_2$NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$. In a still further aspect, $R^2$, when present, is selected from —SO$_2$R$^{21}$, —NR$^{22a}$R$^{22b}$, —CH$_2$NR$^{22a}$R$^{22b}$, —CH(CF$_3$)NR$^{22a}$R$^{22b}$, —$SO_2NR^{22a}R^{22b}$, —$NR^{23}SO_2R^{24}$, and $Cy^1$. In yet a further aspect, $R^2$, when present, is selected from —$SO_2R^{21}$, —$SO_2NR^{22a}R^{22b}$, —$NR^{23}SO_2R^{24}$, and $Cy^1$. In an even further aspect, $R^2$, when present, is selected from —$SO_2R^{21}$, —$SO_2NR^{22a}R^{22b}$, and —$NR^{23}SO_2R^{24}$. In a still further aspect, $R^2$, when present, is selected from —$SO_2R^{21}$ and —$SO_2NR^{22a}R^{22b}$. In yet a further aspect, $R^2$, when present, is selected from —$SO_2NR^{22a}R^{22b}$ and —$NR^{23}SO_2R^{24}$. In an even further aspect, $R^2$, when present, is —$SO_2R^{21}$. In a still further aspect, $R^2$, when present, is —$SO_2NR^{22a}R^{22b}$. In yet a further aspect, $R^2$, when present, is —$NR^{23}SO_2R^{24}$.

In a further aspect, $R^2$, when present, is selected from —$CO_2R^{21}$, —$SO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, —$SO_2NR^{22a}R^{22b}$, —$NR^{23}SO_2R^{24}$, and $Cy^1$. In a still further aspect, $R^2$, when present, is selected from —$CO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, and $Cy^1$. In yet a further aspect, $R^2$, when present, is selected from —$CO_2R^{21}$, —$NR^{22a}R^{22b}$, —$CH_2NR^{22a}R^{22b}$, —$C(O)NR^{22a}R^{22b}$, and $Cy^1$. In an even further aspect, $R^2$, when present, is selected from —$CO_2R^{21}$, —$C(O)NR^{22a}R^{22b}$, and $Cy^1$. In a still further aspect, $R^2$, when present, is selected from —$CO_2R^{21}$ and —$C(O)NR^{22a}R^{22b}$. In yet a further aspect, $R^2$, when present, is —$CO_2R^{21}$. In an even further aspect, $R^2$, when present, is —$C(O)NR^{22a}R^{22b}$.

In a further aspect, $R^2$, when present, is selected from —$C(F)=CHCH_3$, —$C(CN)=NOCH_3$, —$CO_2R^{21}$, —$SO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, —$SO_2NR^{22a}R^{22b}$, and —$NR^{23}SO_2R^{24}$. In a still further aspect, $R^2$, when present, is selected from —$C(F)=CHCH_3$, —$C(CN)=NOCH_3$, —$CO_2R^{21}$, —$NR^{22a}R^{22b}$, —$CH_2NR^{22a}R^{22b}$, —$C(O)NR^{22a}R^{22b}$, and —$CH(CF_3)NR^{22a}R^{22b}$. In yet a further aspect, $R^2$, when present, is selected from —$CO_2R^{21}$, —$NR^{22a}R^{22b}$, —$CH_2NR^{22a}R^{22b}$, —$C(O)NR^{22a}R^{22b}$, and —$CH(CF_3)NR^{22a}R^{22b}$. In an even further aspect, $R^2$, when present, is selected from —$NR^{22a}R^{22b}$ and —$CH_2NR^{22a}R^{22b}$. In a still further aspect, $R^2$, when present, is —$NR^{22a}R^{22b}$. In yet a further aspect, $R^2$, when present, is —$CH_2NR^{22a}R^{22b}$.

In a further aspect, $R^2$, when present, is selected from —$C(F)=CHCH_3$, —$C(CN)=NOCH_3$, —$CO_2R^{21}$, —$SO_2R^{21}$, —$C(O)NR^{22a}R^{22b}$, —$CH(CF_3)NR^{22a}R^{22b}$, —$SO_2NR^{22a}R^{22b}$, —$NR^{23}SO_2R^{24}$, and $Cy^1$.

c. $R^3$ Groups

In one aspect, $R^3$ is selected from —$C(F)=CHCH_3$, —$C(CN)=NOCH_3$, —$CO_2R^{21}$, —$SO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, —$SO_2NR^{22a}R^{22b}$, —$NR^{23}SO_2R^{24}$, and $Cy^1$.

In a further aspect, $R^3$ is selected from —$CO_2R^{21}$, —$SO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, —$SO_2NR^{22a}R^{22b}$, —$NR^{23}SO_2R^{24}$, and $Cy^1$. In a still further aspect, $R^3$ is selected from —$SO_2R^{21}$, —$NR^{22a}R^{22b}$, —$CH_2NR^{22a}R^{22b}$, —$CH(CF_3)NR^{22a}R^{22b}$, —$SO_2NR^{22a}R^{22b}$, —$NR^{23}SO_2R^{24}$, and $Cy^1$. In yet a further aspect, $R^3$ is selected from —$NR^{22a}R^{22b}$, —$CH_2NR^{22a}R^{22b}$, —$CH(CF_3)NR^{22a}R^{22b}$, and $Cy^1$. In an even further aspect, $R^3$ is selected from —$CH(CF_3)NR^{22a}R^{22b}$ and $Cy^1$. In a still further aspect, $R^3$ is —$CH(CF_3)NR^{22a}R^{22b}$. In yet a further aspect, $R^3$ is $Cy^1$.

In a further aspect, $R^3$ is selected from —$C(F)=CHCH_3$, —$C(CN)=NOCH_3$, —$SO_2R^{21}$, —$NR^{22a}R^{22b}$, —$CH_2NR^{22a}R^{22b}$, —$CH(CF_3)NR^{22a}R^{22b}$, —$SO_2NR^{22a}R^{22b}$, —$NR^{23}SO_2R^{24}$, and $Cy^1$. In a still further aspect, $R^3$ is selected from —$C(F)=CHCH_3$, —$C(CN)=NOCH_3$, —$SO_2R^{21}$, —$NR^{22a}R^{22b}$, —$CH_2NR^{22a}R^{22b}$, —$SO_2NR^{22a}R^{22b}$, —$NR^{23}SO_2R^{24}$, and $Cy^1$. In an even further aspect, $R^3$ is selected from —$SO_2R^{21}$, —$SO_2NR^{22a}R^{22b}$, —$NR^{23}SO_2R^{24}$, and $Cy^1$. In a still further aspect, $R^3$ is selected from —$SO_2R^{21}$, —$SO_2NR^{22a}R^{22b}$, and —$NR^{23}SO_2R^{24}$. In yet a further aspect, $R^3$ is selected from —$SO_2R^{21}$, —$SO_2NR^{22a}R^{22b}$, and —$NR^{23}SO_2R^{24}$. In an even further aspect, $R^3$ is selected from —$SO_2R^{21}$ and —$SO_2NR^{22a}R^{22b}$. In a still further aspect, $R^3$ is —$SO_2R^{21}$. In yet a further aspect, $R^3$ is —$SO_2NR^{22a}R^{22b}$. In an even further aspect, $R^3$ is —$NR^{23}SO_2R^{24}$.

In a further aspect, $R^3$ is selected from —$C(F)=CHCH_3$, —$C(CN)=NOCH_3$, —$CO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, and $Cy^1$. In a still further aspect, $R^3$ is selected from —$C(F)=CHCH_3$, —$C(CN)=NOCH_3$, —$CO_2R^{21}$, —$NR^{22a}R^{22b}$, —$CH_2NR^{22a}R^{22b}$, —$C(O)NR^{22a}R^{22b}$, and $Cy^1$. In yet a further aspect, $R^3$ is selected from —$C(F)=CHCH_3$, —$C(CN)=NOCH_3$, —$CO_2R^{21}$, —$C(O)NR^{22a}R^{22b}$, and $Cy^1$. In an even further aspect, $R^3$ is selected from —$C(F)=CHCH_3$, —$C(CN)=NOCH_3$, and $Cy^1$. In a still further aspect, $R^3$ is selected from —$C(F)=CHCH_3$ and —$C(CN)=NOCH_3$. In yet a further aspect, $R^3$ is —$C(F)=CHCH_3$. In an even further aspect, $R^3$ is —$C(CN)=NOCH_3$.

In a further aspect, $R^3$ is selected from —$C(F)=CHCH_3$, —$C(CN)=NOCH_3$, —$CO_2R^{21}$, —$SO_2R^{21}$, —$NR^{22a}R^{22b}$, —$CH_2NR^{22a}R^{22b}$, —$C(O)NR^{22a}R^{22b}$, —$SO_2NR^{22a}R^{22b}$, —$NR^{23}SO_2R^{24}$, and $Cy^1$. In a still further aspect, $R^3$ is selected from —$CO_2R^{21}$, —$NR^{22a}R^{22b}$, —$CH_2NR^{22a}R^{22b}$, —$C(O)NR^{22a}R^{22b}$, and $Cy^1$. In yet a further aspect, $R^3$ is selected from —$CO_2R^{21}$, —$C(O)NR^{22a}R^{22b}$, and $Cy^1$. In an even further aspect, $R^3$ is selected from —$CO_2R^{21}$ and —$C(O)NR^{22a}R^{22b}$. In a still further aspect, $R^3$ is —$CO_2R^{21}$. In yet a further aspect, $R^3$ is —$C(O)NR^{22a}R^{22b}$ In a further aspect, $R^3$ is selected from —$C(F)=CHCH_3$, —$C(CN)=NOCH_3$, —$CO_2R^{21}$, —$SO_2R^{21}$, —$NR^{22a}R^{22b}$, —$CH_2NR^{22a}R^{22b}$, —$C(O)NR^{22a}R^{22b}$, —$CH(CF_3)NR^{22a}R^{22b}$, —$SO_2NR^{22a}R^{22b}$, and —$NR^{23}SO_2R^{24}$. In a still further aspect, $R^3$ is selected from —$C(F)=CHCH_3$, —$C(CN)=NOCH_3$, —$CO_2R^{21}$, —$SO_2R^{21}$, —$NR^{22a}R^{22b}$, —$CH_2NR^{22a}R^{22b}$, —$C(O)NR^{22a}R^{22b}$, —$SO_2NR^{22a}R^{22b}$, and —$NR^{23}SO_2R^{24}$. In yet a further aspect, $R^3$ is selected from —$CO_2R^{21}$, —$SO_2R^{21}$, —$NR^{22a}R^{22b}$, —$CH_2NR^{22a}R^{22b}$, —$C(O)NR^{22a}R^{22b}$, —$SO_2NR^{22a}R^{22b}$, and —$NR^{23}SO_2R^{24}$. In an even further aspect, $R^3$ is selected from —$CO_2R^{21}$, —$NR^{22a}R^{22b}$, —$CH_2NR^{22a}R^{22b}$, and —$C(O)NR^{22a}R^{22b}$. In a still further aspect, $R^3$ is selected from —$NR^{22a}R^{22b}$ and —$CH_2NR^{22a}R^{22b}$. In yet a further aspect, $R^3$ is —$NR^{22a}R^{22b}$. In an even further aspect, $R^3$ is —$CH_2NR^{22a}R^{22b}$.

d. $R^4$ Groups

In one aspect, each occurrence of $R^4$, when present, is independently selected from halogen, —$NH_2$, —$OH$, —$CN$, C1-C4 alkyl, C1-C4 haloalkyl, C1-C4 hydroxyalkyl, C1-C4 alkoxy, C1-C4 alkylamino, (C1-C4)(C1-C4) dialkylamino, —$C(F)=CHCH_3$, —$C(CN)=NOCH_3$, —$CO_2R^{31}$, —$SO_2R^{31}$, —$CO_2NR^{32a}R^{32b}$, —$CH(CF_3)NR^{32a}R^{32b}$, —$SO_2NR^{32a}R^{32b}$, —$NR^{33}SO_2R^{34}$, and $Cy^1$. In a further aspect, each occurrence of $R^4$, when present, is independently selected from —$F$, —$Cl$, —$NH_2$, —$OH$, —$CN$, methyl, ethyl, n-propyl, i-propyl, —$OCH_3$, —$OCH_2CH_3$, —$OCH_2CH_2CH_3$, —$OCH(CH_3)_2$, —$CH_2F$, —$CH_2CH_2F$, —$CH_2CH_2CH_2F$, —$CH(CH_3)CH_2F$, —$CH_2Cl$, —$CH_2CH_2Cl$, —$CH_2CH_2CH_2Cl$, —$CH(CH_3)CH_2Cl$, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In a still further aspect, each occurrence of R$^4$, when present, is independently selected from —F, —Cl, —NH$_2$, —OH, —CN, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, —N(CH$_3$)CH$_2$CH$_3$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In yet a further aspect, each occurrence of R$^4$, when present, is independently selected from —F, —Cl, —NH$_2$, —OH, —CN, methyl, —OCH$_3$, —CH$_2$F, —CH$_2$Cl, —CH$_2$OH, —NHCH$_3$, —N(CH$_3$)$_2$, C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$.

In a further aspect, each occurrence of R$^4$, when present, is independently selected from halogen, —NH$_2$, —OH, —CN, C1-C4 alkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In a still further aspect, each occurrence of R$^4$, when present, is independently selected from —F, —Cl, —NH$_2$, —OH, —CN, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$OH, —CH$_2$CH$_2$OH, —CH$_2$CH$_2$CH$_2$OH, CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, —C(F)=CHCH$_3$, C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In yet a further aspect, each occurrence of R$^4$, when present, is independently selected from —F, —Cl, —NH$_2$, —OH, —CN, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, —N(CH$_3$)CH$_2$CH$_3$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In an even further aspect, each occurrence of R$^4$, when present, is independently selected from —F, —Cl, —NH$_2$, —OH, —CN, methyl, —OCH$_3$, —CH$_2$OH, —NHCH$_3$, —N(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$.

In a further aspect, each occurrence of R$^4$, when present, is independently selected from halogen, —NH$_2$, —OH, —CN, C1-C4 alkyl, C1-C4 haloalkyl, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In a still further aspect, each occurrence of R$^4$, when present, is independently selected from —F, —Cl, —NH$_2$, —OH, —CN, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In yet a further aspect, each occurrence of R$^4$, when present, is independently selected from —F, —Cl, —NH$_2$, —OH, —CN, methyl, ethyl, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, —N(CH$_3$)CH$_2$CH$_3$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In an even further aspect, each occurrence of R$^4$, when present, is independently selected from —F, —Cl, —NH$_2$, —OH, —CN, methyl, —CH$_2$F, —CH$_2$Cl, —CH$_2$OH, —NHCH$_3$, —N(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$.

In a further aspect, each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In a still further aspect, each occurrence of R$^4$, when present, is independently selected from —F, —Cl, —NH$_2$, —OH, —CN, methyl, ethyl, n-propyl, i-propyl, —OCH$_3$, —OCH$_2$CH$_3$, OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In yet a further aspect, each occurrence of R$^4$, when present, is independently selected from —F, —Cl, —NH$_2$, —OH, —CN, methyl, ethyl, —OCH$_3$, —OCH$_2$CH$_3$, —CH$_2$F, —CH$_2$CH$_2$F, —CH$_2$Cl, —CH$_2$CH$_2$Cl, —NHCH$_3$, —NHCH$_2$CH$_3$, —N(CH$_3$)$_2$, —N(CH$_3$)CH$_2$CH$_3$, —C(F)=CHCH$_3$, —C(CN)=NOCH$_3$, —CO$_2$R$^{31}$, —SO$_2$R$^{31}$, —CO$_2$NR$^{32a}$R$^{32}$1, —CH(CF$_3$)NR$^{32a}$R$^{32b}$, —SO$_2$NR$^{32a}$R$^{32b}$, —NR$^{33}$SO$_2$R$^{34}$, and Cy$^1$. In an even further aspect, each occurrence of R$^4$, when present, is independently selected from —F, —Cl, —NH$_2$, —OH, —CN, methyl, —OCH$_3$, —CH$_2$F, —CH$_2$Cl, —NHCH$_3$, —N(CH$_3$)$_2$, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$.

In a further aspect, each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In a still further aspect, each occurrence of R$^4$, when present, is independently selected from —F, —Cl, —NH$_2$, —OH, —CN, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{14}$, and Cy$^1$. In yet a further aspect, each occurrence of R$^4$, when present, is independently selected from —F, —Cl, —NH$_2$, —OH, —CN, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$. In an even further aspect, each occurrence of R$^4$, when present, is independently selected from —F, —Cl, —NH$_2$, —OH, —CN, methyl, —OCH$_3$, —CH$_2$F, —CH$_2$Cl, —CH$_2$OH, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$.

In a further aspect, each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, and Cy$^1$. In a still further aspect, each occurrence of R$^4$, when present, is independently selected from —F, —Cl, —NH$_2$, —OH, —CN, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, and Cy$^1$. In yet a further aspect, each occurrence of R$^4$, when present, is independently selected from —F, —Cl, —NH$_2$, —OH, —CN, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, —N(CH$_3$)CH$_2$CH$_3$, and Cy$^1$. In an even further aspect, each occurrence of R$^4$, when present, is independently selected from —F, —Cl, —NH$_2$, —OH, —CN, methyl, —OCH$_3$, —CH$_2$F, —CH$_2$Cl, —CH$_2$OH, —NHCH$_3$, —N(CH$_3$)$_2$, and Cy$^1$.

e. R$^{21}$, R$^{22a}$, R$^{22b}$, R$^{23}$, and R$^{24}$ Groups

In one aspect, each of R$^{21}$, R$^{22a}$, R$^{22b}$, R$^{23}$, and R$^{24}$, when present, is independently selected from hydrogen, halogen, C1-C4 alkyl, C1-C4 alkoxy, C1-C4 haloalkyl, and Cy$^1$. In a further aspect, each of R$^{21}$, R$^{22a}$, R$^{22b}$, R$^{23}$, and R$^{24}$, when present, is hydrogen.

In a further aspect, each of R$^{21}$, R$^{22a}$, R$^{22b}$, R$^{23}$, and R$^{24}$, when present, is independently selected from hydrogen, —F, —Cl, C1-C4 alkyl, C1-C4 alkoxy, C1-C4 haloalkyl, and Cy$^1$. In a still further aspect, each of R$^{21}$, R$^{22a}$, R$^{22b}$, R$^{23}$, and R$^{24}$, when present, is independently selected from hydrogen, —Cl, —F, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, and Cy$^1$. In yet a further aspect, each of R$^{21}$, R$^{22a}$, R$^{22b}$, R$^{23}$, and R$^{24}$, when present, is independently selected from hydrogen, —Cl, —F, methyl, ethyl, —OCH$_3$, —OCH$_2$CH$_3$, —CH$_2$F, —CH$_2$CH$_2$F, —CH$_2$Cl, —CH$_2$CH$_2$Cl, and Cy$^1$. In an even further aspect, each of R$^{21}$, R$^{22a}$, R$^{22b}$, R$^{23}$, and R$^{24}$, when present, is independently selected from hydrogen, —Cl, —F, methyl, —OCH$_3$, —CH$_2$F, —CH$_2$Cl, and Cy$^1$.

In a further aspect, each of R$^{21}$, R$^{22a}$, R$^{22b}$, R$^{23}$, and R$^{24}$, when present, is independently selected from hydrogen, halogen, and C1-C4 alkyl. In a still further aspect, each of R$^{21}$, R$^{22a}$, R$^{22b}$, R$^{23}$, and R$^{24}$, when present, is independently selected from hydrogen, —Cl, —F, methyl, ethyl, n-propyl, and i-propyl. In yet a further aspect, each of R$^{21}$, R$^{22a}$, R$^{22b}$, R$^{23}$, and R$^{24}$, when present, is independently selected from hydrogen, —Cl, —F, methyl, and ethyl. In an even further aspect, each of R$^{21}$, R$^{22a}$, R$^{22b}$, R$^{23}$, and R$^{24}$, when present, is independently selected from hydrogen, —Cl, —F, and methyl.

In a further aspect, each of R$^{21}$, R$^{22a}$, R$^{22b}$, R$^{23}$, and R$^{24}$, when present, is independently selected from hydrogen, halogen, C1-C4 alkyl, C1-C4 haloalkyl, and Cy$^1$. In a still further aspect, each of R$^{21}$, R$^{22a}$, R$^{22b}$, R$^{23}$, and R$^{24}$, when present, is independently selected from hydrogen, —Cl, —F, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, and Cy$^1$. In yet a further aspect, each of R$^{21}$, R$^{22a}$, R$^{22b}$, R$^{23}$, and R$^{24}$, when present, is independently selected from hydrogen, —Cl, —F, methyl, ethyl, —CH$_2$F, —CH$_2$CH$_2$F, —CH$_2$Cl, —CH$_2$CH$_2$Cl, and Cy$^1$. In an even further aspect, each of R$^{21}$, R$^{22a}$, R$^{22b}$, R$^{23}$, and R$^{24}$, when present, is independently selected from hydrogen, —Cl, —F, methyl, —CH$_2$F, —CH$_2$Cl, and Cy$^1$.

In a further aspect, each of R$^{21}$, R$^{22a}$, R$^{22b}$, R$^{23}$, and R$^{24}$, when present, is independently selected from hydrogen, halogen, C1-C4 alkyl, C1-C4 alkoxy, and Cy$^1$. In a still further aspect, each of R$^{21}$, R$^{22a}$, R$^{22b}$, R$^{23}$, and R$^{24}$, when present, is independently selected from hydrogen, —Cl, —F, methyl, ethyl, n-propyl, i-propyl, —OCH$_3$, —OCH$_2$CH$_3$, —OCH$_2$CH$_2$CH$_3$, —OCH(CH$_3$)$_2$, and Cy$^1$. In yet a further aspect, each of R$^{21}$, R$^{22a}$, R$^{22b}$, R$^{23}$, and R$^{24}$, when present, is independently selected from hydrogen, —Cl, —F, methyl, ethyl, —OCH$_3$, —OCH$_2$CH$_3$, and Cy$^1$. In an even further aspect, each of R$^{21}$, R$^{22a}$, R$^{22b}$, R$^{23}$, and R$^{24}$, when present, is independently selected from hydrogen, —Cl, —F, methyl, —OCH$_3$, and Cy$^1$.

In a further aspect, each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and $Cy^1$.

In a further aspect, each of $R^{21}$, $R^{22a}$, $R^{22b}$, $R^{23}$, and $R^{24}$, when present, is independently selected from hydrogen, halogen, C1-C4 alkyl, C1-C4 haloalkyl, and $Cy^1$, provided that $R^{22a}$ and $R^{22b}$ are not simultaneously hydrogen.

In a further aspect, each of $R^{21}$, $R^{22a}$, $R^{22b}$, $R^{23}$, and $R^{24}$, when present, is independently selected from hydrogen and halogen. In a still further aspect, each of $R^{21}$, $R^{22a}$, $R^{22b}$, $R^{23}$, and $R^{24}$, when present, is independently selected from hydrogen, —Cl, —Br, and —F. In yet a further aspect, each of $R^{21}$, $R^{22a}$, $R^{22b}$, $R^{23}$, and $R^{24}$, when present, is independently selected from hydrogen, —Cl, and —F. In an even further aspect, each of $R^{21}$, $R^{22a}$, $R^{22b}$, $R^{23}$, and $R^{24}$, when present, is independently selected from hydrogen and —Cl. In a still further aspect, each of $R^{21}$, $R^{22a}$, $R^{22b}$, $R^{23}$, and $R^{24}$, when present, is independently selected from hydrogen and —F.

In a further aspect, In a further aspect, each of $R^{21}$, $R^{22a}$, $R^{22b}$, $R^{23}$, and $R^{24}$, when present, is independently selected from hydrogen and C1-C4 alkyl. In a still further aspect, each of $R^{21}$, $R^{22a}$, $R^{22b}$, $R^{23}$, and $R^{24}$, when present, is independently selected from hydrogen, methyl, ethyl, n-propyl, and i-propyl. In yet a further aspect, each of $R^{21}$, $R^{22a}$, $R^{22b}$, $R^{23}$, and $R^{24}$, when present, is independently selected from hydrogen, methyl, and ethyl. In an even further aspect, each of $R^{21}$, $R^{22a}$, $R^{22b}$, $R^{23}$, and $R^{24}$, when present, is independently selected from hydrogen and ethyl. In a still further aspect, each of $R^{21}$, $R^{22a}$, $R^{22b}$, $R^{23}$, and $R^{24}$, when present, is independently selected from hydrogen and methyl.

f. $R^{31}$, $R^{32a}$, $R^{32b}$, $R^{33}$, and $R^{34}$ Groups

In one aspect, each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and $Cy^1$. In a further aspect, each of $R^{31}$, $R^{32a}$, $R^{32b}$, $R^{33}$, and $R^{34}$, when present, is hydrogen.

In a further aspect, each of $R^{31}$, $R^{32a}$, $R^{32b}$, $R^{33}$, and $R^{34}$, when present, is independently selected from hydrogen, —F, —Cl, C1-C4 alkyl, C1-C4 alkoxy, C1-C4 haloalkyl, and $Cy^1$. In a still further aspect, each of $R^{31}$, $R^{32a}$, $R^{32b}$, $R^{33}$, and $R^{34}$, when present, is independently selected from hydrogen, —Cl, —F, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, and $Cy^1$. In yet a further aspect, each of $R^{31}$, $R^{32a}$, $R^{32b}$, $R^{33}$, and $R^{34}$, when present, is independently selected from hydrogen, —Cl, —F, methyl, ethyl, —OCH$_3$, —OCH$_2$CH$_3$, —CH$_2$F, —CH$_2$CH$_2$F, —CH$_2$Cl, —CH$_2$CH$_2$Cl, and $Cy^1$. In an even further aspect, each of $R^{31}$, $R^{32a}$, $R^{32b}$, $R^{33}$, and $R^{34}$, when present, is independently selected from hydrogen, —Cl, —F, methyl, —OCH$_3$, —CH$_2$F, —CH$_2$Cl, and $Cy^1$.

In a further aspect, each of $R^{31}$, $R^{32a}$, $R^{32b}$, $R^{33}$, and $R^{34}$, when present, is independently selected from hydrogen, halogen, and C1-C4 alkyl. In a still further aspect, each of $R^{31}$, $R^{32a}$, $R^{32b}$, $R^{33}$, and $R^{34}$, when present, is independently selected from hydrogen, —Cl, —F, methyl, ethyl, n-propyl, and i-propyl. In yet a further aspect, each of $R^{31}$, $R^{32a}$, $R^{32b}$, $R^{33}$, and $R^{34}$, when present, is independently selected from hydrogen, —Cl, —F, methyl, and ethyl. In an even further aspect, each of $R^{31}$, $R^{32a}$, $R^{32b}$, $R^{33}$, and $R^{34}$, when present, is independently selected from hydrogen, —Cl, —F, and methyl.

In a further aspect, each of $R^{31}$, $R^{32a}$, $R^{32b}$, $R^{33}$, and $R^{34}$, when present, is independently selected from hydrogen, halogen, C1-C4 alkyl, C1-C4 haloalkyl, and $Cy^1$. In a still further aspect, each of $R^{31}$, $R^{32a}$, $R^{32b}$, $R^{33}$, and $R^{34}$, when present, is independently selected from hydrogen, —Cl, —F, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, and $Cy^1$. In yet a further aspect, each of $R^{31}$, $R^{32a}$, $R^{32b}$, $R^{33}$, and $R^{34}$, when present, is independently selected from hydrogen, —Cl, —F, methyl, ethyl, —CH$_2$F, —CH$_2$CH$_2$F, —CH$_2$Cl, —CH$_2$CH$_2$Cl, and $Cy^1$. In an even further aspect, each of $R^{3i}$, $R^{32a}$, $R^{32b}$, $R^{33}$, and $R^{34}$, when present, is independently selected from hydrogen, —Cl, —F, methyl, —CH$_2$F, —CH$_2$Cl, and $Cy^1$.

In a further aspect, each of $R^{31}$, $R^{32a}$, $R^{32b}$, $R^{33}$, and $R^{34}$, when present, is independently selected from hydrogen, halogen, C1-C4 alkyl, C1-C4 alkoxy, and $Cy^1$. In a still further aspect, each of $R^{31}$, $R^{32a}$, $R^{32b}$, $R^{33}$, and $R^{34}$, when present, is independently selected from hydrogen, —Cl, —F, methyl, ethyl, n-propyl, i-propyl, —OCH$_3$, —OCH$_2$CH$_3$, —OCH$_2$CH$_2$CH$_3$, —OCH(CH$_3$)$_2$, and $Cy^1$. In yet a further aspect, each of $R^{31}$, $R^{32a}$, $R^{32b}$, $R^{33}$, and $R^{34}$, when present, is independently selected from hydrogen, —Cl, —F, methyl, ethyl, —OCH$_3$, —OCH$_2$CH$_3$, and $Cy^1$. In an even further aspect, each of $R^{31}$, $R^{32a}$, $R^{32b}$, $R^{33}$, and $R^{34}$, when present, is independently selected from hydrogen, —Cl, —F, methyl, —OCH$_3$, and $Cy^1$.

In a further aspect, each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and $Cy^1$.

In a further aspect, each of $R^{31}$, $R^{32a}$, $R^{32b}$, $R^{33}$, and $R^{34}$, when present, is independently selected from hydrogen and halogen, and C1-C4 alkyl. In a still further aspect, each of $R^{31}$, $R^{32a}$, $R^{32b}$, $R^{33}$, and $R^{34}$, when present, is independently selected from hydrogen, —Cl, —Br, and —F. In yet a further aspect, each of $R^{31}$, $R^{32a}$, $R^{32b}$, $R^{33}$, and $R^{34}$, when present, is independently selected from hydrogen, —Cl, and —F. In an even further aspect, each of $R^{31}$, $R^{32a}$, $R^{32b}$, $R^{33}$, and $R^{34}$, when present, is independently selected from hydrogen and —Cl. In a still further aspect, each of $R^{31}$, $R^{32a}$, $R^{32b}$, $R^{33}$, and $R^{34}$, when present, is independently selected from hydrogen and —F.

In a further aspect, In a further aspect, each of $R^{31}$, $R^{32a}$, $R^{32b}$, $R^{33}$, and $R^{34}$, when present, is independently selected from hydrogen and C1-C4 alkyl. In a still further aspect, each of $R^{31}$, $R^{32a}$, $R^{32b}$, $R^{33}$, and $R^{34}$, when present, is independently selected from hydrogen, methyl, ethyl, n-propyl, and i-propyl. In yet a further aspect, each of $R^{31}$, $R^{32a}$, $R^{32b}$, $R^3$, and $R^{34}$, when present, is independently selected from hydrogen, methyl, and ethyl. In an even further aspect, each of $R^{31}$, $R^{32a}$, $R^{32b}$, $R^{33}$, and $R^{34}$, when present, is independently selected from hydrogen and ethyl. In a still further aspect, each of $R^{31}$, $R^{32a}$, $R^{32b}$, $R^{33}$, and $R^{34}$, when present, is independently selected from hydrogen and methyl.

g. $R^{40a}$, $R^{40b}$, $R^{40c}$, $R^{40d}$, and $R^{40e}$

In one aspect, each of $R^{40a}$, $R^{40b}$, $R^{40c}$, $R^{40d}$, and $R^{40e}$ is independently selected from hydrogen, halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, each of $R^{40a}$, $R^{40b}$, $R^{40c}$, $R^{40d}$, and $R^{40e}$ is hydrogen.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, C1-C4 alkyl, C1-C4 alkoxy, C1-C4 haloalkyl, C1-C4 hydroxyalkyl, C1-C4 alkylamino, and (C1-C4)(C1-C4) dialkylamino. In a still further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, n-propyl, i-propyl, —OCH$_3$, OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, —OCH$_3$, —CH$_2$F, —CH$_2$Cl, —CH$_2$OH, —NHCH$_3$, and —N(CH$_3$)$_2$.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, C1-C4 alkyl, C1-C4 haloalkyl, C1-C4 hydroxyalkyl, C1-C4 alkylamino, and (C1-C4)(C1-C4) dialkylamino. In a still further aspect, each of $R^{40a}$, $R^{40b}R^{40c}$, $R^{40d}$, and $R^{40e}$ is independently selected from hydrogen, —Cl, —F, —CN, —NH$_2$, —OH, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, —CH$_2$F, —CH$_2$Cl, —CH$_2$OH, —NHCH$_3$, and —N(CH$_3$)$_2$.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, C1-C4 alkyl, C1-C4 alkoxy, C1-C4 hydroxyalkyl, C1-C4 alkylamino, and (C1-C4)(C1-C4) dialkylamino. In a still further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, —OCH$_3$, —OCH$_2$CH$_3$, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, —OCH$_3$, —CH$_2$OH, —NHCH$_3$, and —N(CH$_3$)$_2$.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, C1-C4 alkyl, C1-C4 alkoxy, C1-C4 haloalkyl, C1-C4 alkylamino, and (C1-C4)(C1-C4) dialkylamino. In a still further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, —OCH$_3$, —OCH$_2$CH$_3$, —CH$_2$F, —CH$_2$CH$_2$F, —CH$_2$Cl, —CH$_2$CH$_2$CT, —NHCH$_3$, —NHCH$_2$CH$_3$, —N(CH$_3$)$_2$, and —N(CH$_3$)CH$_2$CH$_3$. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, —OCH$_3$, —CH$_2$F, —CH$_2$Cl, —NHCH$_3$, and —N(CH$_3$)$_2$.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, C1-C4 alkyl, C1-C4 alkoxy, C1-C4 haloalkyl, and C1-C4 hydroxyalkyl. In a still further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, and —CH(CH$_3$)CH$_2$OH. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, and —CH$_2$CH$_2$OH. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, —OCH$_3$, —CH$_2$F, —CH$_2$Cl, and —CH$_2$OH.

In a further aspect, each of $R^{40a}$, $R^{40b}$, $R^{40c}$, $R^{40d}$, and $R^{40e}$ is independently selected from hydrogen, —F, —Cl, —CN, —NH$_2$, —OH, and C1-C4 alkyl. In a still further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, ethyl, n-propyl, and i-propyl. In yet a further aspect, each of $R^{40a}$, $R^{40b}$, $R^{40c}$, $R^{40d}$, and $R^{40e}$ is independently selected from hydrogen, —Cl, —F, —CN, —NH$_2$, —OH, methyl, and ethyl. In an even further aspect, each of $R^{40a}$, $R^{40b}$, $R^{40c}$, $R^{40d}$, and $R^{40e}$ is independently selected from hydrogen, —Cl, —F, —CN, —NH$_2$, —OH, and methyl.

In a further aspect, each of $R^{40a}$, $R^{40b}$, $R^{40c}$, $R^{40d}$, and $R^{40e}$ is independently selected from hydrogen, halogen, and C1-C4 alkyl. In a still further aspect, each of $R^{40a}$, $R^{40b}$, $R^{40c}$, $R^{40d}$, and $R^{40e}$ is independently selected from hydrogen, —Cl, —F, methyl, ethyl, n-propyl, and i-propyl. In yet a further aspect, each of $R^{40a}$, $R^{40b}$, $R^{40c}$, $R^{40d}$, and $R^{40e}$ is independently selected from hydrogen, —Cl, —F, methyl, and ethyl. In an even further aspect, each of $R^{40a}$, $R^{40b}$, $R^{40c}$, $R^{40d}$, and $R^{40e}$ is independently selected from hydrogen, —Cl, —F, and methyl.

In a further aspect, each of $R^{40a}$, $R^{40b}$, $R^{40c}$, $R^{40d}$, and $R^{40e}$ is independently selected from hydrogen and C1-C4 alkyl. In a still further aspect, each of $R^{40a}$, $R^{40b}$, $R^{40c}$, $R^{40d}$, and $R^{40e}$ is independently selected from hydrogen, methyl, ethyl, n-propyl, and i-propyl. In yet a further aspect, each of $R^{40a}$, $R^{40b}$, $R^{40}$, $R^{40d}$, and $R^{40e}$ is independently selected from hydrogen, methyl, and ethyl. In an even further aspect, each of $R^{40a}$, $R^{40b}$, $R^{40c}$, $R^{40d}$, and $R^{40e}$ is independently selected from hydrogen and methyl.

In a further aspect, each of $R^{40a}$, $R^{40b}$, $R^{40c}$, $R^{40d}$, and $R^{40e}$ is independently selected from hydrogen and halogen. In a still further aspect, each of $R^{40a}$, $R^{40b}$, $R^{40c}$, $R^{40d}$, and $R^{40e}$ is independently selected from hydrogen, —Cl, —F, and —Br. In yet a further aspect, each of $R^{40a}$, $R^{40b}$, $R^{40c}$, $R^{40d}$, and $R^{40e}$ is independently selected from hydrogen, —Cl, and —F. In an even further aspect, each of $R^{40a}$, $R^{40b}$, $R^{40c}$, $R^{40d}$, and $R^{40e}$ is independently selected from hydrogen and —Cl. In a still further aspect, each of $R^{40a}$, $R^{40b}$, $R^{40c}$, $R^{40d}$, and $R^{40e}$ is independently selected from hydrogen and —F.

In a further aspect, at least one of $R^{40a}$, $R^{40b}$, $R^{40c}$, $R^{40d}$, and $R^{40e}$ is halogen. In a still further aspect, at least one of $R^{40a}$, $R^{40b}$, $R^{40c}$, $R^{40d}$, and $R^{40e}$ is selected from —F, —Cl, and —Br. In yet a further aspect, at least one of $R^{40a}$, $R^{40b}$, $R^{40c}$, $R^{40d}$, and $R^{40e}$ is selected from F, and —Cl. In an even further aspect, at least one of $R^{40a}$, $R^{40b}$, $R^{40c}$, $R^{40d}$, and $R^{40e}$ is —F.

h. $R^{41a}$, $R^{41b}$, $R^{41c}$, $R^{41d}$, and $R^{41e}$ Groups

In one aspect, each of $R^{41a}$, $R^{41b}$, $R^{41c}$, $R^{41d}$, and $R^{41e}$, when present, is independently selected from hydrogen, halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, each of $R^{41a}$, $R^{41b}$, $R^{41c}$, $R^{41d}$, and $R^{41e}$, when present, is independently selected from hydrogen, —F, —Cl, —CN, —NH$_2$, —OH, C1-C4 alkyl, C1-C4 alkoxy, C1-C4 haloalkyl, C1-C4 hydroxyalkyl, C1-C4 alkylamino, and (C1-C4)(C1-C4) dialkylamino. In a still further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, —OCH$_3$, —OCH$_2$CH$_3$, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, —OCH$_3$, —CH$_2$F, —CH$_2$Cl, —CH$_2$OH, —NHCH$_3$, and —N(CH$_3$)$_2$.

In a further aspect, each of $R^{41a}$, $R^{41b}$, $R^{41c}$, $R^{41d}$, and $R^{41e}$, when present, is independently selected from hydrogen, —F, —Cl, —CN, —NH$_2$, —OH, C1-C4 haloalkyl, C1-C4 hydroxyalkyl, C1-C4 alkylamino, and (C1-C4)(C1-C4) dialkylamino. In a still further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{41}$, $R^{41b}$, $R^{41c}$, $R^{41d}$, and $R^{41e}$, when present, is independently selected from hydrogen, —Cl, —F, —CN, —NH$_2$, —OH, methyl, ethyl, —CH$_2$F, —CH$_2$CH$_2$F, —CH$_2$Cl, —CH$_2$CH$_2$Cl, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, —CH$_2$F, —CH$_2$Cl, —CH$_2$OH, —NHCH$_3$, and —N(CH$_3$)$_2$.

In a further aspect, each of $R^{41a}$, $R^{41b}$, $R^{41c}$, $R^{41d}$, and $R^{41e}$, when present, is independently selected from hydrogen, —F, —Cl, —CN, —NH$_2$, —OH, C1-C4 alkyl, C1-C4 alkoxy, C1-C4 hydroxyalkyl, C1-C4 alkylamino, and (C1-C4)(C1-C4) dialkylamino. In a still further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$OH, —CH$_2$CH$_2$OH, —CH$_2$CH$_2$CH$_2$OH, —CH(CH$_3$)CH$_2$OH, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{41}$, $R^{41b}$, $R^{41c}$, $R^{41d}$, and $R^{41e}$, when present, is independently selected from hydrogen, —Cl, —F, —CN, —NH$_2$, —OH, methyl, ethyl, —OCH$_3$, —OCH$_2$CH$_3$, —CH$_2$OH, —CH$_2$CH$_2$OH, —NHCH$_3$, —NHCH$_2$CH$_3$, —N(CH$_3$)$_2$, and —N(CH$_3$)CH$_2$CH$_3$. In an even further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, —OCH$_3$, —CH$_2$OH, —NHCH$_3$, and —N(CH$_3$)$_2$.

In a further aspect, each of $R^{41a}$, $R^{41b}$, $R^{41c}$, $R^{41d}$, and $R^{41e}$, when present, is independently selected from hydrogen, —F, —Cl, —CN, —NH$_2$, —OH, C1-C4 alkyl, C1-C4 alkoxy, C1-C4 haloalkyl, C1-C4 alkylamino, and (C1-C4) (C1-C4) dialkylamino. In a still further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, and —N(CH$_3$)CH(CH$_3$)$_2$. In yet a further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, —OCH$_3$, —OCH$_2$CH$_3$, —CH$_2$F, —CH$_2$CH$_2$F, —CH$_2$Cl, —CH$_2$CH$_2$Cl, —NHCH$_3$, —NHCH$_2$CH$_3$, —N(CH$_3$)$_2$, and —N(CH$_3$)CH$_2$CH$_3$. In an even further aspect, each of $R^{41a}$, $R^{41b}$, $R^{41c}$, $R^{41d}$, and $R^{41e}$, when present, is independently selected from hydrogen, —Cl, F, —CN, —NH$_2$, —OH, methyl, —OCH$_3$, —CH$_2$F, —CH$_2$Cl, —NHCH$_3$, and —N(CH$_3$)$_2$.

In a further aspect, each of $R^{41a}$, $R^{41b}$, $R^{41c}$, $R^{41d}$, and $R^{41e}$, when present, is independently selected from hydrogen, —F, —Cl, —CN, —NH$_2$, —OH, C1-C4 alkyl, C1-C4 alkoxy, C1-C4 haloalkyl, and C1-C4 hydroxyalkyl. In a still further aspect, each of $R^{41a}$, $R^{41b}$, $R^{41c}$, $R^{41d}$, and $R^{41e}$, when present, is independently selected from hydrogen, —Cl, —F, —CN, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)$_2$, —CH$_2$F, —CH$_2$CH$_2$F, —CH$_2$CH$_2$CH$_2$F, —CH (CH₃)CH₂F, —CH₂Cl, —CH₂CH₂Cl, —CH₂CH₂CH₂Cl, —CH(CH₃)CH₂Cl, —CH₂OH, —CH₂CH₂OH, —CH₂CH₂CH₂OH, and —CH(CH₃)CH₂OH. In yet a further aspect, each of $R^{41a}$, $R^{41b}$, $R^{41c}$, $R^{41d}$, and $R^{41e}$, when present, is independently selected from hydrogen, —Cl, —F, —CN, —NH₂, —OH, methyl, ethyl, —OCH₃, —OCH₂CH₃, —CH₂F, —CH₂CH₂F, —CH₂Cl, —CH₂CH₂Cl, —CH₂OH, and —CH₂CH₂OH. In an even further aspect, each of $R^{41a}$, $R^{41b}$, $R^{41c}$, $R^{41d}$, and $R^{41e}$, when present, is independently selected from hydrogen, —Cl, —F, —CN, —NH₂, —OH, methyl, OCH₃, —CH₂F, —CH₂Cl, and —CH₂OH.

In a further aspect, each of $R^{41a}$, $R^{41b}$, $R^{41c}$, $R^{41d}$, and $R^{41e}$, when present, is independently selected from hydrogen, —F, —Cl, —CN, —NH₂, —OH, and C1-C4 alkyl. In a still further aspect, each of $R^{41a}$, $R^{41b}$, $R^{41c}$, $R^{41d}$, and $R^{41e}$, when present, is independently selected from hydrogen, —Cl, —F, —CN, —NH₂, —OH, methyl, ethyl, n-propyl, and i-propyl. In yet a further aspect, each of $R^{41a}$, $R^{41b}$, $R^{41c}$, $R^{41d}$, and $R^{41e}$, when present, is independently selected from hydrogen, —Cl, —F, —CN, —NH₂, —OH, methyl, and ethyl. In an even further aspect, each of $R^{41a}$, $R^{41b}$, $R^{41c}$, $R^{41d}$, and $R^{41e}$, when present, is independently selected from hydrogen, —Cl, —F, —CN, —NH₂, —OH, and methyl.

In a further aspect, each of $R^{41a}$, $R^{41b}$, $R^{41c}$, $R^{41d}$, and $R^{41e}$, when present, is independently selected from hydrogen, halogen, and C1-C4 alkyl. In a still further aspect, each of $R^{41}$, $R^{41b}$, $R^{41c}$, $R^{41d}$, and $R^{41e}$, when present, is independently selected from hydrogen, —Cl, —F, methyl, ethyl, n-propyl, and i-propyl. In yet a further aspect, each of $R^{41a}$, $R^{41b}$, $R^{41c}$, $R^{41d}$, and $R^{41e}$, when present, is independently selected from hydrogen, —Cl, —F, methyl, and ethyl. In an even further aspect, each of $R^{41a}$, $R^{41b}$, $R^{41c}$, $R^{41d}$, and $R^{41e}$, when present, is independently selected from hydrogen, —Cl, —F, and methyl.

In a further aspect, each of $R^{41a}$, $R^{41b}$, $R^{41c}$, $R^{41d}$, and $R^{41e}$, when present, is independently selected from hydrogen and C1-C4 alkyl. In a still further aspect, each of $R^{41a}$, $R^{41b}$, $R^{41c}$, $R^{41d}$, and $R^{41e}$, when present, is independently selected from hydrogen, methyl, ethyl, n-propyl, and i-propyl. In yet a further aspect, each of $R^{4a}$, $R^{41b}$, $R^{41c}$, $R^{41d}$, and $R^{41e}$, when present, is independently selected from hydrogen, methyl, and ethyl. In an even further aspect, each of $R^{41a}$, $R^{41b}$, $R^{41c}$, $R^{41d}$, and $R^{41e}$, when present, is independently selected from hydrogen and methyl.

In a further aspect, each of $R^{41a}$, $R^{41b}$, $R^{41c}$, $R^{41d}$, and $R^{41e}$, when present, is independently selected from hydrogen and halogen. In a still further aspect, each of $R^{41a}$, $R^{41b}$, $R^{41c}$, $R^{41d}$, and $R^{41e}$, when present, is independently selected from hydrogen, —Cl, —F, and —Br. In yet a further aspect, each of $R^{41a}$, $R^{41b}$, $R^{41c}$, $R^{41d}$, and $R^{41e}$, when present, is independently selected from hydrogen, —Cl, and —F. In an even further aspect, each of $R^{41a}$, $R^{41b}$, $R^{41c}$, $R^{41d}$, and $R^{41e}$, when present, is independently selected from hydrogen and —Cl. In a still further aspect, each of $R^{41a}$, $R^{41b}$, $R^{41c}$, $R^{41d}$, and $R^{41e}$, when present, is independently selected from hydrogen and —F.

In a further aspect, each of $R^{41a}$, $R^{41b}$, $R^{41c}$, $R^{41d}$, and $R^{41e}$, when present, is hydrogen.

In a further aspect, one of $R^{41a}$, $R^{41b}$, $R^{41c}$, $R^{41d}$, and $R^{41e}$, when present, is halogen. In a still further aspect, one of $R^{41a}$, $R^{41b}$, $R^{41c}$, $R^{41d}$, and $R^{41e}$, when present, is —F.

In a further aspect, each of $R^{41b}$, $R^{41c}$, $R^{41d}$, and $R^{41e}$, when present, is hydrogen and wherein $R^{41a}$, when present, is halogen. In a still further aspect, each of $R^{41b}$, $R^{41c}$, $R^{41d}$, and $R^{41e}$, when present, is hydrogen and wherein $R^{41a}$, when present, is —F.

i. Cy¹ Groups

In one aspect, Cy¹, when present, is a structure having a formula selected from:

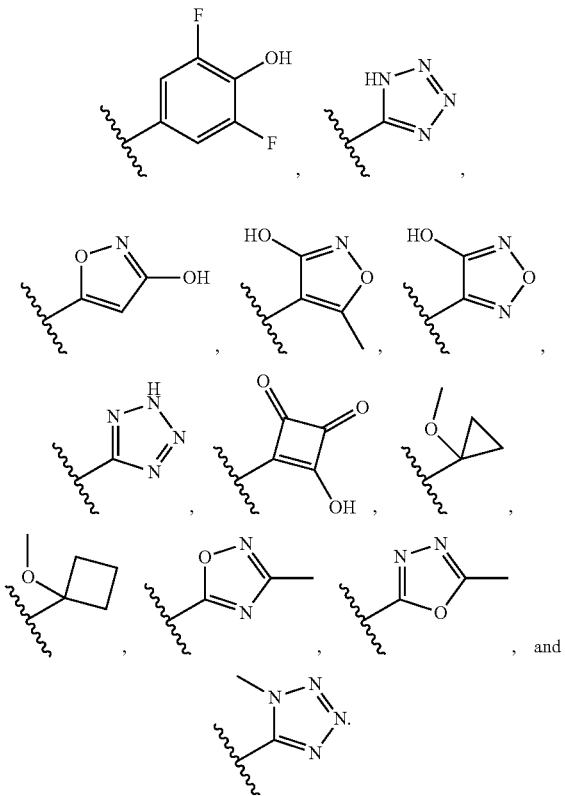

In a further aspect, Cy¹, when present, is a structure having a formula:

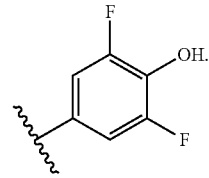 [SMILES: *c1cc(F)c(O)c(F)c1]

In a further aspect, Cy¹, when present, is a structure having a formula selected from:

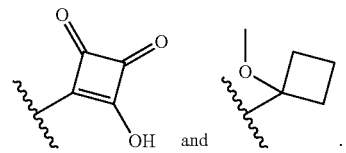

In a further aspect, Cy¹, when present, is a structure having a formula:

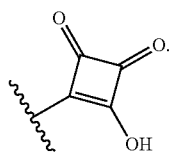 [SMILES: *c1c(O)c(=O)c1=O]

In a further aspect, Cy¹, when present, is a structure having a formula:

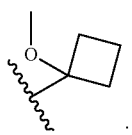

In a further aspect, Cy¹, when present, is a structure having a formula:

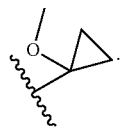 [SMILES: *C1(OC)CC1]

In a further aspect, Cy¹, when present, is a structure having a formula selected from:

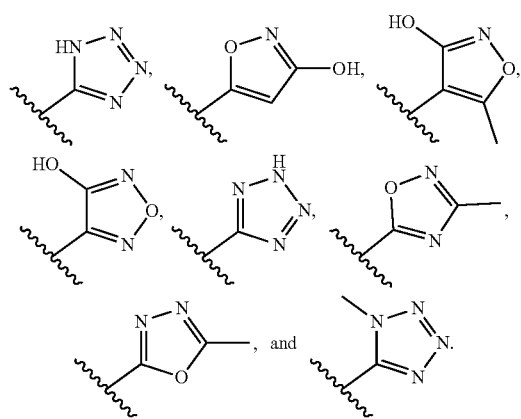

In a further aspect, Cy¹, when present, is a structure having a formula selected from:

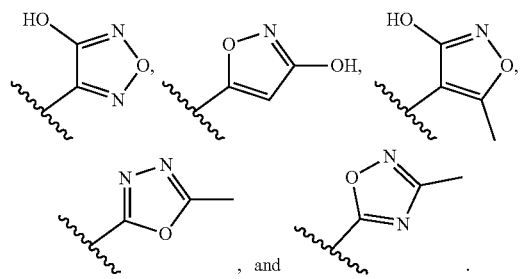

In a further aspect, Cy¹, when present, is a structure having a formula selected from:

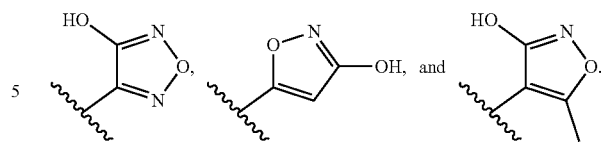

In a further aspect, Cy¹, when present, is a structure having a formula:

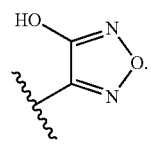 [SMILES: *c1nonc1O]

In a further aspect, Cy¹, when present, is a structure having a formula:

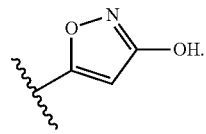 [SMILES: *c1cc(O)no1]

In a further aspect, Cy¹, when present, is a structure having a formula:

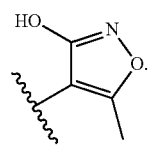 [SMILES: *c1c(O)noc1C]

In a further aspect, Cy¹, when present, is a structure having a formula selected from:

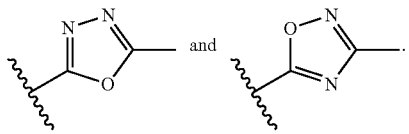

In a further aspect, Cy¹, when present, is a structure having a formula:

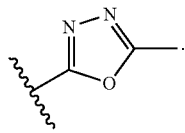

In a further aspect, Cy¹, when present, is a structure having a formula:

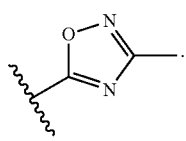

In a further aspect, $Cy^1$, when present, is a structure having a formula selected

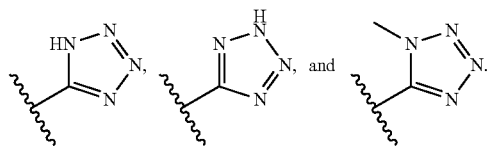

In a further aspect, $Cy^1$, when present, is a structure having a formula:

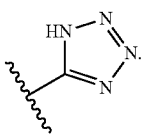 [SMILES: *c1nnn[nH]1]

In a further aspect, $Cy^1$, when present, is a structure having a formula:

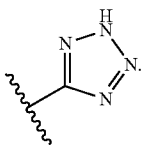 [SMILES: *c1nn[nH]n1]

In a further aspect, $Cy^1$, when present, is a structure having a formula:

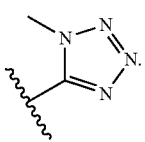 [SMILES: *c1nnnn1C]

j. $Ar^1$ Groups

In one aspect, $Ar^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Ar^1$ is selected from monocyclic aryl and pyridinyl, and is substituted with 0, 1, or 2 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Ar^1$ is selected from monocyclic aryl and pyridinyl, and is substituted with 0 or 1 group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Ar^1$ is selected from monocyclic aryl and pyridinyl, and is monosubstituted with a group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Ar^1$ is selected from monocyclic aryl and pyridinyl, and is unsubstituted.

In a further aspect, $Ar^1$ is monocyclic aryl substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Ar^1$ is monocyclic aryl substituted with 0, 1, or 2 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Ar^1$ is monocyclic aryl substituted with 0 or 1 group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Ar^1$ is monocyclic aryl monosubstituted with a group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Ar^1$ is unsubstituted monocyclic aryl.

In a further aspect, $Ar^1$ is pyridinyl substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Ar^1$ is pyridinyl substituted with 0, 1, or 2 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Ar^1$ is pyridinyl substituted with 0 or 1 group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Ar^1$ is pyridinyl monosubstituted with a group selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Ar^1$ is unsubstituted pyridinyl.

In a further aspect, $Ar^1$ is selected from monocyclic aryl and pyridinyl, and is substituted with 0, 1, 2, or 3 groups independently selected from halogen and C1-C4 haloalkyl.

In a further aspect, $Ar^1$ is monocyclic aryl substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $Ar^1$ is monocyclic aryl substituted with 1, 2, or 3 —F groups.

k. $Ar^2$ Groups

In one aspect, $Ar^2$, when present, is selected from monocyclic aryl and pyridinyl, and is substituted with 0, 1, or 2 independently selected $R^4$ groups. In a further aspect, $Ar^2$, when present, is selected from monocyclic aryl and pyridinyl, and is substituted with 0 or 1 $R^4$ group. In a still further aspect, $Ar^2$, when present, is selected from monocyclic aryl and pyridinyl, and is monosubstituted with a $R^4$ group. In yet a further aspect, $Ar^2$, when present, is selected from monocyclic aryl and pyridinyl, and is substituted with 0 $R^4$ groups.

In a further aspect, $Ar^2$, when present, is monocyclic aryl substituted with 0, 1, or 2 independently selected $R^4$ groups. In a still further aspect, $Ar^2$, when present, is monocyclic aryl substituted with 0 or 1 R⁴ group. In yet a further aspect, Ar², when present, is monocyclic aryl monosubstituted with a R⁴ group. In an even further aspect, Ar², when present, is monocyclic aryl substituted with 0 R⁴ groups.

In a further aspect, Ar², when present, is pyridinyl substituted with 0, 1, or 2 independently selected R⁴ groups. In a still further aspect, Ar², when present, is pyridinyl substituted with 0 or 1 R⁴ group. In yet a further aspect, Ar², when present, is pyridinyl monosubstituted with a R⁴ group. In an even further aspect, Ar², when present, is pyridinyl substituted with 0 R⁴ groups.

In a further aspect, Ar², when present, is monocyclic aryl substituted with 0, 1, or 2 independently selected R⁴ groups.

In a further aspect, Ar², when present, is 2-pyridinyl substituted with 0, 1, or 2 R⁴ groups, and wherein each occurrence of R⁴, when present, is independently selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Ar², when present, is 2-pyridinyl substituted with 0 or 1 R⁴ groups, and wherein R⁴, when present, is selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Ar², when present, is 2-pyridinyl monosubstituted with a R⁴ group, and wherein R⁴ is selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, Ar², when present, is 2-pyridinyl substituted with 0 R⁴ groups.

1. Ar³ Groups

In one aspect, Ar³, when present, is selected from monocyclic aryl and pyridinyl, and is substituted with 0, 1, 2, or 3 R⁴ groups. In a further aspect, Ar³, when present, is selected from monocyclic aryl and pyridinyl, and is substituted with 0 or 1 R⁴ group. In a still further aspect, Ar³, when present, is selected from monocyclic aryl and pyridinyl, and is monosubstituted with a R⁴ group. In yet a further aspect, Ar³, when present, is selected from monocyclic aryl and pyridinyl, and is substituted with 0 R⁴ groups.

In a further aspect, Ar³, when present, is monocyclic aryl substituted with 0, 1, or 2 independently selected R⁴ groups. In a still further aspect, Ar³, when present, is monocyclic aryl substituted with 0 or 1 R⁴ group. In yet a further aspect, Ar³, when present, is monocyclic aryl monosubstituted with a R⁴ group. In an even further aspect, Ar³, when present, is monocyclic aryl substituted with 0 R⁴ groups.

In a further aspect, Ar³, when present, is pyridinyl substituted with 0, 1, or 2 independently selected R⁴ groups. In a still further aspect, Ar³, when present, is pyridinyl substituted with 0 or 1 R⁴ group. In yet a further aspect, Ar³, when present, is pyridinyl monosubstituted with a R⁴ group. In an even further aspect, Ar³, when present, is pyridinyl substituted with 0 R⁴ groups.

In a further aspect, Ar³, when present, is monocyclic aryl substituted with 0, 1, or 2 independently selected R⁴ groups.

In a further aspect, Ar³, when present, is 2-pyridinyl substituted with 0, 1, or 2 R⁴ groups, and wherein each occurrence of R⁴, when present, is independently selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Ar³, when present, is 2-pyridinyl substituted with 0 or 1 R⁴ groups, and wherein R⁴, when present, is selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Ar³, when present, is 2-pyridinyl monosubstituted with a R⁴ group, and wherein R⁴ is selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, Ar³, when present, is 2-pyridinyl substituted with 0 R⁴ groups.

2. Example Compounds

In one aspect, a compound can be present as one or more of the following structures:

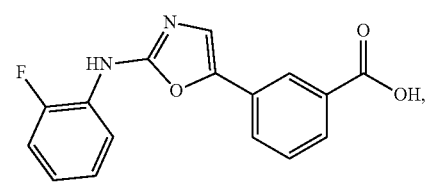

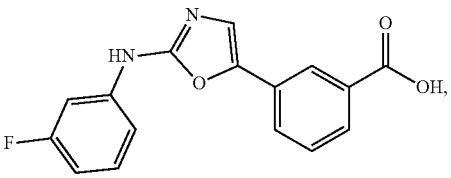

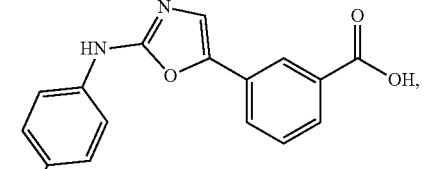

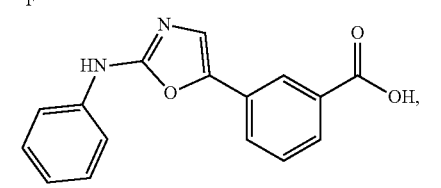

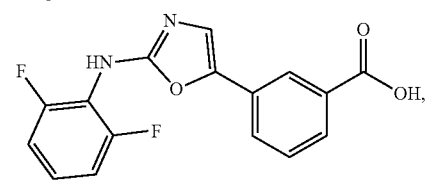

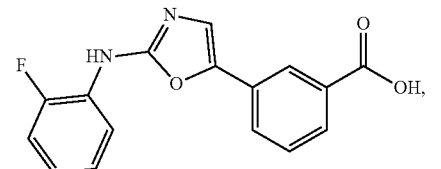

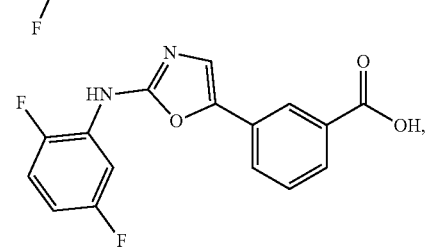

-continued
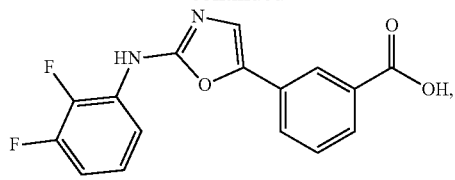
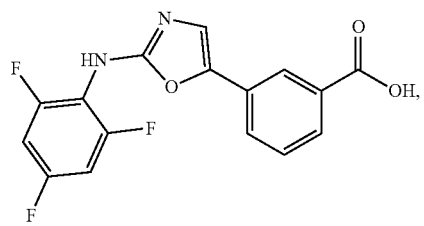
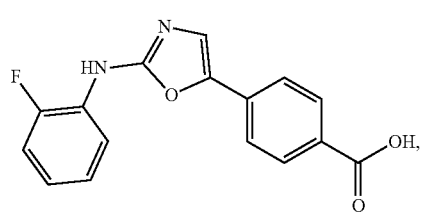
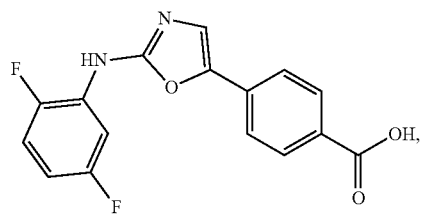
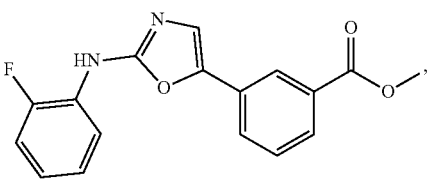
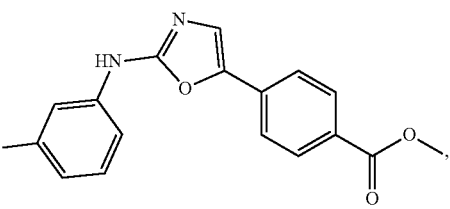
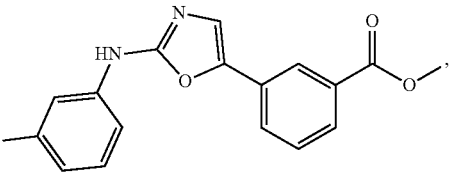
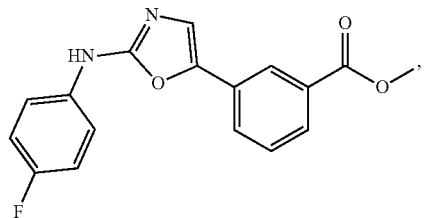
-continued
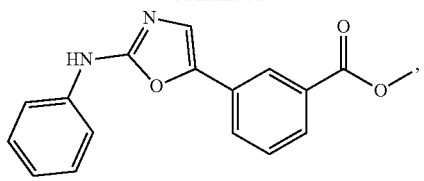
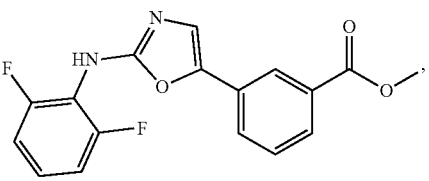
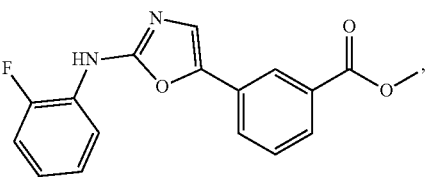
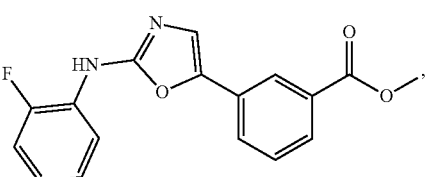
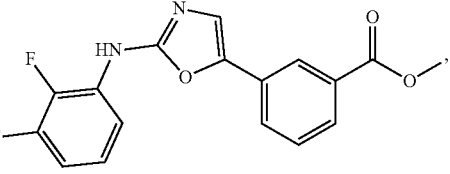
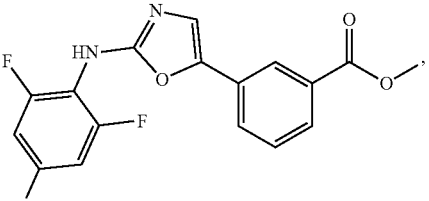
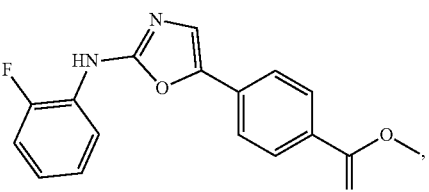
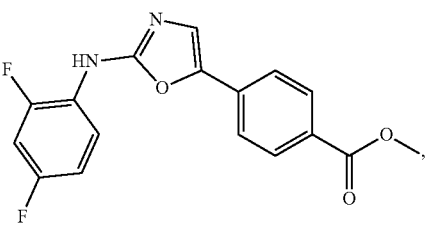

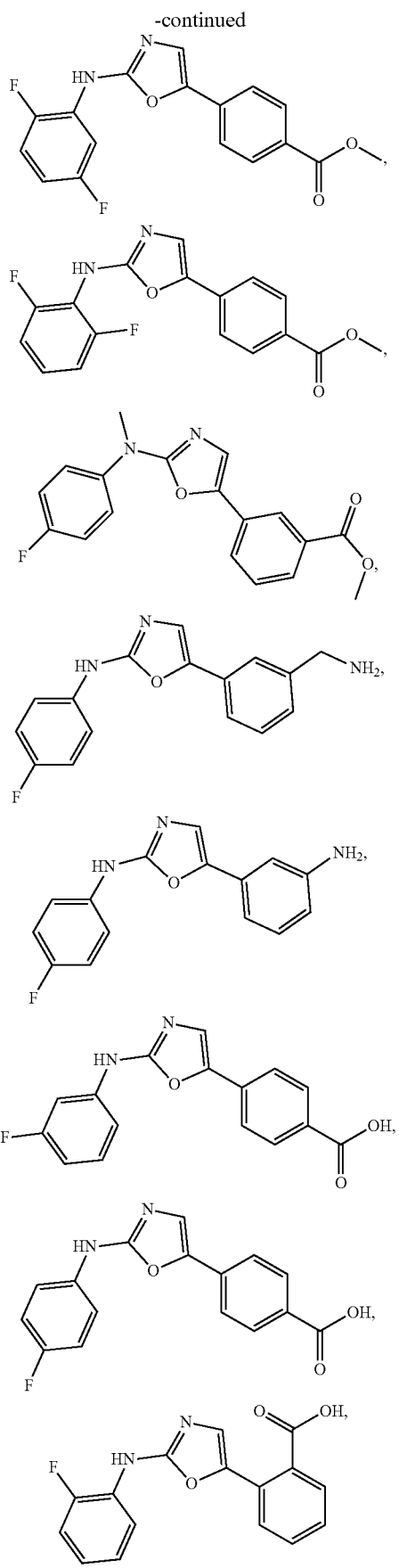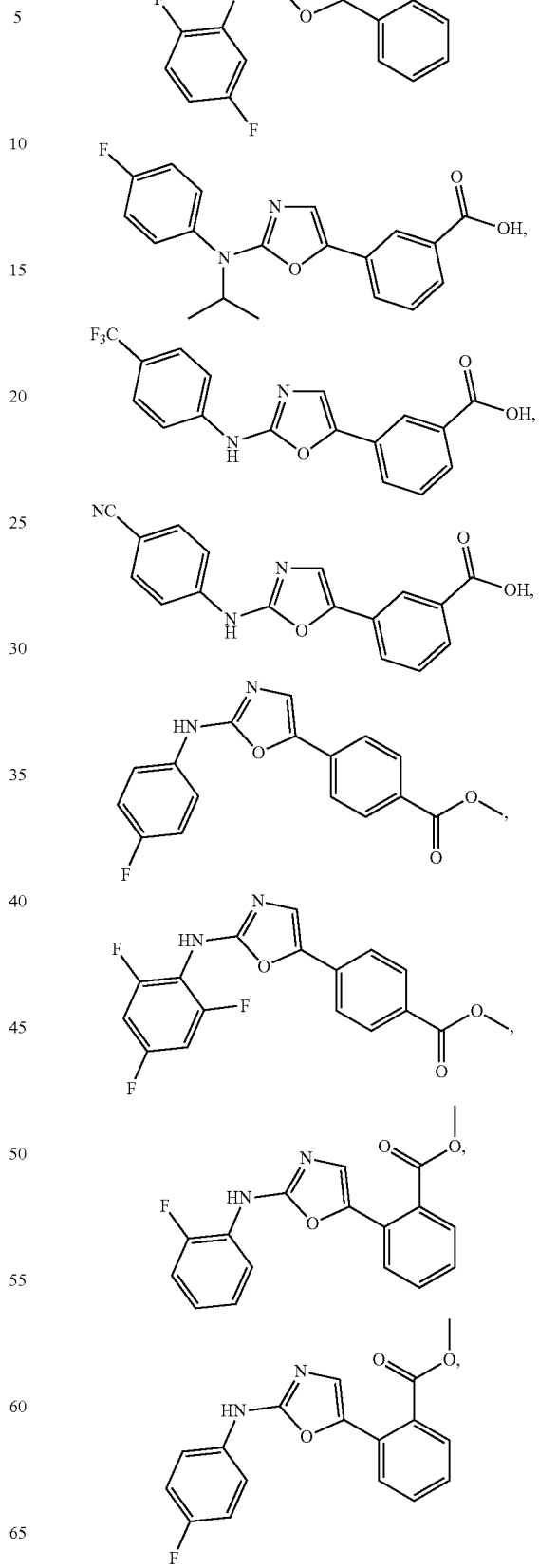

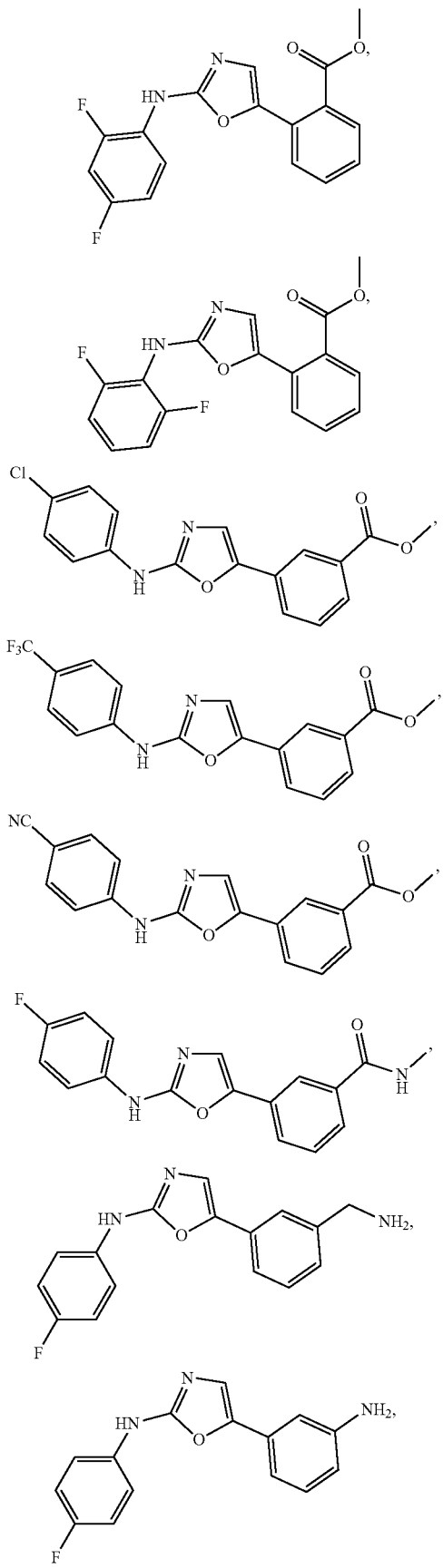
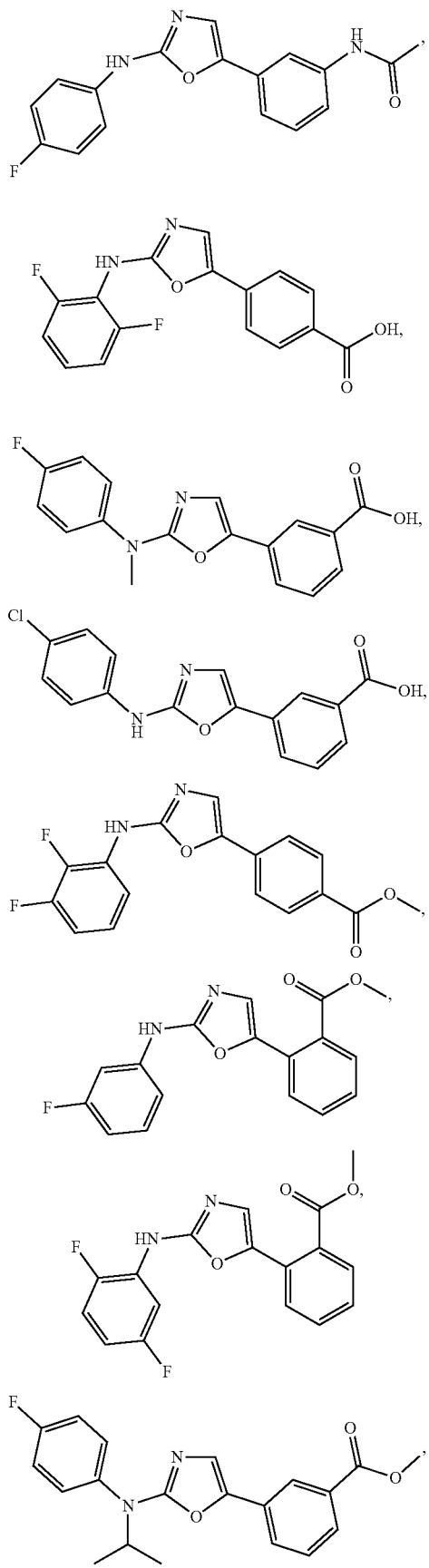

-continued

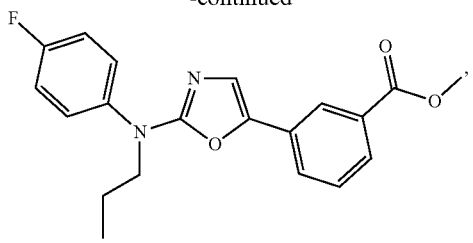

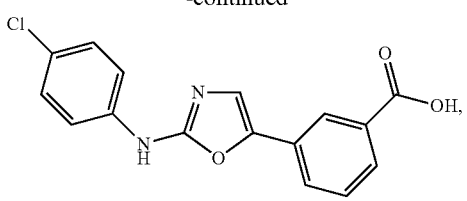

or a pharmaceutically acceptable salt thereof.

In one aspect, a compound can be present as one or more of the following structures:

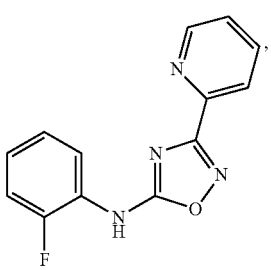 [SMILES: Fc1ccccc1Nc1nc(-c2ccccn2)no1]

or a pharmaceutically acceptable salt thereof.

In one aspect, a compound can be present as one or more of the following structures:

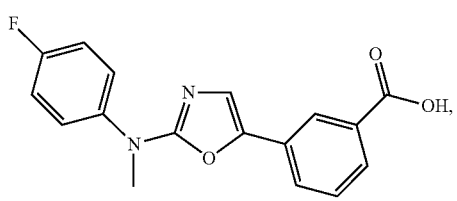

or a pharmaceutically acceptable salt thereof

3. Prophetic Compound Examples

The following compound examples are prophetic, and can be prepared using the synthesis methods described herein above and other general methods as needed as would be known to one skilled in the art. It is anticipated that the prophetic compounds would be active as NF-κB signaling, and such activity can be determined using the assay methods described herein below.

In one aspect, a compound can be selected from:
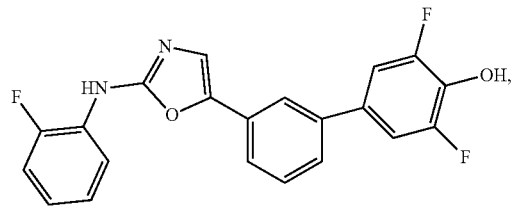
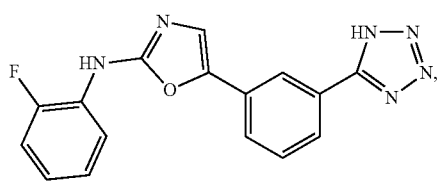
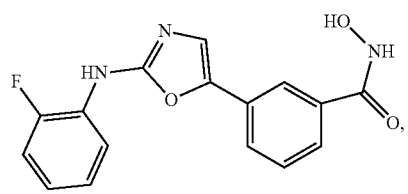
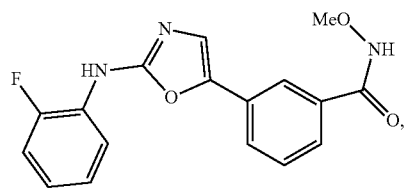
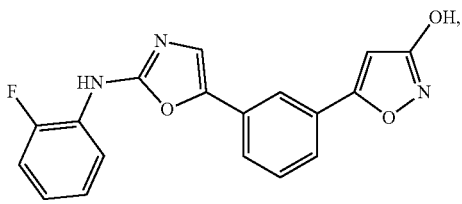
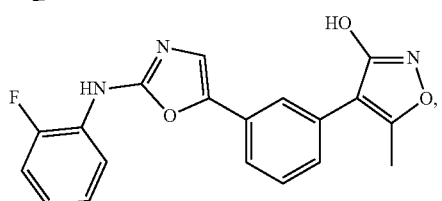
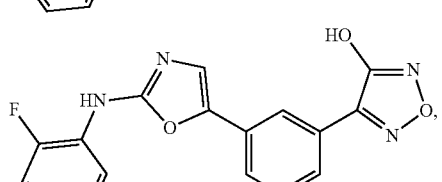
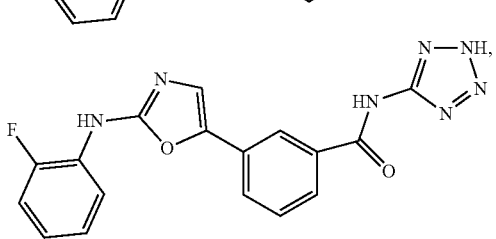
-continued
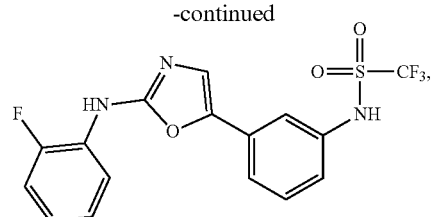
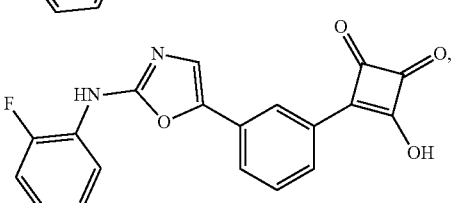
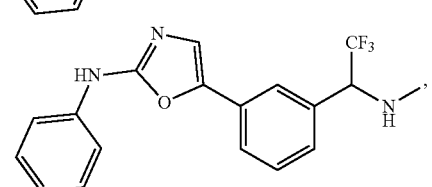
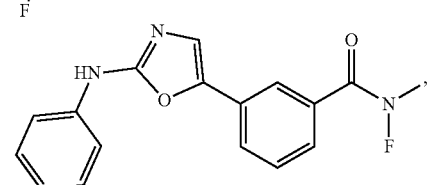
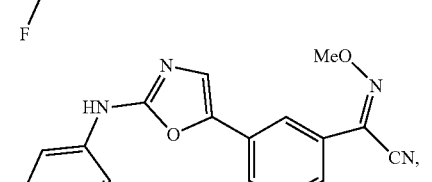
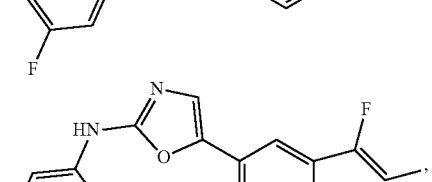

-continued

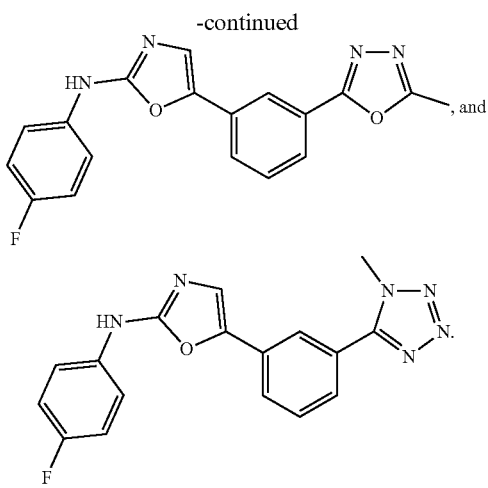

In one aspect, a compound can be selected from:

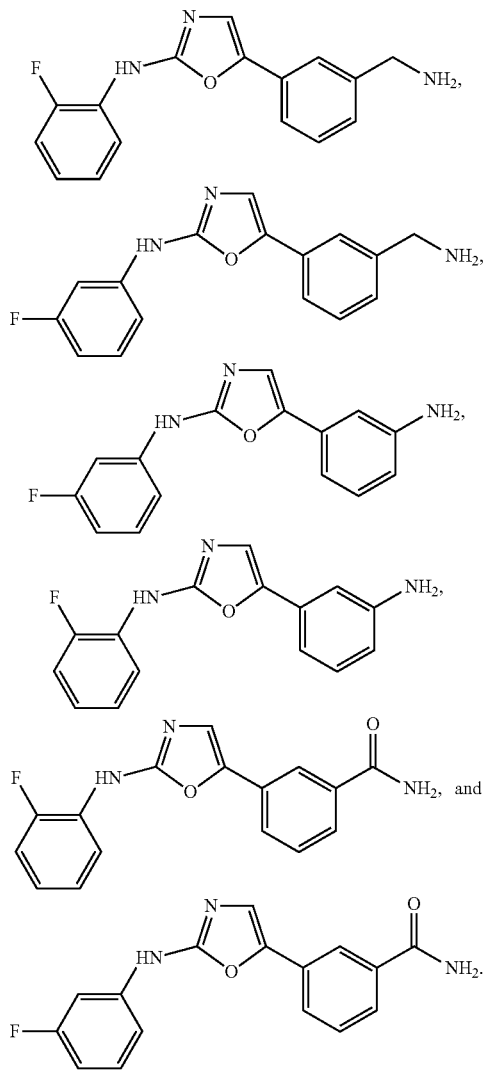

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising an effective amount of at least one compound having a structure represented by a formula selected from:

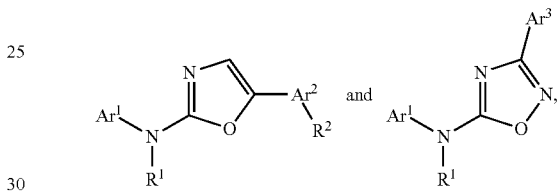

wherein $R^1$ is selected from hydrogen and C1-C4 alkyl; wherein $R^2$, when present, is selected from —C(F)=CHCH$_3$, —C(CN)=NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

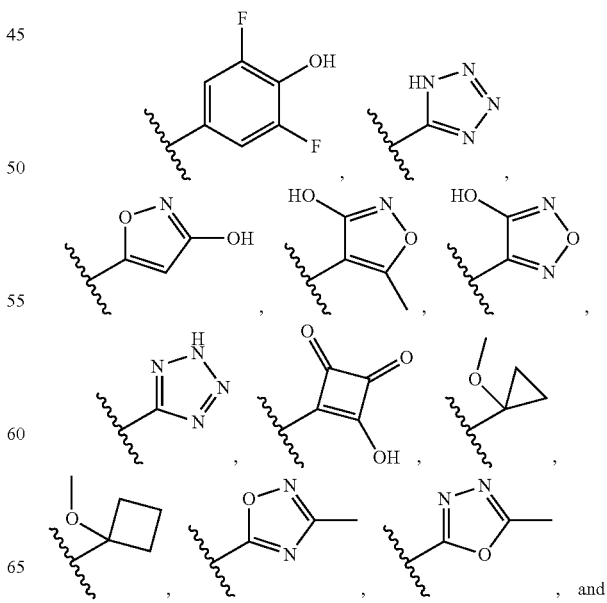

-continued

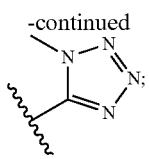

wherein $Ar^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^2$, when present, is selected from monocyclic aryl and pyridinyl, and is substituted with 0, 1, or 2 independently selected $R^4$ groups; wherein each occurrence of $R^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32}$, —CH(CF$_3$)NR$^{32a}$R$^{32b}$, —SO$_2$NR$^{32a}$R$^{32b}$, —NR$^{33}$SO$_2$R$^{34}$, and Cy$^1$; wherein each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and Cy$^1$; wherein $Ar^3$, when present, is selected from monocyclic aryl and pyridinyl, and is substituted with 0, 1, 2, or 3 $R^4$ groups; provided that when $R^1$ is hydrogen, $R^2$ is —CO$_2$H or —NH$_2$, and $Ar^2$ is monocyclic aryl, then $Ar^1$ is monocyclic aryl substituted with 1, 2, or 3 halogen groups or pyridinyl, and provided that either $Ar^3$ is pyridinyl or when $Ar^3$ is monocyclic aryl, $R^1$ is hydrogen, or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the externporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a neurological disorder such as, for example, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD). In a still further aspect, the pharmaceutical composition is used to treat ALS.

In a further aspect, the pharmaceutical composition is used to treat a neurological disorder is associated with dysregulation of NF-κB signaling. In a still further aspect, the pharmaceutical composition is used to treat a neurological disorder associated with activation of NF-κB signaling. In yet a further aspect, the pharmaceutical composition is used to treat a neurological disorder is associated with dysfunction of brain-derived neurotrophic factor.

It is understood that the disclosed compositions can be prepared from the disclosed compounds. It is also understood that the disclosed compositions can be employed in the disclosed methods of using.

D. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-IV, as described and exemplified below. The following examples are provided so that the invention might be more fully understood, are illustrative only, and should not be construed as limiting.

1. Route I

In one aspect, substituted 2,5-aryl-oxazole analogs can be prepared as shown below.

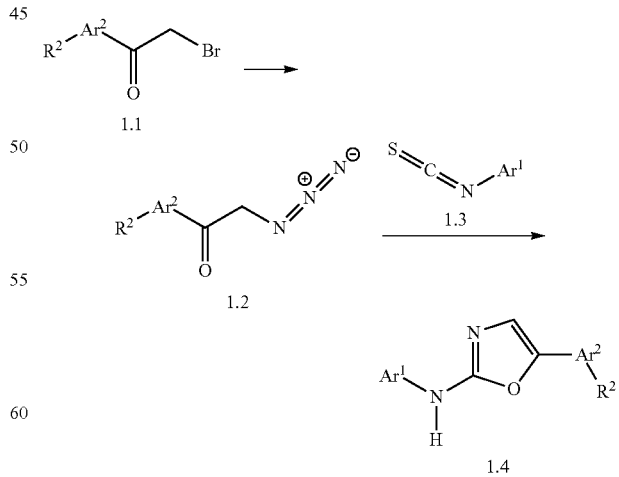

Compounds are represented in generic form, with substituents as noted in compound descriptions elsewhere herein. A more specific example is set forth below.

SCHEME 1B.

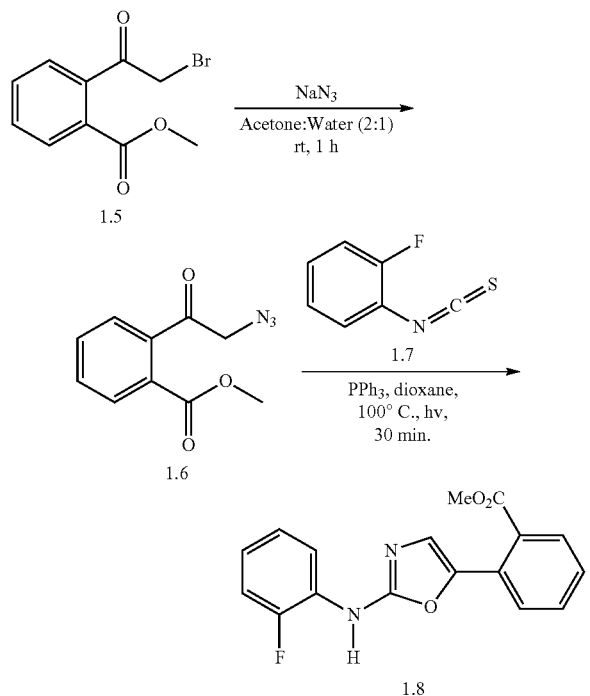

In one aspect, compounds of type 1.4, and similar compounds, can be prepared according to reaction Scheme 1B above. Thus, compounds of type 1.2 can be prepared by a substitution reaction of an appropriate α-haloketone, e.g., 1.1 as shown above. Appropriate α-haloketones are commercially available or prepared by methods known to one skilled in the art. The substitution reaction is carried out in the presence of an appropriate solvent system, e.g., acetone and water, for an appropriate period of time, e.g., 1 hour. Compounds of type 1.4 can be prepared by a cyclization reaction between an appropriate azide, e.g., 1.2 as shown above, and an appropriate isothiocyanate, e.g., 1.3 as shown above. Appropriate isothiocyanates are commercially available or prepared by methods known to one skilled in the art. The cyclization reaction is carried out in the presence of an appropriate nucleophile, e.g., triphenylphosphine, at an appropriate temperature, e.g., 100° C., for an appropriate period of time, e.g., 30 minutes. As can be appreciated by one skilled in the art, the above reaction provides an example of a generalized approach wherein compounds similar in structure to the specific reactants above (compounds similar to compounds of type 1.5, 1.6, and 1.7), can be substituted in the reaction to provide substituted 2,5-aryl-oxazoles similar to Formula 1.8.

2. Route II

In one aspect, substituted 2,5-aryl-oxazole analogs can be prepared as shown below.

SCHEME 2A.

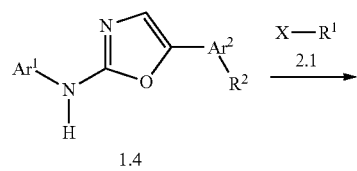

Compounds are represented in generic form, wherein X is halogen and with substituents as noted in compound descriptions elsewhere herein. A more specific example is set forth below.

SCHEME 2B.

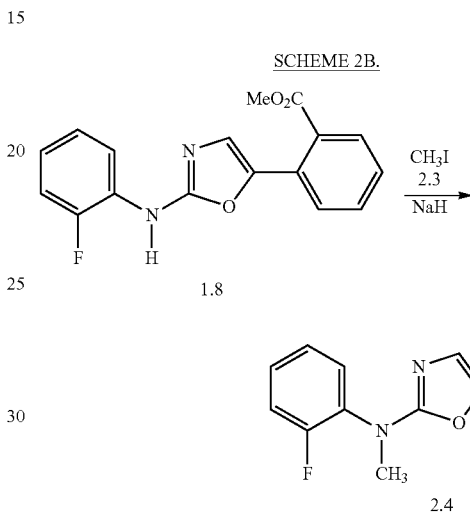

In one aspect, compounds of type 2.2, and similar compounds, can be prepared according to reaction Scheme 2B above. Thus, compounds of type 2.2 can be prepared by an alkylation reaction between an appropriate amine, e.g., 1.4 as shown above, and an appropriate alkyl halide, e.g., 2.1 as shown above. Appropriate alkyl halides are commercially available or prepared by methods known to one skilled in the art. The alkylation reaction is carried out in the presence of an appropriate base, e.g., sodium hydride. As can be appreciated by one skilled in the art, the above reaction provides an example of a generalized approach wherein compounds similar in structure to the specific reactants above (compounds similar to compounds of type 1.8 and 2.3), can be substituted in the reaction to provide substituted 2,5-aryl-oxazoles similar to Formula 2.4.

3. Route III

In one aspect, substituted 2,5-aryl-oxazole analogs can be prepared as shown below.

SCHEME 3A.

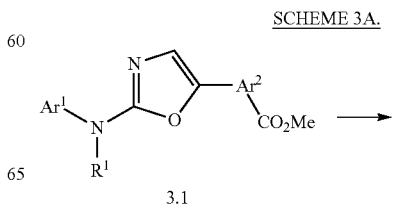

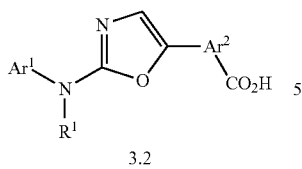

3.2

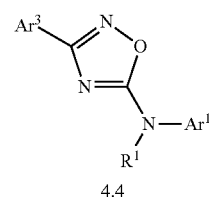

4.4

Compounds are represented in generic form, with substituents as noted in compound descriptions elsewhere herein. A more specific example is set forth below.

Compounds are represented in generic form, with substituents as noted in compound descriptions elsewhere herein. A more specific example is set forth below.

SCHEME 3B.

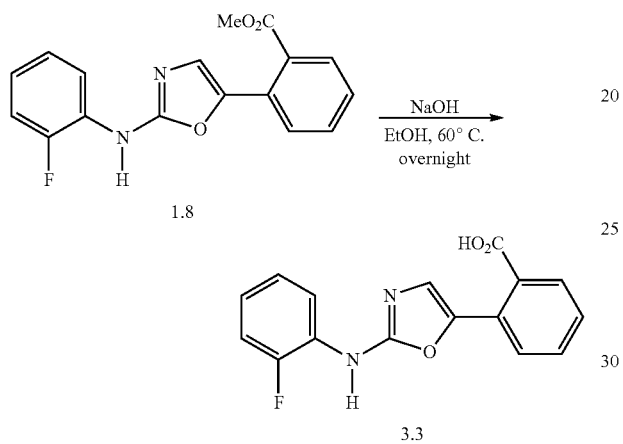

SCHEME 4B.

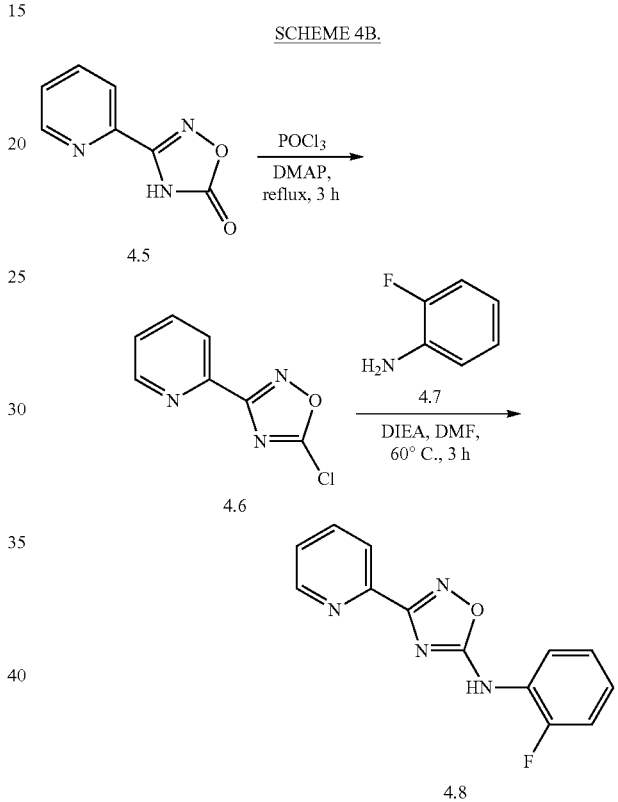

In one aspect, compounds of type 3.2, and similar compounds, can be prepared according to reaction Scheme 3B above. Thus, compounds of type 3.2 can be prepared by saponification of an appropriate ester, e.g., 3.1 as shown above. The saponification is carried out in the presence of an appropriate base, e.g., sodium hydroxide, in an appropriate solvent, e.g., ethanol, at an appropriate temperature, e.g., 60° C. As can be appreciated by one skilled in the art, the above reaction provides an example of a generalized approach wherein compounds similar in structure to the specific reactants above (compounds similar to compounds of type 1.8), can be substituted in the reaction to provide substituted 2,5-aryl-oxazoles similar to Formula 3.3.

4. Route IV

In one aspect, substituted diaryl-oxadiazole analogs can be prepared as shown below.

SCHEME 4A.

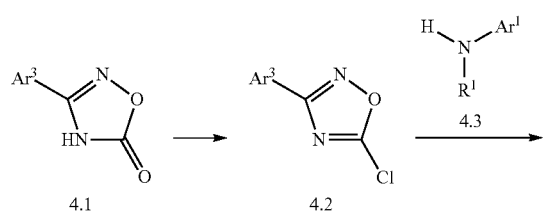

In one aspect, compounds of type 4.4, and similar compounds, can be prepared according to reaction Scheme 4B above. Thus, compounds of type 4.2 can be prepared by halogenation of an appropriate oxadiazolone, e.g., 4.1 as shown above. Appropriate oxadiazolones are commercially available or prepared by methods known to one skilled in the art. The halogenation is carried out in the presence of an appropriate halide source, e.g., phosphorous oxychloride, and an appropriate base, e.g., 4-dimethylaminopyridine, for an appropriate period of time, e.g., 3 hours. Compounds of type 4.4 can be prepared by a substitution reaction between an appropriate halide, e.g., 4.2 as shown above, and an appropriate amine, e.g., 4.3 as shown above. Appropriate amines are commercially available or prepared by methods known to one skilled in the art. The substitution reaction is carried out in the presence of an appropriate base, e.g., N,N-diisopropylethylamine, in an appropriate solvent, e.g., dimethylformamide, at an appropriate temperature, e.g., 60° C., for an appropriate period of time, e.g., 3 hours. As can be appreciated by one skilled in the art, the above reaction provides an example of a generalized approach wherein compounds similar in structure to the specific reactants above (compounds similar to compounds of type 4.5, 4.6, and 4.7), can be substituted in the reaction to provide substituted diaryl-oxadiazoles similar to Formula 4.8.

E. Methods of Using the Compounds

The compounds and pharmaceutical compositions of the invention are useful in treating or controlling disorders associated with neurological disorders and in particular, ALS, and neuromuscular disorders, in particular, Duchenne muscular dystrophy (DMD).

Examples of neurological disorders for which the compounds and compositions can be useful in treating, include, but are not limited to, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD).

Examples of neuromuscular disorders for which the compounds and compositions can be useful in treating, include, but are not limited to, Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, oculopharyngeal muscular dystrophy, amyotrophic lateral sclerosis, infantile progressive spinal muscular atrophy, intermediate spinal muscular atrophy, juvenile spinal muscular atrophy, adult spinal muscular atrophy, dermatomyositis, polymyositis, inclusion body myositis, Chocot-Marie tooth disease, Dejerine-Sottas disease, Friedreich's ataxia, Myasthenia gravis, Lambert-Eaton syndrome, botulism, acid maltase deficiency, carnitine deficiency, camitine palmityl transferase deficiency, debrancher enzyme deficiency, lactate dehydrogenase deficiency, mitochondrial myopathy, myoadenylate deaminase deficiency, phosphorylase deficiency, phosphofructokinase deficiency, phosphoglycerate kinase deficiency, central core disease, hyperthyroid myopathy, myotonia congenital, myotubular myopathy, nemaline myopathy, paramyotonia congenital, and periodic paralysis-hypokalemic-hyperkalemic.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a neurological disorder, such as ALS, and/or a need for treatment of a neuromuscular disorder, such as DMD.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a neurological disorder, such as ALS, and/or for prevention of a neuromuscular disorder, such as DMD.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with a neurological disorder, in particular, ALS, and/or associated with a neuromuscular disorder, such as DMD. Thus, provided is a method comprising administering a therapeutically effective amount of a composition comprising a disclosed compound to a subject. In a further aspect, the method can be a method for treating a neurological disorder. In a still further aspect, the method can be a method for treating a neuromuscular disorder.

a. Treating a Neurological Disorder

In one aspect, disclosed are methods of treating a neurological disorder in a subject having the neurological disorder, the method comprising the step of administering to the subject a therapeutically effective amount of at least one disclosed compound, or a pharmaceutically acceptable salt thereof.

In one aspect, disclosed are methods for the treatment of a neurological disorder in a subject, the method comprising the step of administering to the subject an effective amount of at least one compound having a structure represented by a formula selected from:

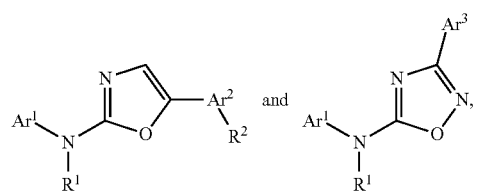

wherein $R^1$ is selected from hydrogen and C1-C4 alkyl; wherein $R^2$, when present, is selected from —C(F)=CHCH$_3$, —C(CN)=NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and $Cy^1$; wherein $Cy^1$, when present, is a structure having a formula selected from:

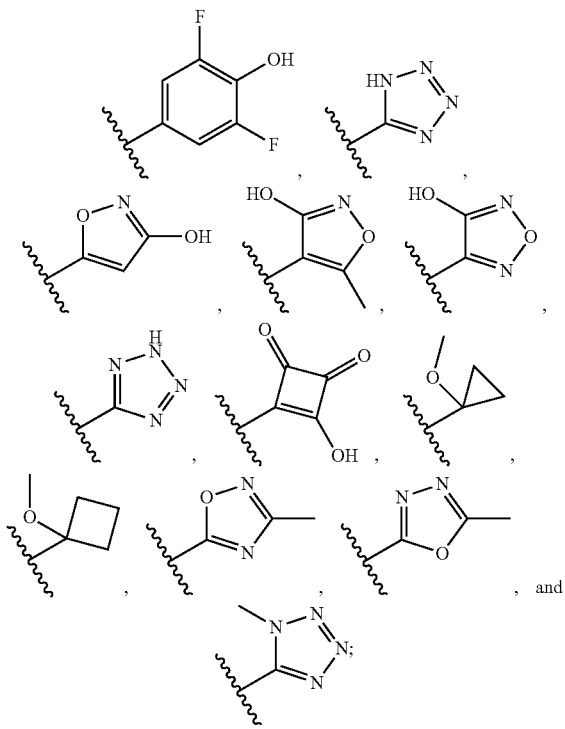

wherein $Ar^1$ is selected from monocyclic aryl and pyridinyl, and is substituted with 0, 1, 2, or 3 groups independently selected from halogen, —CN, —$NH_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^2$, when present, is selected from monocyclic aryl and pyridinyl, and is substituted with 0, 1, or 2 independently selected $R^4$ groups; wherein each occurrence of $R^4$, when present, is independently selected from halogen, —$NH_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=$CHCH_3$, —C(CN)=$NOCH_3$, —$CO_2R^{31}$, —$SO_2R^{31}$, —$CO_2NR^{32a}R^{32b}$, —CH($CF_3$)$NR^{32a}R^{32b}$, —$SO_2NR^{32a}R^{32b}$, —$NR^{33}SO_2R^{34}$, and $Cy^1$; wherein each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and $Cy^1$; wherein $Ar^3$, when present, is selected from monocyclic aryl and pyridinyl, and is substituted with 0, 1, 2, or 3 $R^4$ groups; provided that when $R^1$ is hydrogen, $R^2$ is —$CO_2H$ or —$NH_2$, and $Ar^2$ is monocyclic aryl, then $Ar^1$ is monocyclic aryl substituted with 1, 2, or 3 halogen groups or pyridinyl, and provided that either $Ar^3$ is pyridinyl or when $Ar^3$ is monocyclic aryl, $R^1$ is hydrogen, or a pharmaceutically acceptable salt thereof.

Examples of neurological disorders include, but are not limited to, amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD).

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the neurological disorder.

In a further aspect, the disorder is associated with dysregulation of NF-κB signaling. In a still further aspect, the neurological disorder is associated with activation of NF-κB signaling. In yet a further aspect, the neurological disorder is associated with dysfunction of brain-derived neurotrophic factor.

In a further aspect, the neurological disorder is selected from amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD). In yet a further aspect, the neurological disorder is ALS.

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a neurological disorder. In a still further aspect, the at least one agent is selected from cholinesterase inhibitor, an antidepressant, memantine, rilutek, radicava, levodopa, carbidopa, a dopamine agonist, a MAO-B inhibitor, a catechol-O-methyltransferase inhibitor, an anticholinergic, spinraza, tetrabenazine, an antipsychotic agent, levetiracetam, clonazepam, an antipsychotic agent, a mood-stabilizing agent, and amantadine.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

b. Treating a Neuromuscular Disorder

In one aspect, disclosed are methods of treating a neuromuscular disorder in a subject having the neuromuscular disorder, the method comprising the step of administering to the subject a therapeutically effective amount of at least one disclosed compound, or a pharmaceutically acceptable salt thereof.

In one aspect, disclosed are methods for the treatment of a neuromuscular disorder in a subject, the method comprising the step of administering to the subject an effective amount of at least one compound having a structure represented by a formula selected from:

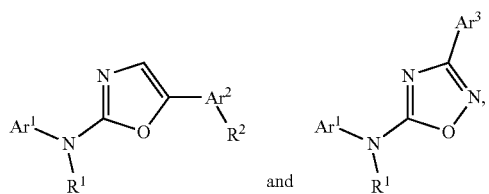

wherein $R^1$ is selected from hydrogen and C1-C4 alkyl; wherein $R^2$, when present, is selected from —C(F)=$CHCH_3$, —C(CN)=$NOCH_3$, —$CO_2R^{21}$, —$SO_2R^{21}$, —$NR^{22a}R^{22b}$, —$CH_2NR^{22a}R^{22b}$, —C(O)$NR^{22a}R^{22b}$, —CH (CF$_3$)NR$^{22a}$R$^{22b}$, —SO$_2$NR$^{22a}$R$^{22b}$, —NR$^{23}$SO$_2$R$^{24}$, and Cy$^1$; wherein each of R$^{21}$, R$^{22a}$, R$^{22b}$, R$^{23}$, and R$^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

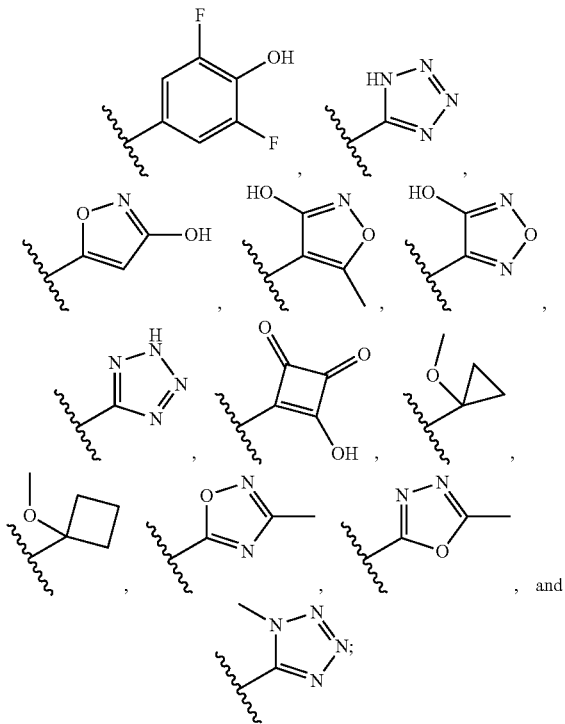

wherein Ar$^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^2$, when present, is selected from monocyclic aryl and pyridinyl, and is substituted with 0, 1, or 2 independently selected R$^4$ groups; wherein each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN) =NOCH$_3$, —CO$_2$R$^{31}$, —SO$_2$R$^{31}$, —CO$_2$NR$^{32a}$R$^{32b}$, —CH (CF$_3$)NR$^{32a}$R$^{32b}$, —SO$_2$NR$^{32a}$R$^{32b}$, —NR$^{33}$SO$_2$R$^{34}$, and Cy$^1$; wherein each of R$^{31}$, R$^{32a}$, R$^{32b}$, R$^{33}$, and R$^{34}$, when present, is independently selected from hydrogen, halogen, C1-C4 alkyl, C1-C4 alkoxy, C1-C4 haloalkyl, and Cy$^1$; wherein Ar$^3$, when present, is selected from monocyclic aryl and pyridinyl, and is substituted with 0, 1, 2, or 3 R$^4$ groups; provided that when R$^1$ is hydrogen, R$^2$ is —CO$_2$H or —NH$_2$, and Ar$^2$ is monocyclic aryl, then Ar$^1$ is monocyclic aryl substituted with 1, 2, or 3 halogen groups or pyridinyl, and provided that either Ar$^3$ is pyridinyl or when Ar$^3$ is monocyclic aryl, R$^1$ is hydrogen, or a pharmaceutically acceptable salt thereof.

Examples of neuromuscular disorders include, but are not limited to, Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, oculopharyngeal muscular dystrophy, amyotrophic lateral sclerosis, infantile progressive spinal muscular atrophy, intermediate spinal muscular atrophy, juvenile spinal muscular atrophy, adult spinal muscular atrophy, dermatomyositis, polymyositis, inclusion body myositis, Chocot-Marie tooth disease, Dejerine-Sottas disease, Friedreich's ataxia, Myasthenia gravis, Lambert-Eaton syndrome, botulism, acid maltase deficiency, carnitine deficiency, camitine palmityl transferase deficiency, debrancher enzyme deficiency, lactate dehydrogenase deficiency, mitochondrial myopathy, myoadenylate deaminase deficiency, phosphorylase deficiency, phosphofructokinase deficiency, phosphoglycerate kinase deficiency, central core disease, hyperthyroid myopathy, myotonia congenital, myotubular myopathy, nemaline myopathy, paramyotonia congenital, and periodic paralysis-hypokalemic-hyperkalemic.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the neuromuscular disorder.

In a further aspect, the disorder is associated with dysregulation of NF-κB signaling. In a still further aspect, the neuromuscular disorder is associated with activation of NF-κB signaling. In yet a further aspect, the neuromuscular disorder is associated with dysfunction of brain-derived neurotrophic factor.

In a further aspect, the neuromuscular disorder is selected from a muscular dystrophy, a spinal muscular atrophy, a disease of the neuromuscular junction, a disease of the peripheral nerve, and an inflammatory myopathy. In yet a further aspect, the muscular dystrophy is selected from Duchenne muscular dystrophy (DMD) and Becker muscular dystrophy (BMD). In an even further aspect, the neuromuscular disorder is DMD. In a still further aspect, the spinal muscular atrophy is amyotrophic lateral sclerosis (ALS).

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a neuromuscular disorder. In a still further aspect, the at least one agent is selected from a corticosteroid, methotrexate, azathioprine, cyclosporine, cyclophosphamide, chlorambucil, immunoglobulin, plasmapheresis, riluzole, gabapentin, ascorbic acid, vitamin E, beta carotene, an acetylcholinesterase inhibitor, and a cholinesterase inhibitor.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Modifying NF-κB Signaling in a Subject

In one aspect, disclosed are methods of modifying NF-κB signaling in a subject, the method comprising the step of administering to the subject an effective amount of at least one disclosed compound, or a pharmaceutically acceptable salt thereof.

In one aspect, disclosed are methods of modifying NF-κB signaling in a subject, the method comprising the step of administering to the subject an effective amount of at least one compound having a structure represented by a formula selected from:

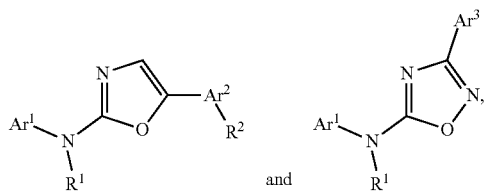

and wherein R¹ is selected from hydrogen and C1-C4 alkyl; wherein R², when present, is selected from —C(F)=CHCH₃, —C(CN)=NOCH₃, —CO₂R²¹, —SO₂R²¹, —NR²²ᵃR²²ᵇ, —CH₂NR²²ᵃR²²ᵇ, —C(O)NR²²ᵃR²²ᵇ, —CH(CF₃)NR²²ᵃR²²ᵇ, —SO₂NR²²ᵃR²²ᵇ, —NR²³SO₂R²⁴, and Cy¹; wherein each of R²¹, R²²ᵃ, R²²ᵇ, R²³, and R²⁴, when present, is independently selected from hydrogen, halogen, C1-C4 alkyl, C1-C4 alkoxy, C1-C4 haloalkyl, and Cy¹; wherein Cy¹, when present, is a structure having a formula selected from:

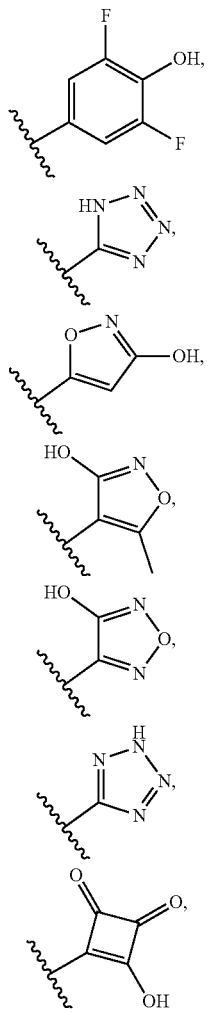

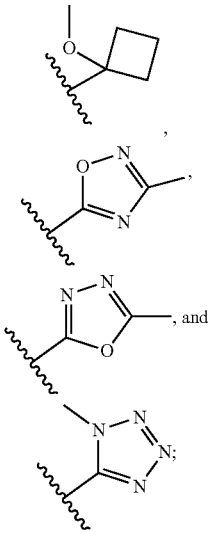

wherein Ar¹ is selected from monocyclic aryl and pyridinyl, and is substituted with 0, 1, 2, or 3 groups independently selected from halogen, —CN, —NH₂, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar², when present, is selected from monocyclic aryl and pyridinyl, and is substituted with 0, 1, or 2 independently selected R⁴ groups; wherein each occurrence of R⁴, when present, is independently selected from halogen, —NH₂, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH₃, —C(CN)=NOCH₃, —CO₂R³¹, —SO₂R³¹, —CO₂NR³²ᵃR³²ᵇ, —CH(CF₃)NR³²ᵃR³²ᵇ, —SO₂NR³²ᵃR³²ᵇ, —NR³³SO₂R³⁴, and Cy¹; wherein each of R³¹, R³²ᵃ, R³²ᵇ, R³³, and R³⁴, when present, is independently selected from hydrogen, halogen, C1-C4 alkyl, C1-C4 alkoxy, C1-C4 haloalkyl, and Cy¹; wherein Ar³, when present, is selected from monocyclic aryl and pyridinyl, and is substituted with 0, 1, 2, or 3 R⁴ groups; provided that when R¹ is hydrogen, R² is —CO₂H or —NH₂, and Ar² is monocyclic aryl, then Ar¹ is monocyclic aryl substituted with 1, 2, or 3 halogen groups or pyridinyl, and provided that either Ar³ is pyridinyl or when Ar³ is monocyclic aryl, R¹ is hydrogen, or a pharmaceutically acceptable salt thereof.

In a further aspect, modifying is activating.

In a further aspect, the compound exhibits activation of NF-κB signaling. In a still further aspect, the compound exhibits an increase in NF-κB signaling.

In a further aspect, the compound exhibits activation of NF-κB signaling with an EC₅₀ of less than about 30 μM. In a still further aspect, the compound exhibits activation of NF-κB signaling with an EC₅₀ of less than about 25 μM. In yet a further aspect, the compound exhibits activation of NF-κB signaling with an EC₅₀ of less than about 20 μM. In an even further aspect, the compound exhibits activation of NF-κB signaling with an EC₅₀ of less than about 15 μM. In a still further aspect, the compound exhibits activation of NF-κB signaling with an EC$_{50}$ of less than about 10 μM. In yet a further aspect, the compound exhibits activation of NF-κB signaling with an EC$_{50}$ of less than about 5 μM. In an even further aspect, the compound exhibits activation of NF-κB signaling with an EC$_{50}$ of less than about 1 μM. In a still further aspect, the compound exhibits activation of NF-κB signaling with an EC$_{50}$ of less than about 0.5 μM.

In a further aspect, the subject is a mammal. In a still further aspect, the subject is a human.

In a further aspect, the subject has been diagnosed with a need for treatment of a neurological disorder prior to the administering step. In a still further aspect, the method further comprises the step of identifying a subject in need of treatment of a neurological disorder.

In a further aspect, the subject has been diagnosed with a need for treatment of a neuromuscular disorder prior to the administering step. In a still further aspect, the method further comprises the step of identifying a subject in need of treatment of a neuromuscular disorder.

In a further aspect, the subject has been diagnosed with a need for treatment of a disorder associated with NF-κB signaling dysfunction prior to the administering step. In a still further aspect, the method further comprises the step of identifying a subject in need of treatment of a disorder associated with NF-κB signaling dysfunction. In yet a further aspect, the disorder associated with NF-κB signaling dysfunction is a neurological disorder. In an even further aspect, the disorder associated with NF-κB signaling dysfunction is a neuromuscular disorder.

In a further aspect, the subject has been diagnosed with a need for modifying NF-κB signaling prior to the administering step. In a still further aspect, the subject has been diagnosed with a need for activating NF-κB signaling prior to the administering step.

3. Methods of Modifying NF-κB Signaling in at Least One Cell

In one aspect, disclosed are methods for modifying NF-κB signaling in at least one cell, the method comprising the step of contacting the at least one cell with an effective amount of at least one disclosed compound, or a pharmaceutically acceptable salt thereof.

In one aspect, disclosed are methods for modifying NF-κB signaling in at least one cell, the method comprising the step of contacting at least one cell with an effective amount of at least one compound having a structure represented by a formula selected from:

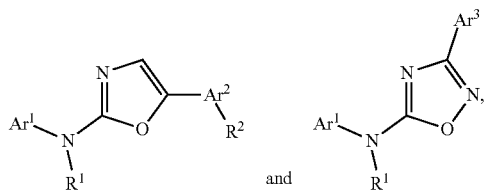

wherein R$^1$ is selected from hydrogen and C1-C4 alkyl; wherein R$^2$, when present, is selected from —C(F)═CHCH$_3$, —C(CN)═NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$; wherein each of R$^{21}$, R$^{22a}$, R$^{22b}$, R$^{23}$, and R$^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

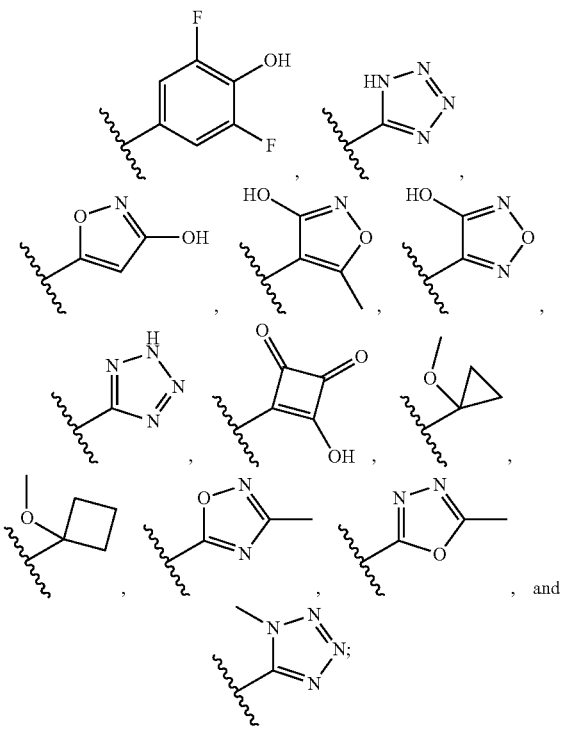

wherein Ar$^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^2$, when present, is selected from monocyclic aryl and pyridinyl, and is substituted with 0, 1, or 2 independently selected R$^4$ groups; wherein each occurrence of R$^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)═CHCH$_3$, —C(CN)═NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$; wherein each of R$^{31}$, R$^{32a}$, R$^{32b}$, R$^{33}$, and R$^{34}$, when present, is independently selected from hydrogen, halogen, C1-C4 alkyl, C1-C4 alkoxy, C1-C4 haloalkyl, and Cy$^1$; wherein Ar$^3$, when present, is selected from monocyclic aryl and pyridinyl, and is substituted with 0, 1, 2, or 3 R$^4$ groups; provided that when R$^1$ is hydrogen, R$^2$ is —CO$_2$H or —NH$_2$, and Ar$^2$ is monocyclic aryl, then Ar$^1$ is monocyclic aryl substituted with 1, 2, or 3 halogen groups or pyridinyl, and provided that either Ar$^3$ is pyridinyl or when Ar$^3$ is monocyclic aryl, R$^1$ is hydrogen, or a pharmaceutically acceptable salt thereof.

In a further aspect, modifying is increasing.

In a further aspect, the cell is mammalian. In a still further aspect, the cell is human. In yet a further aspect, the cell has been isolated from a mammal prior to the contacting step. In an even further aspect, the cell has been isolated from a human prior to the contacting step.

In a further aspect, contacting is via administration to a subject.

In a further aspect, the subject has been diagnosed with a need for modification of NF-κB signaling prior to the administering step. In a still further aspect, the subject has been diagnosed with a need for treatment of a disorder associated with NF-κB signaling dysfunction.

4. Methods of Modifying Brain-Derived Neurotrophic Factor Signaling in a Subject In one aspect, disclosed are methods of modifying brain-derived neurotrophic factor signaling in a subject, the method comprising the step of administering to the subject an effective amount of at least one disclosed compound, or a pharmaceutically acceptable salt thereof.

In one aspect, disclosed are methods for modifying brain-derived neurotrophic factor signaling in a subject, the method comprising the step of administering to the subject an effective amount of at least one compound having a structure represented by a formula selected from:

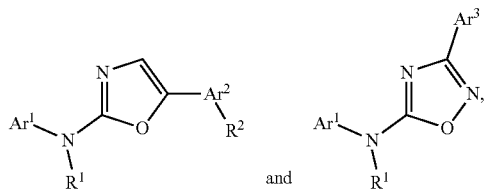

and wherein $R^1$ is selected from hydrogen and C1-C4 alkyl; wherein $R^2$, when present, is selected from —C(F)=CHCH$_3$, —C(CN)=NOCH$_3$, —CO$_2$R$^{21}$, —SO$_2$R$^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2$R$^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and Cy$^1$; wherein Cy$^1$, when present, is a structure having a formula selected from:

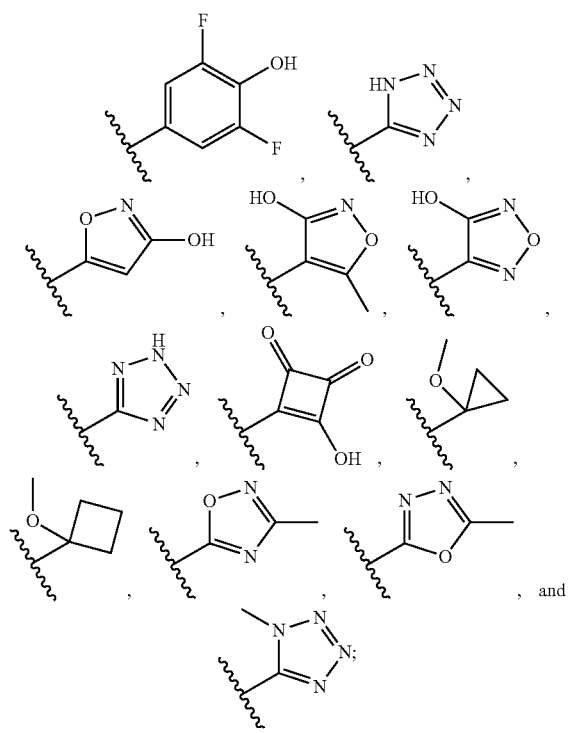

wherein Ar$^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^2$, when present, is selected from monocyclic aryl and pyridinyl, and is substituted with 0, 1, or 2 independently selected $R^4$ groups; wherein each occurrence of $R^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2$R$^{31}$, —SO$_2$R$^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2$R$^{34}$, and Cy$^1$; wherein each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and Cy$^1$; wherein Ar$^3$, when present, is selected from monocyclic aryl and pyridinyl, and is substituted with 0, 1, 2, or 3 $R^4$ groups; provided that when $R^1$ is hydrogen, $R^2$ is CO$_2$H or —NH$_2$, and Ar$^2$ is monocyclic aryl, then Ar$^1$ is monocyclic aryl substituted with 1, 2, or 3 halogen groups or pyridinyl, and provided that either Ar$^3$ is pyridinyl or when Ar$^3$ is monocyclic aryl, $R^1$ is hydrogen, or a pharmaceutically acceptable salt thereof.

In a further aspect, modifying is activating.

In a further aspect, the compound exhibits activation of brain-derived neurotrophic factor signaling. In a still further aspect, the compound exhibits an increase in brain-derived neurotrophic factor signaling.

In a further aspect, the compound exhibits activation of brain-derived neurotrophic factor signaling with an EC$_{50}$ of less than about 30 μM. In a still further aspect, the compound exhibits activation of brain-derived neurotrophic factor signaling with an EC$_{50}$ of less than about 25 μM. In yet a further aspect, the compound exhibits activation of brain-derived neurotrophic factor signaling with an EC$_{50}$ of less than about 20 μM. In an even further aspect, the compound exhibits activation of brain-derived neurotrophic factor signaling with an EC$_{50}$ of less than about 15 μM. In a still further aspect, the compound exhibits activation of brain-derived neurotrophic factor signaling with an EC$_{50}$ of less than about 10 μM. In yet a further aspect, the compound exhibits activation of brain-derived neurotrophic factor signaling with an EC$_{50}$ of less than about 5 μM. In an even further aspect, the compound exhibits activation of brain-derived neurotrophic factor signaling with an EC$_{50}$ of less than about 1 μM. In a still further aspect, the compound exhibits activation of brain-derived neurotrophic factor signaling with an EC$_{50}$ of less than about 0.5 μM.

In a further aspect, the subject is a mammal. In a still further aspect, the subject is a human.

In a further aspect, the subject has been diagnosed with a need for treatment of a neurological disorder prior to the administering step. In a still further aspect, the method further comprises the step of identifying a subject in need of treatment of a neurological disorder.

In a further aspect, the subject has been diagnosed with a need for treatment of a neuromuscular disorder prior to the administering step. In a still further aspect, the method further comprises the step of identifying a subject in need of treatment of a neuromuscular disorder.

In a further aspect, the subject has been diagnosed with a need for treatment of a disorder associated with brain-derived neurotrophic factor signaling dysfunction prior to the administering step. In a still further aspect, the method further comprises the step of identifying a subject in need of treatment of a disorder associated with brain-derived neurotrophic factor signaling dysfunction. In yet a further aspect, the disorder associated with brain-derived neurotrophic factor signaling dysfunction is a neurological disorder. In an even further aspect, the disorder associated with brain-derived neurotrophic factor signaling dysfunction is a neuromuscular disorder.

In a further aspect, the subject has been diagnosed with a need for modifying brain-derived neurotrophic factor signaling prior to the administering step. In a still further aspect, the subject has been diagnosed with a need for activating brain-derived neurotrophic factor signaling prior to the administering step.

5. Methods of Modifying Brain-Derived Neurotrophic Factor Signaling in at Least One Cell In one aspect, disclosed are methods for modifying brain-derived neurotrophic factor signaling in at least one cell, the method comprising the step of contacting the at least one cell with an effective amount of at least one disclosed compound, or a pharmaceutically acceptable salt thereof.

In one aspect, disclosed are methods for modifying brain-derived neurotrophic factor signaling in at least one cell, the method comprising the step of contacting at least one cell with an effective amount of at least one compound having a structure represented by a formula selected from:

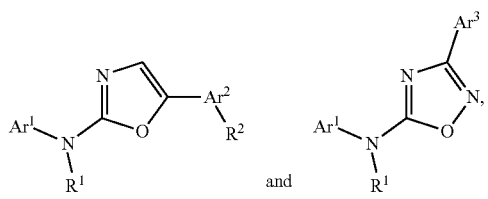

wherein $R^1$ is selected from hydrogen and C1-C4 alkyl; wherein $R^2$, when present, is selected from —C(F)=CHCH$_3$, —C(CN)=NOCH$_3$, —CO$_2R^{21}$, —SO$_2R^{21}$, —NR$^{22a}$R$^{22b}$, —CH$_2$NR$^{22a}$R$^{22b}$, —C(O)NR$^{22a}$R$^{22b}$, —CH(CF$_3$)NR$^{22a}$R$^{22b}$, —SO$_2$NR$^{22a}$R$^{22b}$, —NR$^{23}$SO$_2R^{24}$, and Cy$^1$; wherein each of $R^{21}$, $R^{22a}$, $R^{22b}$, $R^{23}$, and $R^{24}$, when present, is independently selected from hydrogen, halogen, C1-C4 alkyl, C1-C4 alkoxy, C1-C4 haloalkyl, and Cy %; wherein Cy$^1$, when present, is a structure having a formula selected from:

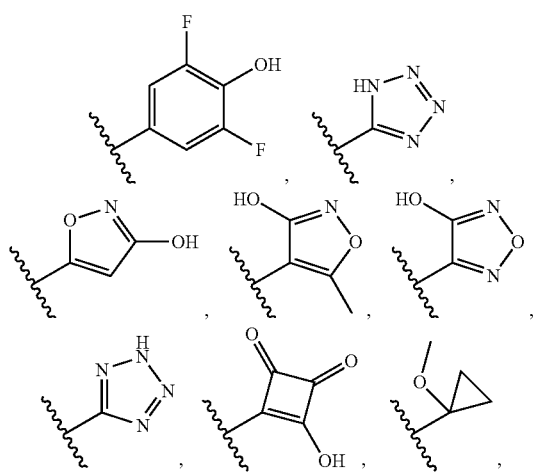

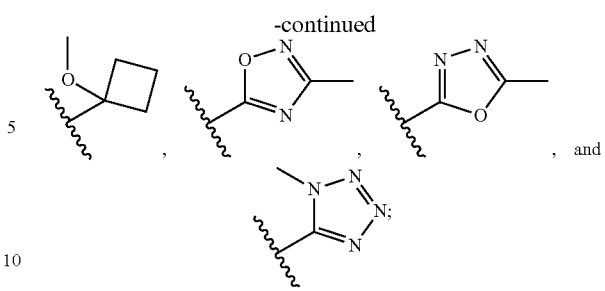

wherein $Ar^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^2$, when present, is selected from monocyclic aryl and pyridinyl, and is substituted with 0, 1, or 2 independently selected $R^4$ groups; wherein each occurrence of $R^4$, when present, is independently selected from halogen, —NH$_2$, —OH, —CN, C1-C4 alkyl, C1-C4 haloalkyl, C1-C4 hydroxyalkyl, C1-C4 alkoxy, C1-C4 alkylamino, (C1-C4)(C1-C4) dialkylamino, —C(F)=CHCH$_3$, —C(CN)=NOCH$_3$, —CO$_2R^{31}$, —SO$_2R^{31}$, —CO$_2$NR$^{32a}$R$^{32b}$, —CH(CF$_3$)NR$^{32a}$R$^{32b}$, —SO$_2$NR$^{32a}$R$^{32b}$, —NR$^{33}$SO$_2R^{34}$, and Cy$^1$; wherein each of $R^{31}$, $R^{32a}$, $R^{32b}$, $R^{33}$, and $R^{34}$, when present, is independently selected from hydrogen, halogen, C1-C4 alkyl, C1-C4 alkoxy, C1-C4 haloalkyl, and Cy$^1$; wherein $Ar^3$, when present, is selected from monocyclic aryl and pyridinyl, and is substituted with 0, 1, 2, or 3 $R^4$ groups; provided that when $R^1$ is hydrogen, $R^2$ is —CO$_2$H or —NH$_2$, and $Ar^2$ is monocyclic aryl, then $Ar^1$ is monocyclic aryl substituted with 1, 2, or 3 halogen groups or pyridinyl, and provided that either $Ar^3$ is pyridinyl or when $Ar^3$ is monocyclic aryl, $R^1$ is hydrogen, or a pharmaceutically acceptable salt thereof.

In a further aspect, modifying is increasing.

In a further aspect, the cell is mammalian. In a still further aspect, the cell is human. In yet a further aspect, the cell has been isolated from a mammal prior to the contacting step. In an even further aspect, the cell has been isolated from a human prior to the contacting step.

In a further aspect, contacting is via administration to a subject.

In a further aspect, the subject has been diagnosed with a need for modification of brain-derived neurotrophic factor prior to the administering step. In a still further aspect, the subject has been diagnosed with a need for treatment of a disorder associated with brain-derived neurotrophic factor signaling dysfunction.

6. Use of Compounds

In one aspect, the invention relates to the use of a disclosed compound or a product of a disclosed method. In a further aspect, a use relates to the manufacture of a medicament for the treatment of a neurological disorder in a subject. In a still further aspect, a use relates to the manufacture of a medicament for the treatment of a neuromuscular disorder in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a neurological disorder in a subject. Also disclosed is the use of a compound for antagonism of a neurological disorder. In one aspect, the use is characterized in that the subject is a human. In one aspect, the use is characterized in that the disorder is a neurological disorder.

In various aspects, the use relates to a treatment of a neuromuscular disorder in a subject. Also disclosed is the use of a compound for antagonism of a neuromuscular disorder. In one aspect, the use is characterized in that the subject is a human. In one aspect, the use is characterized in that the disorder is a neuromuscular disorder.

In a further aspect, the use relates to the manufacture of a medicament for the treatment of a neurological disorder in a subject.

In a further aspect, the use relates to the manufacture of a medicament for the treatment of a neuromuscular disorder in a subject.

In a further aspect, the use relates to antagonism of a neurological disorder in a subject. In a further aspect, the use relates to antagonism of a neuromuscular disorder in a subject.

In a further aspect, the use relates to modulating viral activity in a subject. In a still further aspect, the use relates to modulating viral activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a neurological disorder in a mammal. In a further aspect, the neurological disorder is ALS. In a further aspect, the invention relates to the use of a disclosed compound or a disclosed product in the manufacture of a medicament for the treatment of a neuromuscular disorder in a mammal. In a further aspect, the neuromuscular disorder is DMD.

7. Manufacture of a Medicament

In one aspect, the invention relates to a method for the manufacture of a medicament for treating a neurological disorder in a subject having the neurological disorder, the method comprising combining a therapeutically effective amount of a disclosed compound or product of a disclosed method with a pharmaceutically acceptable carrier or diluent.

In one aspect, the invention relates to a method for the manufacture of a medicament for treating a neuromuscular disorder in a subject having the neuromuscular disorder, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the treatment of a neurological disorder. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

8. Kits

In one aspect, the invention relates to a kit comprising at least one disclosed compound and one or more of: (a) at least one agent associated with the treatment of a neurological disorder; (b) at least one agent associated with the treatment of a neuromuscular disorder; (c) instructions for administering the compound in connection with treating a neurological disorder; (d) instructions for administering the compound in connection with reducing the risk of a neurological disorder; (e) instructions for treating a neurological disorder; (f) instructions for administering the compound in connection with treating a neuromuscular disorder; (g) instructions for administering the compound in connection with reducing the risk of a neuromuscular disorder; and (h) instructions for treating a neuromuscular disorder.

In a further aspect, the neurological disorder is selected from amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD). In a further aspect, the neurological disorder is ALS. In a still further aspect, the neurological disorder is ALS.

In a further aspect, the agent associated with the treatment of a neurological disorder is selected from a cholinesterase inhibitor, an antidepressant, memantine, rilutek, radicava, levodopa, carbidopa, a dopamine agonist, a MAO-B inhibitor, a catechol-O-methyltransferase inhibitor, an anticholinergic, spinraza, tetrabenazine, an antipsychotic agent, levetiracetam, clonazepam, an antipsychotic agent, a mood-stabilizing agent, and amantadine.

In a further aspect, the at least one compound and the at least one agent associated with the treatment of a neurological disorder are co-formulated. In a further aspect, the at least one compound and the at least one agent associated with the treatment of a neurological disorder are co-packaged.

In a further aspect, the neuromuscular disorder is selected from a muscular dystrophy, a spinal muscular atrophy, a disease of the neuromuscular junction, a disease of the peripheral nerve, and an inflammatory myopathy. In yet a further aspect, the muscular dystrophy is selected from Duchenne muscular dystrophy (DMD) and Becker muscular dystrophy (BMD). In an even further aspect, the neuromuscular disorder is DMD. In a still further aspect, the spinal muscular atrophy is amyotrophic lateral sclerosis (ALS).

In a further aspect, the agent associated with the treatment of a neuromuscular disorder is selected from a corticosteroid, methotrexate, azathioprine, cyclosporine, cyclophosphamide, chlorambucil, immunoglobulin, plasmapheresis, riluzole, gabapentin, ascorbic acid, vitamin E, beta carotene, an acetylcholinesterase inhibitor, and a cholinesterase inhibitor.

In a further aspect, the at least one compound and the at least one agent associated with the treatment of a neuromuscular disorder are co-formulated. In a further aspect, the at least one compound and the at least one agent associated with the treatment of a neuromuscular disorder are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

F. References

Writing and Edaravone (2017) *The Lancet Neurology* 16(7): 505-12.
Petrov et al. (2017) *Frontiers in aging neuroscience* 9:68.
Manuvakhova et al. (2011) *Journal of neuroscience research* 89(1):58-72.
Sarnico et al. (2009) *International review of neurobiology* 85:351-62.
Carri et al. (2015) *Frontiers in cellular neuroscience* 9:41.
Kuntzen et al. (2007) *Methods in molecular biology* 399:99-124.
Kaltschmidt et al. (2005) *Biochimica et biophysica acta* 1745(3):287-99.
Neidl et al. (2016) *The Journal of neuroscience: the official journal of the Society for Neuroscience* 36(15):4351-61.
Marini et al. (2004) *Restorative neurology and neuroscience* 22(2):121-30.
Ho et al. (2009) *Current molecular pharmacology* 2(1):19-31.
Ahmed et al. (2015) *Biomolecules* 5(4):3087-111.
Blaser H, Dostert C, Mak T W, Brenner D. TNF and ROS Crosstalk in Inflammation. Trends in cell biology. 2016 April; 26(4):249-61. PubMed PMID: 26791157.
Ikiz B, Alvarez M J, Re D B, Le Verche V, Politi K, Lotti F, et al. The Regulatory Machinery of Neurodegeneration in In Vitro Models of Amyotrophic Lateral Sclerosis. Cell reports. 2015 Jul. 14; 12(2):335-45. PubMed PMID: 26146077. Pubmed Central PMCID: 4646662.
Skibsbye et al. (2015) *Journal of cardiovascular pharmacology* 66(2):165-76.
Gallardo-Godoy et al. (2011) *Journal of medicinal chemistry* 54(4):1010-21.
Nardo et al. (2016) *Brain pathology* 26(2):237-47.
Philips and Rothstein (2015) *Current protocols in pharmacology* 69:5 67 1-21.
Si et al. (2014) *Annals of clinical and translational neurology* 1(10):778-87.
Si et al. (2015) *PloS one* 10(9):e0138425.
Melanie Leitner PDSM, Ph.D.; Cathleen Lutz, Ph.D. Working with ALS Mice: Guidelines for preclinical testing & colony management. Cambridge, MA: Prize4Life; 2009.
Galasso et al. (2000) *Experimental neurology* 165(2):295-305.
Cowell et al. (2003) *The Journal of neuroscience: the official journal of the Society for Neuroscience* 15; 23(28):9459-68.
Cowell et al. (2006) *Journal of neuroimmunology* 173(1-2):155-65.
Moehle et al. (2012) *The Journal of neuroscience: the official journal of the Society for Neuroscience* 32(5):1602-11.
Dougherty et al. (2012) *Experimental neurology* 236(1):171-8.
Dougherty et al. (2014) *Neurobiology of disease* 62:160-71.
Jiang et al. (2013) *Biological psychiatry* 73(10):1024-34.
Jiang et al. (2013) *Frontiers in behavioral neuroscience* 7:116.
Lucas et al. (2012) *PloS one* 7(8):e42878.
Lucas et al. (2014) *The Journal of neuroscience: the official journal of the Society for Neuroscience* 34(43):14375-87.
Dougherty et al. (2014) *Neuroscience* 271:137-48.
Dougherty et al. (2013) *Experimental neurology* 240:96-102.
Cowell et al. (2007) *The Journal of comparative neurology* 502(1):1-18.
Scott et al. (2008) *Amyotrophic lateral sclerosis: official publication of the World Federation of Neurology Research Group on Motor Neuron Diseases* 9(1):4-15.
Gurney et al. (1994) *Science* 264(5166):1772-5.
Guyenet et al. (2010) *Journal of visualized experiments: JoVE* 21(39).
Bursavich et al. (2010) *Bioorganic & medicinal chemistry letters* 20(5):1677-9.
Ballatore et al. (2013) *ChemMedChem* 8(3):385-95.
Trstenjak et al. (2013) *European journal of medicinal chemistry* 64:302-13.
Hammam et al. (1985) *Egyptian Journal of Chemistry* 27:515-23.
Cowell et al. (2009) *Biochemical and biophysical research communications* 379(2):578-82.
Hoekman and Ho (2011) *Anesthesia and analgesia* 113(3):641-51.
Landis et al. (2012) *Therapeutic delivery* 3(2):195-208.
Lochhead and Thorne (2012) *Advanced drug delivery reviews* 64(7):614-28.
Pizzi et al. (2009) *The FEBS journal* 276(1):27-35.
Henkel et al. (2009) *Journal of neuroimmune pharmacology: the official journal of the Society on NeuroImmune Pharmacology* 4(4):389-98.
Berent-Spillson and Russell (2007) *Journal of neurochemistry* 101(2):342-54.
Chen et al. (2009) *The Journal of neuroscience: the official journal of the Society for Neuroscience* 29(35):10909-19.

Vaden et al. (2015) *Frontiers in molecular neuroscience* 8:11.
Martin et al. (2015) *Journal of visualized experiments: JoVE* 25(99):e52605.
Periasamy et al. (2016) *PLoS pathogens* 12(3):e1005517.
Xia et al. (2010) *Muscle & nerve* 41(6):850-6.
Bogdanik et al. (2015) *Proceedings of the National Academy of Sciences of the United States of America* 112(43): E5863-72.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

G. Examples

ALS is characterized by progressive degeneration of motor neurons of the ventral spinal cord and cortical projection neurons, causing muscle atrophy, paralysis, and death. Strategies to prevent neuronal loss are required to prevent the onset and/or progression of ALS (Writing and Edaravone (2017) *The Lancet Neurology* 16(7):505-12. PubMed PMID: 28522181). In 1-3% of ALS cases, point mutations in the $Cu^{2+}/Zn^{2+}$ superoxide dismutase 1 (SOD1) gene result in active enzymes with newly acquired properties, including hyper-generation of reactive oxygen species (ROS) (Petrov et al. (2017) *Frontiers in aging neuroscience* 9:68. PubMed PMID: 28382000. Pubmed Central PMCID: 5360725). SOD1 abnormalities have been identified in both familial as well as sporadic ALS cases (Manuvakhova et al. (2011) *Journal of neuroscience research.* 89(1):58-72. PubMed PMID: 21046675. Pubmed Central PMCID: 3280078). Unfortunately, co-expression of wild-type SOD1 with mutated SOD1 worsens the clinical outcome (Sarnico et al. (2009) *International review of neurobiology* 85:351-62. PubMed PMID: 19607980), ruling out substitutive gene therapy. Importantly, there is substantial evidence that ROS production is involved in the progression of ALS even in non-SOD1-associated cases (Carri et al. (2015) *Frontiers in cellular neuroscience* 9:41. PubMed PMID: 25741238. Pubmed Central PMCID: 4330888), raising the possibility that strategies to prevent the toxic effects of ROS could benefit patients with ALS, independent of etiology. In fact, the free radical scavenger Radicava (Edaravone) was recently FDA approved based on its ability to slow ALS progression in a subset of patients (Writing and Edaravone (2017) *The Lancet Neurology* 16(7):505-12. PubMed PMID: 28522181; Petrov et al. (2017) *Frontiers in aging neuroscience* 9:68. PubMed PMID: 28382000. Pubmed Central PMCID: 5360725).

Without wishing to be bound by theory, it is believed that increasing neuronal expression of superoxide dismutase 2 (SOD2), a $Mn^{2+}$-dependent enzyme that detoxifies ROS, should be used as a strategy to prevent the onset and/or progression of ALS. SOD2 is unaffected in ALS, and its expression is robustly inducible by activation of the NF-kB complex found in neurons (p50/p65) by direct binding of p65 to the SOD2 promoter (Kuntzen et al. (2007) *Methods in molecular biology* 399:99-124. PubMed PMID: 18309928; Kaltschmidt et al. (2005) *Biochimica et biophysica acta* 1745(3):287-99. PubMed PMID: 15993497; Neidl et al. (2016) *The Journal of neuroscience: the official journal of the Society for Neuroscience* 36(15):4351-61. PubMed PMID: 27076430). To identify putative small molecule activators of NF-kB activity and SOD2 expression, a high throughput, cell-based NF-kB reporter assay was designed and a series of compounds that increase SOD2 expression were found. These compounds cause increased p65 nuclear translocation without affecting the abundance of inhibitor of NF-κB (I-κBα), and prevent cell death caused by hydrogen peroxide or glutamate-induced cell death in cell culture systems (Writing and Edaravone (2017) *The Lancet Neurology* 16(7):505-12. PubMed PMID: 28522181). Without wishing to be bound by theory, it was hypothesized that the activation of endogenous transcriptional programs for SOD2 expression will boost neuronal antioxidant defenses and prevent and/or delay the progression of ALS.

The two lead compounds demonstrated powerful neurotrophic and neuroprotective activity. In addition, they up-regulated SOD2 expression/activity in human and rat neurons. These compounds also demonstrated in in vivo activity in a mouse model of ALS. Briefly, Congenic SOD1-G93A mice were dosed with up to 50 mg/kg of both compounds (IP) to evaluate any toxicity issues prior to initiating the efficacy study. Also, mice administered 20 mg of each compound had high plasma and brain levels at 30 minutes. Next, individually genotyped SOD1-G93A mice (Prize4life-Jackson Labs) were treated with each compound (25 mg/kg, IP) at disease onset (day 96). The treatment extended survival, reduced weight loss and improved the neurologic symptoms. For example, Kaplan-Meier survival analysis indicated that compound administration at the time of onset significantly extended survival. Data document a 66% and a 81% lifespan extension for the compounds, respectively, at 50% survival in male mice. A similar trend was observed in female mice. Animal weight, which reflects muscle atrophy and metabolic weight waste, was also significantly reduced by the treatments. The average weight within the groups before the treatment was similar. However, at 120 days, control animals lost on average 12% of the body weight and compound treated mice lost only 3% (75% inhibition) and 4% (65% inhibition) of the body weight, respectively.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. General Experimental

All reactions were carried out in an oven- or flame-dried glassware under argon atmosphere using standard gas-tight syringe, cannula, and septa. The reaction temperatures were measured externally. Stirring was achieved with oven dried magnetic bars. All the reactions were done in anhydrous solvents (DMF, THF, CH$_2$Cl$_2$, 1,4-Dioxane, 1-Butanol, CHCl$_3$, DME) purchased from Sigma-Aldrich. Microwave reactions were performed in CEM discover Labmate System with Intelligent Technology for Focused Microwave Synthesizer (Explorer 48). All commercially purchased reagents were used without purification. The reactions were monitored by thin-layer chromatography (TLC) on a pre-coated silica gel (60 F254) glass plates from EMD Millipore and visualized using UV light (254 nm). Purification of the compounds was performed on Teledyne-ISCO Combiflash Rf 200 purification system. Used Redisep Rf® normal phase silica gel columns 230-400 mesh. Proton NMR spectra were recorded on a Varian Unity 400 NMR spectrometer operating at 400 MHz calibrated to the solvent peak and TMS peak. The chemical formula and Exact Mass for target compounds were determined from the (M+H)+ by high resolution mass spectroscopy using an Agilent 6210 Electrospray Time of Flight The purity of the final compounds were checked by HPLC using Agilent 1100 LC equipped with a diode array UV detector and monitored at multiple wavelengths on Bondclone 10µ C18 column using Solvent A: H$_2$O, Solvent B: CH$_3$CN, 1.0 ml/min; 30 min linear gradient from 10-90% B, or on Waters HPLC equipped with a 3100 Mass Detector using Sunfire C18 column (5 µM, 4.6×150 mm) using ACN-H2) (both containing 0.1% formic acid) from 10-90% gradient in 15 min. ESI-MS spectra were recorded on a BioTof-2 time-of-flight mass spectrometer.

b. General Procedure for the Synthesis of Amino-Oxazole Analogs

Step 1: Sodium azide (3 eq) was added to a solution of appropriate methyl (2-bromoacetyl)benzoate (1 eq.) in Acetone/Water (2:1) and the reaction mixture was allowed to stir at room temperature for 1 h. Water was added to the reaction mixture and extracted with CH$_2$Cl$_2$ (3×). The combined organic layer was washed with brine and dried over anhydrous Na$_2$SO$_4$. The drying agent was filtered and the filtrate was concentrated under vacuum to obtain the corresponding azide in good yields. The crude product was dried and used for the next step without any further purification.

Step 2: A solution of the appropriate methyl (azidoacetyl) benzoate (1 eq.), the appropriate fluoro isothiocyanatobenzene (1 eq.), and triphenylphosphine (1 equivalent) in anhydrous dioxane (2 mL) under nitrogen was taken in a microwave tube and the reaction mixture was heated at 100° C. for 30 mins under microwave conditions. Progress of the reaction was monitored by TLC. The reaction mixture was concentrated under vacuum and purified on a Teledyne Isco Combiflash® Rf purification machine to provide the desired aminooxazole ester in moderate to good yields.

Step 3: 1 N NaOH (5 eq.) was added to a solution of the appropriate oxazole ester (1 eq.) in ethanol and the reaction mixture was heated at 60° C. overnight. The resulting mixture was concentrated under vacuum and the pH was adjusted to between 1-2 using 1 N HCl. The aqueous layer was extracted with CH$_2$Cl$_2$ (3×) and the combined organic layers were dried over anhydrous Na$_2$SO$_4$. The drying agent was filtered off and the filtrate was concentrated under vacuum. The crude product was purified on a Teledyne Isco Combiflash® Rf purification machine to provide the desired aminooxazole acid in moderate yields.

c. Synthesis of methyl 3-(2-((4-fluorophenyl)(methyl)amino)oxazol-5-yl)benzoate

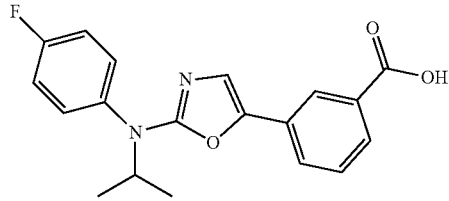 [SMILES: CC(C)N(c1ccc(F)cc1)c1ncc(-c2cccc(C(=O)O)c2)o1]

Sodium hydride (6.40 mg, 0.160 mmol) was added to a solution of methyl 3-(2-((4-fluorophenyl)amino)oxazol-5-yl)benzoate (25 mg, 0.080 mmol) in DMF (1 ml) at rt under Ar atmosphere. The resulted reaction mixture was stirred for 15 min and was added methyl iodide (10.01 µl, 0.160 mmol) and stirred for 1 h. Water (1 mL) was added to neutralize the reaction mixture and extracted with CH$_2$Cl$_2$ (thrice). The combined organic layer was dried over anhydrous Na$_2$SO$_4$. The drying agent was filtered off and the filtrate was concentrated under vacuum. Solvent was removed under vacuum and purified on Teledyne Isco Combiflash® Rf purification machine to provide methyl 3-(2-((4-fluorophenyl)(methyl)amino)oxazol-5-yl)benzoate in 27% yield.

d. Synthesis of 3-(2-(2-fluorophenyl)oxazol-5-yl)benzoic acid

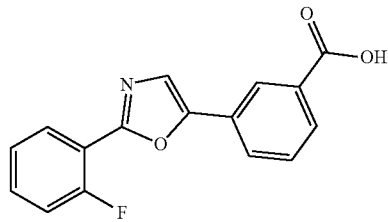 [SMILES: O=C(O)c1cccc(-c2cnc(-c3ccccc3F)o2)c1]

Iodine (2 eq.) was added to a microwave vessel containing a solution of 3-(2-bromoacetyl)benzoic acid (1 eq.), 2-Fluorobenzylamine (1.2 eq.) and Potassium carbonate (4 eq.) in DMF at room temperature under Argon atmosphere. The resulted reaction mixture was heated at 80° C. for 2 h under microwave conditions. The reaction mixture was washed with aq. sodium thiosulfate and extracted with CH$_2$Cl$_2$ (thrice). The combined organic layer was dried over anhydrous Na$_2$SO$_4$ and the solid was filtered off. Solvent was removed from the filtrate in vacuuo and the crude product was purified on Teledyne Isco Combiflash® Rf purification machine to afford 3-(2-(2-fluorophenyl)oxazol-5-yl)benzoic acid in 4% yield.

e. Synthesis of N-(2-fluorophen yl)-3-(pyridin-2-yl)-1,2,4-oxadiazol-5-amine

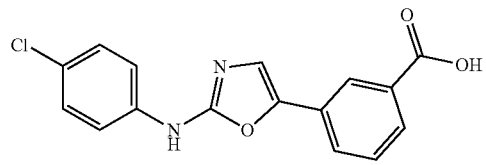 [SMILES: O=C(O)c1cccc(-c2cnc(Nc3ccc(Cl)cc3)o2)c1]

Step 1: Pyridine (1 eq.) and DMAP (0.05 eq.) were added to a solution of 3-(pyridin-2-yl)-1,2,4-oxadiazol-5(4H)-one (1 eq.) in POCl₃ (35 eq.) at room temperature under Ar atmosphere. The resulted reaction mixture was refluxed for 3 h and allowed to cool to room temperature The reaction mixture was diluted with cold water and extracted with CH₂Cl₂ (thrice). The combined organic layer was dried over anhydrous Na₂SO₄ and the filtrate was concentrated in vacuuo. The crude product (5-chloro-3-(pyridin-2-yl)-1,2,4-oxadiazole) was dried and used for next step without further purification.

Step 2: 2-Fluoroaniline (1 eq.) and DIEA (2 eq.) were added to a solution of 5-chloro-3-(pyridin-2-yl)-1,2,4-oxadiazole (1 eq.) in anhydrous DMF room temperature under Ar atmosphere. The resulted reaction mixture was heated at 60° C. for 3 h. Solvent was removed in vacuuo and the crude product was purified on Teledyne Isco Combiflash® Rf purification machine to provide N-(2-fluorophenyl)-3-(pyridin-2-yl)-1,2,4-oxadiazol-5-amine in 20% yield.

f. Synthesis of N-(2-fluorophenyl)-3-(pyridin-2-yl)-1,2,4-oxadiazol-5-amine

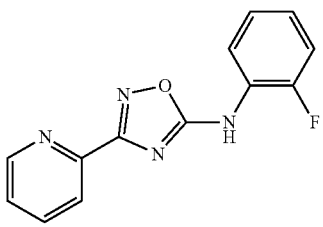 [SMILES: Fc1ccccc1Nc1nc(-c2ccccn2)no1]

Step 1: Pyridine (1 eq.) and DMAP (0.05 eq.) were added to a solution of 3-(pyridin-2-yl)-1,2,4-oxadiazol-5(4H)-one (1 eq.) in POCl₃ (35 eq.) at room temperature under Ar atmosphere. The resultant mixture was refluxed for 3 h and allowed to cool to room temperature. The reaction mixture was diluted with cold water and extracted with CH₂Cl₂ (3×). The combined organic layers were dried over anhydrous Na₂SO₄ and the filtrate was concentrated in vacuuo. The crude product (5-chloro-3-(pyridin-2-yl)-1,2,4-oxadiazole) was dried and used for the next step without further purification.

Step 2: 2-Fluoroaniline (1 eq.) and DIEA (2 eq.) were added to a solution of 5-chloro-3-(pyridin-2-yl)-1,2,4-oxadiazole (1 eq.) in anhydrous DMF room temperature under Ar atmosphere. The resulted reaction mixture was heated at 60° C. for 3 h. The solvent was removed in vacuuo and the crude product was purified on a Teledyne Isco Combiflash® Rf purification machine to provide N-(2-fluorophenyl)-3-(pyridin-2-yl)-1,2,4-oxadiazol-5-amine in 20% yield.

g. Spectral Data i. (Z)-1-(benzo[d][1,3]dioxol-5-yl)-3-((2-bromophenyl)amino)prop-2-en-1-one (1)

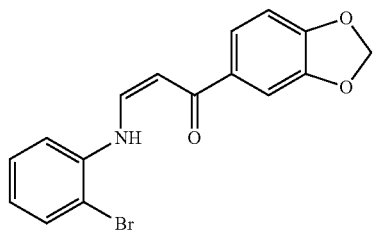 [SMILES: O=C(/C=C\Nc1ccccc1Br)c1ccc2c(c1)OCO2]

¹H NMR (400 MHz, DMSO-d₆) δ 12.27 (d, J=11.8 Hz, 1H), 7.93 (dd, J=11.9, 8.0 Hz, 1H), 7.71-7.59 (m, 3H), 7.50 (s, 1H), 7.39 (t, J=7.8 Hz, 1H), 7.07-6.92 (m, 2H), 6.22 (d, J=7.9 Hz, 1H), 6.11 (s, 2H).

ii. 3-(2-((2-fluorophenyl)amino)oxazol-5-yl)benzoic acid (40)

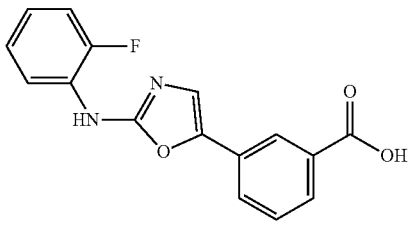 [SMILES: O=C(O)c1cccc(-c2cnc(Nc3ccccc3F)o2)c1]

¹H NMR (400 MHz, DMSO-d₆) δ 10.13 (s, 1H), 8.19 (td, J=8.4, 1.7 Hz, 1H), 8.14 (t, J=1.8 Hz, 1H), 7.84-7.78 (m, 2H), 7.58 (s, 1H), 7.54 (t, J=7.8 Hz, 1H), 7.31-7.11 (m, 2H), 7.06-7.00 (m, 1H).

iii. Methyl 3-(2-((2,4-difluorophenyl)amino)oxazol-5-yl)benzoate (61)

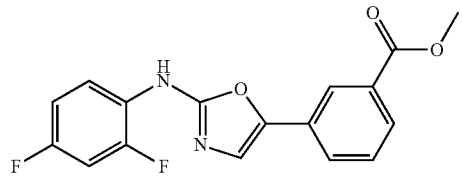 [SMILES: COC(=O)c1cccc(-c2cnc(Nc3ccc(F)cc3F)o2)c1]

¹H NMR (400 MHz, DMSO-d₆) δ 10.14 (s, 1H), 8.22-8.06 (m, 2H), 7.87-7.80 (m, 2H), 7.65-7.51 (m, 2H), 7.32 (ddd, J=11.6, 8.9, 2.9 Hz, 1H), 7.15-7.00 (m, 1H), 3.87 (s, 3H).

iv. Methyl 4-(2-((2-fluorophenyl)amino)oxazol-5-yl)benzoate (65)

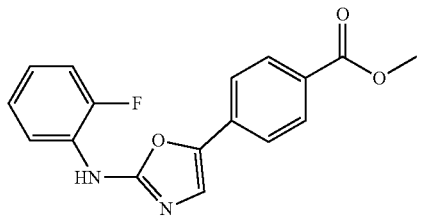 [SMILES: COC(=O)c1ccc(-c2cnc(Nc3ccccc3F)o2)cc1]

$^1$H NMR (400 MHz, DMSO-d$_6$) δ 10.23 (s, 1H), 8.15 (td, J=8.4, 1.7 Hz, 1H), 8.04-7.98 (m, 2H), 7.73-7.67 (m, 3H), 7.30-7.17 (m, 2H), 7.09-7.02 (m, 1H), 3.86 (s, 3H).

v. Methyl 4-(2-((2,5-difluorophenyl)amino)oxazol-5-yl)benzoate (69)

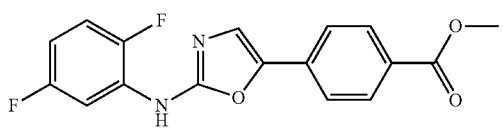 [SMILES: COC(=O)c1ccc(-c2cnc(Nc3cc(F)ccc3F)o2)cc1]

$^1$H NMR (400 MHz, DMSO-d$_6$) δ 10.58 (s, 1H), 8.16 (ddd, J=10.9, 6.7, 3.2 Hz, 1H), 8.05-7.99 (m, 2H), 7.76-7.70 (m, 3H), 7.31 (ddd, J=10.9, 9.0, 5.2 Hz, 1H), 6.88-6.82 (m, 1H), 3.86 (s, 3H).

vi. Methyl 4-(2-((2,6-difluorophenyl)amino)oxazol-5-yl)benzoate (70)

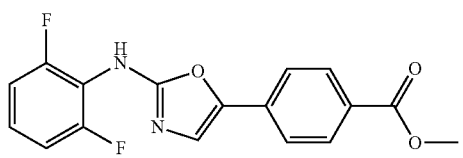 [SMILES: COC(=O)c1ccc(-c2cnc(Nc3c(F)cccc3F)o2)cc1]

$^1$H NMR (400 MHz, DMSO-d$_6$) δ 9.92 (s, 1H), 8.01-7.94 (m, 2H), 7.64-7.59 (m, 2H), 7.56 (s, 1H), 7.35 (p, J=7.2 Hz, 1H), 7.26-7.18 (m, 2H), 3.85 (s, 3H).

2. Methods a. High Throughput Assay for NF-κB Reporter Activity

SH-SY5Y human neuroblastoma cell line was obtained from the American Tissue Culture collection (ATCC). A commercially available expression vector containing the NF-kB promoter enhancer region driving the firefly luciferase gene expression and a second plasmid containing the gene conferring resistance to blasticidin were used in a dual transfection approach to obtain a stable cell line. SH-SY5Y cells stably transfected with pNF-κB-luc/pEF6 were plated at 8,000 per well in a volume of 40 μl DMEM in either Corning white opaque, 384-well plates (Cat. No. 3570, Corning, Inc., Corning, NY) or Corning black clear bottom, 384-well plates (Cat. No. 3712, Corning, Inc., Corning, NY) and treated with test compounds for 24 hr at 37° C. Luciferase activity was measured as a reporter of NF-kB activation using the Bright-Glo Luciferase assay kit (Cat. No. E2620, Promega, Madison, WI) according to the manufacturer's instructions. Cell viability was measured using the CellTiter-Glo Luminescent Cell Viability assay kit (Cat. No. G7572, Promega, Madison, WI) according to the manufacturer's instructions. Briefly, cells were equilibrated at room temperature for 30 min prior to the addition of Bright-Glo to the white opaque plates or CellTiter-Glo to the black clear bottom plates. A volume of assay buffer equal to the volume of cell media was added to each well and incubated for five min to allow complete cell lysis. All procedures were performed in the dark. Luminescence was measured by the Synergy4 Multi-detection microplate reader (BioTek, Winooski, VT) within 15 min of lysis.

b. Quantitative RT-PCR

Referring to FIG. 1A and FIG. 1B, SH-SY5Y neuroblastoma cells were treated with vehicle or compounds (1 μM) for 6 or 24 hours, and cells were collected for RNA isolation (Trizol method). Quantitative RT-PCR for Manganese superoxide dismutase (SOD2; FIG. 1A) or brain-derived neurotrophic factor (BDNF, exon 1; FIG. 1B) indicates short-term upregulation of SOD2 and BDNF and sustained upregulation of BDNF (n=3-4/group, one-way ANOVA followed by unpaired t-test; *p>0.05).

3. Data Supporting the Putative Mechanism of Action a. Induction of SOD2 Expression The initial high throughput screen and subsequent testing and analysis (see Manuvakhova et al. (2011) *Journal of neuroscience research* 89(1):58-72. PubMed PMID: 21046675. Pubmed Central PMCID: 3280078) revealed a number of compounds with potential biological activity. Two of these compounds, no. 1 and no. 2, increase SOD2 expression (FIG. 3A-C) and activity (FIG. 3D). Without wishing to be bound by theory, these compounds induce SOD2 in cells from different species (human, FIG. 3A; mouse, FIG. 3B; and rat, FIG. 3C and FIG. 3D), suggesting that these compounds could be used in mice to test potential target engagement and efficacy in humans.

Figures 3A, 3B:
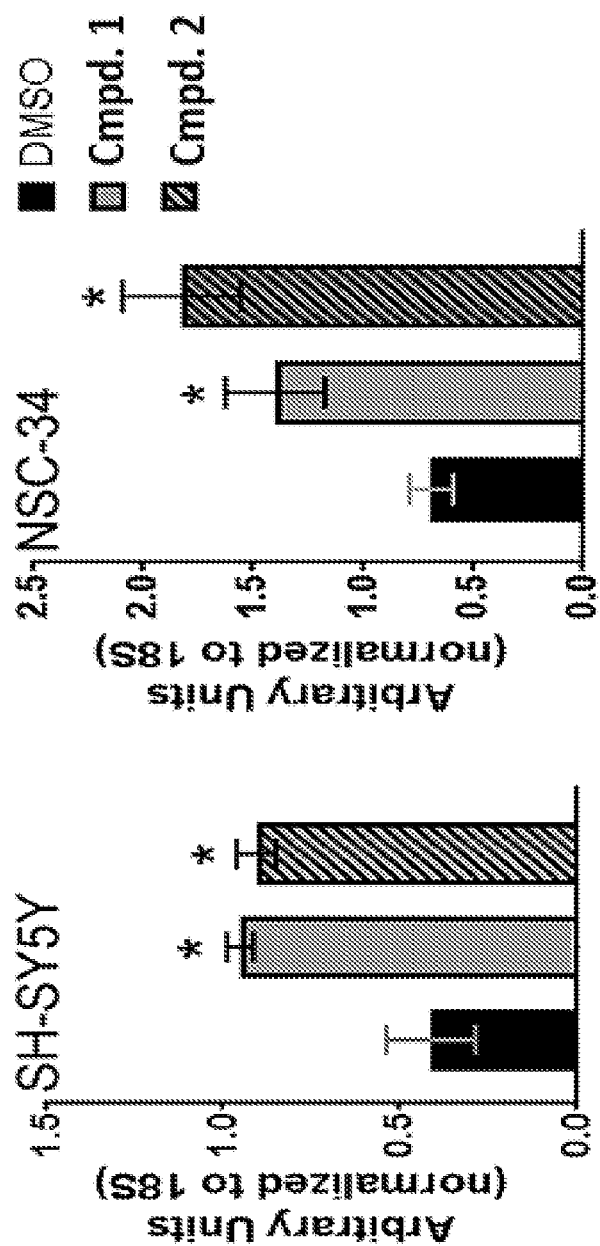
FIG. 3A-D show representative data demonstrating that the compound nos. 1 and 2 induced SOD2 expression and activity.
Figures 3C, 3D:
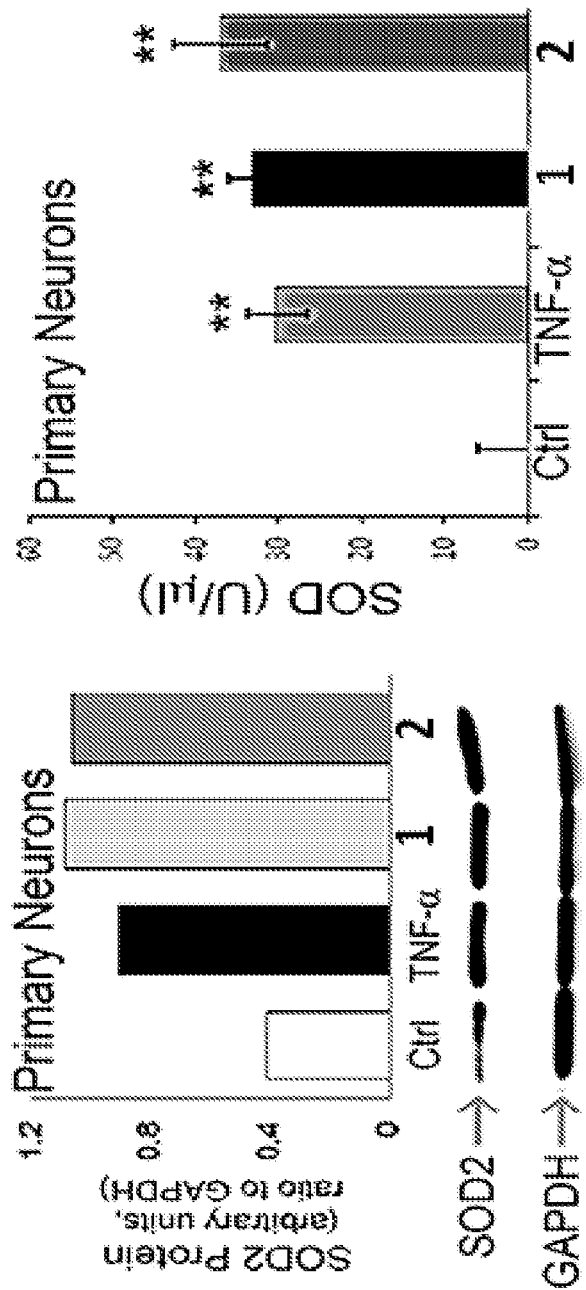

Referring to FIG. 3A and FIG. 3B, treatment of human SH-SY5Y neuroblastoma cells (6 h; FIG. 3A) or mouse NSC-34 neuroblastoma cells (24 h; FIG. 3B) with 1 μM compound significantly induced SOD2 mRNA expression as measured by quantitative RT-PCR.

Referring to FIG. 3C and FIG. 3D, exposure of primary rat cortical cultures to the compounds increased protein expression (FIG. 3C) and SOD activity (FIG. 3D). N=3-6/group, mean+/−SEM, *p<0.05, **p<0.01, 2-way ANOVA, post-hoc t-test.

b. NF-κB Activation for Promoting Neuroprotection

A number of studies have shown that the activation of the NF-kB complex in neurons can be neuroprotective (Sarnico et al. (2009) *International review of neurobiology* 85:351-62. PubMed PMID: 19607980; Kuntzen et al. (2007) *Methods in molecular biology* 399:99-124. PubMed PMID: 18309928; Kaltschmidt et al. (2005) *Biochimica et biophysica acta* 1745(3):287-99. PubMed PMID: 15993497) potentially by inducing genes like SOD2, the growth factor BDNF (Neidl et al. (2016) *The Journal of neuroscience: the official journal of the Society for Neuroscience* 36(15):4351-61. PubMed PMID: 27076430; Marini et al. (2004) *Restorative neurology and neuroscience* 22(2):121-30. PubMed PMID: 15272146), and the activity-dependent genes c-fos and egr-1 (Ho et al. (2009) *Current molecular pharmacology* 2(1):19-31. PubMed PMID: 20021442). However, in light of the role for NF-kB in pro-inflammatory transcriptional programs in leukocytes (Ahmed et al. (2015) *Biomolecules* 5(4):3087-111. PubMed PMID: 26569329. Pubmed Central PMCID: 4693271; Blaser et al. (2016) *Trends in cell* biology 26(4):249-61. PubMed PMID: 26791157), the generic activation of NF-kB could be detrimental in the context of neurodegeneration, potentially by increasing the expression of inhibitory kB (Ikiz et al. (2015) *Cell reports* 12(2):335-45. PubMed PMID: 26146077. Pubmed Central PMCID: 4646662). Importantly, previous studies showed that compounds in the same series as no. 1 and no. 2 increase SOD2 expression without changing the levels of inhibitory kB, are neuroprotective against glutamate-induced toxicity in primary cultures, and do not induce the expression of cytokines (Writing et al. (2017) *The Lancet Neurology* 16(7):505-12. PubMed PMID: 28522181). In all target engagement studies and ALS model studies, cytokine expression (in vitro and in vivo) and leukocyte phenotype will be evaluated to rule out any effects on activation of NF-kB in non-neuronal cells.

C. Initial Tests of Efficacy in the SOD1 G93A Transgenic Mouse

Figures 4A, 4B:
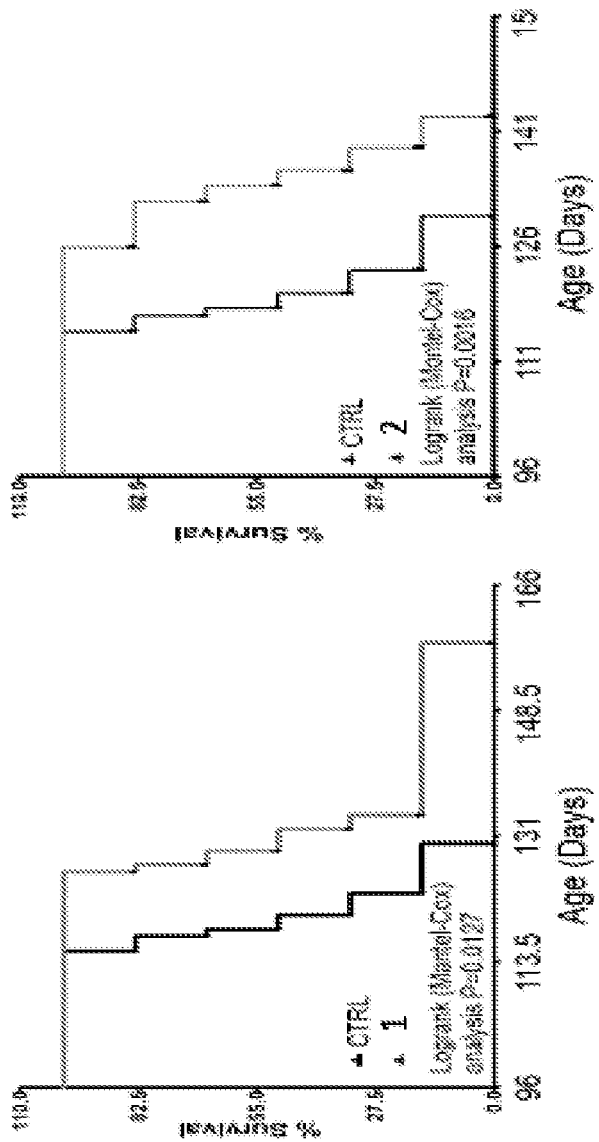
FIG. 4A-C show representative data demonstrating that compound no. 1 and compound no. 2 show potential efficacy in the SOD1 G93A transgenic model of ALS.
Figure 4C:
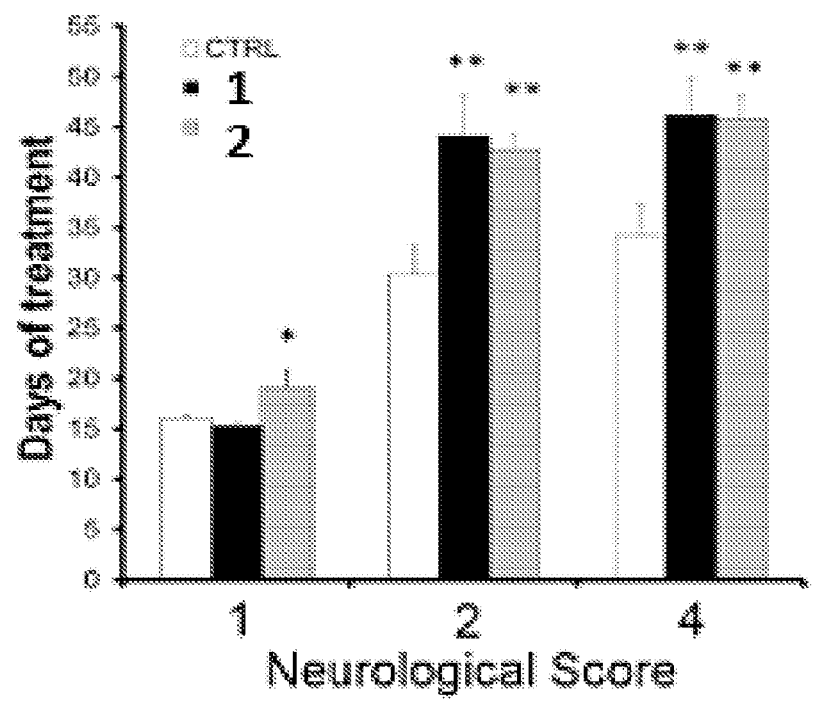

While compounds which increase SOD2 expression and activity have potential utility in a number of neurodegenerative diseases involving ROS overproduction, it was decided to test these two compounds in a mouse model of ALS for a variety of reasons, including the evidence for oxidative stress in ALS (described above), the ability of these compounds to induce SOD2 in a motor neuron-like mouse cell line (NSC-34; FIG. 3B), and the availability of a mouse model with dysfunction in SOD1 (human SOD1 G93A transgenic mouse; Jackson Laboratory). The pilot experiment involved treating six wildtype and six SOD1 G93A transgenic males on the C57BL/6 background with 25 mg/kg compound no. 1 and compound no. 2 I.P. daily, beginning around disease onset (day 96; FIG. 4A and FIG. 4B). Mouse survival and behavioral phenotype were observed based on guidelines from "Working with ALS mice: JAX handbook," using a 4-point severity score (FIG. 4C). Survival was significantly prolonged and progression to a score of 4 was delayed with both compounds, suggesting that further testing of the target engagement and efficacy of these compounds are warranted.

Referring to FIG. 4A and FIG. 4B, SOD1 G93A mice received daily IP injections of saline (control) or compounds (25 mg/kg) starting on day 96.

Referring. To FIG. 4C, progression from neurological score 1 was delayed only by compound no. 2 (2 day delay, +30%), progression to higher (worse) scores was delayed by both compounds. *P<0.05; **P<0.01, 2-way ANOVA.

Before the studies above were initiated, congenic SOD1 G93A mice were dosed with 50 mg/kg of compound no. 1 and compound no. 2 via I.P. injection to rule out any toxicity issues prior to initiating the efficacy study (FIG. 4A-C). The compounds were shown to achieve substantial plasma and brain levels within 30 minutes. However, one drawback of these compounds is their lack of oral bioavailability (I.V./P.O., 1 and 5 mg/kg, respectively) and very short plasma half-life ($t_{1/2}$<5 min), which was anticipated by lack of stability >20 minutes in microsomal stability studies. Therefore, daily I.P. injections of these two compounds will be used for proof-of-concept compounds for target engagement and efficacy studies, but they do not have the appropriate profiles for advancing to IND status.

4. Chemical Identities of Lead Compounds a. Initial Lead Compounds

The structures of the initial lead compounds have been published (1) and are shown in FIG. 4A-C. Before the studies above were initiated, congenic SOD1 G93A mice were dosed with 50 mg/kg of compound no. 1 and compound no. 2 via I.P. injection to rule out any toxicity issues prior to initiating the efficacy study (FIG. 4A-C). The compounds were shown to achieve substantial plasma and brain levels within 30 minutes. However, one drawback of these compounds is their lack of oral bioavailability (I.V./P.O., 1 and 5 mg/kg, respectively) and very short plasma half-life ($t_{1/2}$<5 min), which was anticipated by lack of stability >20 minutes in microsomal stability studies.

b. Identification of a Novel Compound Series

Figure 5:
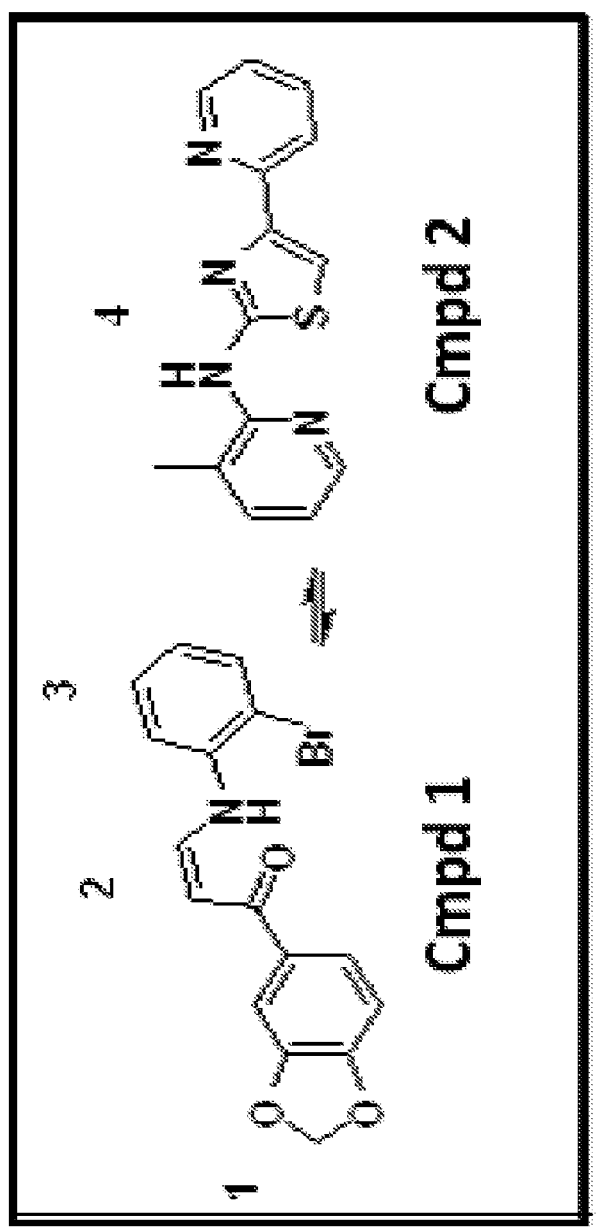
FIG. 5 shows the chemical structures of compound no. 1 and compound no. 2.

To identify compounds with similar activity but improved stability profiles, the structures of compound no. 1 and compound no. 2 were used as starting points. Examination of their structures revealed similarities to be exploited as well as structural alerts or liabilities that needed to be addressed. Liabilities included the benzodiol moiety (#1), enone group (#2) and aniline (#3) on compound no. 1 and the amino thiazole (#4) on compound no. 2 (FIG. 5), potential to chelate metals, and the fact that similar compounds were reported to be channel blockers (Skibsbye et al. (2015) *Journal of cardiovascular pharmacology* 66(2):165-76). The approaches herein include, for example, simple ring substitutions, elimination of the 1,3-dioxole and the aminothiazole, and elimination of the double bond found in compound no. 1.

c. This Approach Represents a Significant Breakthrough

The lead compound in the oxazole series is compound no. 40, ($EC_{50}$ of 2 µM, $E_{max}$ of 24, solubility of 56 µM and $t_{1/2}$ in HLM and MLM of 260 and 100 minutes, respectively). In addition, this compound was also orally bioavailable (16%) and had an I.V. $t_{1/2}$ of 1.4 hr. Initially, the role of the substituents at R4 and R5 were examined. Several of the esters were active and the activity was highly dependent upon the fluorine substitution pattern. Synthetic efforts have continued in this area and compounds with $EC_{50}$'s less than 1 µM, $E_{max}$>30 µM and no structural alerts have been identified (see Table 2 below). A number of these novel compounds were tested for their ability to induce SOD2 mRNA expression in SH-SY5Y cells (FIG. 6, below).

Figure 6:
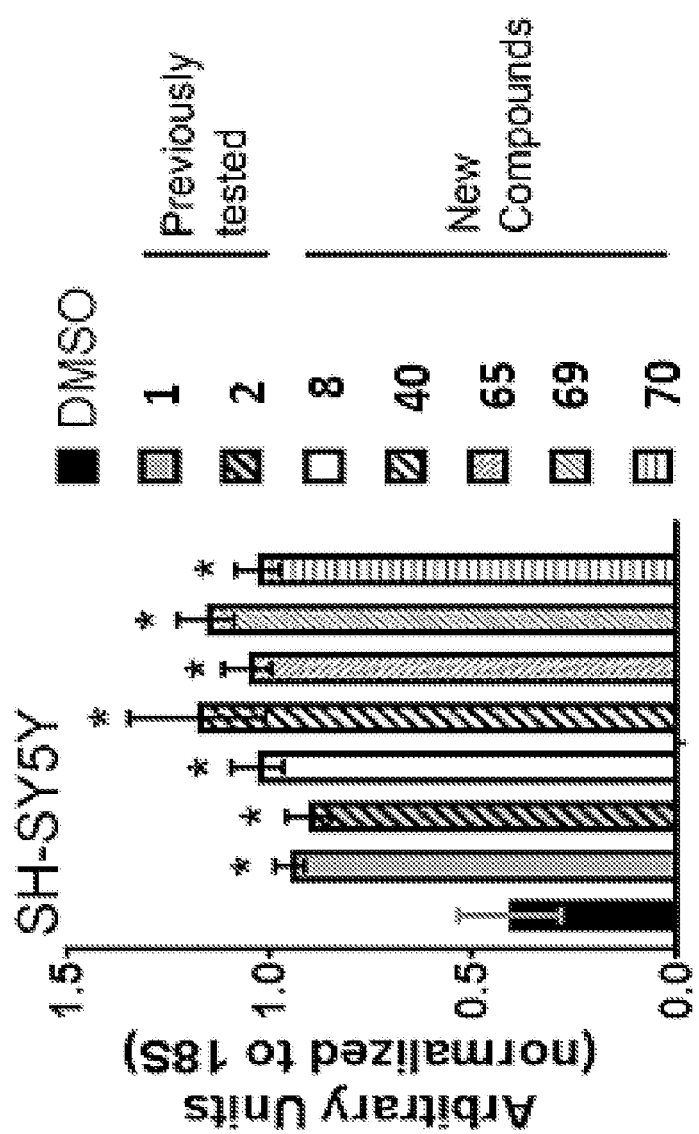
FIG. 6 shows representative data demonstrating that derivatives of compound no. 2 induce SOD2 mRNA expression.

Referring to FIG. 6, treatment of SH-SY5Y neuroblastoma cells with compounds (1 µM, 6 h) induced SOD2 mRNA expression >2 fold, as detected by q-RT-PCR. N=4/group, mean+/−SEM, 2-way ANOVA, post-hoc t-test. *p<0.05).

The synthesis reactions were performed under a dry argon atmosphere and reaction temperatures were measured externally. Anhydrous solvents and reagents from Aldrich were used without further drying. The reactions were monitored by thin-layer chromatography (TLC) on pre-coated silica gel ($60F_{254}$) aluminium plates (0.25 mm) from E. Merck and visualized using UV light (254 nm). Purification of all compounds was carried out by utilizing a Teledyne Isco Combiflash® Rf automated chromatography machine. Universal RediSep solid sample loading pre-packed cartridges were used to absorb crude product and purified on silica RediSep Rf Gold Silica (20-40 µm spherical silica) columns using appropriate solvent gradients. Pure samples were dried overnight under high vacuum over $P_2O_5$ at 78° C. before analyses. The exact mass spectral data were obtained with an Agilent LC-MSTOF or with Bruker BIOTOF II by electrospray ionization (ESI). $^1$HNMR spectra were recorded on an Agilent/Varian MR-400 spectrometer operating at 399.930 MHz. The chemical shifts (δ) are in ppm downfield from standard tetramethylsilane (TMS). Chemical shifts (δ) listed for multiplets were measured from the approximate centers, and relative integrals of peak areas agreed with those expected for the assigned structures. Determination of percent purity was obtained by HPLC using an Agilent 1100 LC equipped with a diode array UV detector and monitored at multiple wavelengths. ESI-MS spectra was recorded on a BioTof-2 time-of-flight mass spectrometer. The NMR data for various analogs are listed in Table 2, and the purity and microsomal stability data are listed in Table 1. None of the compounds had greater than 0.5% of a single impurity.

TABLE 1

| Compound No. | Purity (HPLC or LCMS) (%) | MS (M or M + H) |
|---|---|---|
| 1 | 99 | 346.0 |
| 40 | 98 | 298.07 |
| 61 | 100 | 330.08 |
| 65 | 96 | 312.12 |
| 69 | 99 | 330.08 |
| 70 | 99 | 330.09 |

5. In Vitro Biological Activity and Selectivity for the Intended Target a. Ability of Potential Lead Compounds to Increase SOD2 mRNA Expression In Vitro While a number of new compounds derived from Ataluren and compound no. 2 were shown to increase NF-kB reporter activity, it was next investigated whether they were capable of inducing SOD2 mRNA expression in vitro to the same extent as the original compounds, no. 1 and no. 2. It was found that all compounds tested (FIG. 6) increased SOD2 mRNA expression, similar to the original compounds (~2 fold, FIG. 3A-D). Whether these and other compounds are capable of inducing SOD2 mRNA and protein activity in vitro and in vivo, in addition to their ability to protect neurons from hydrogen peroxide or glutamate-induced cell death (as in Carri et al. (2015) Frontiers in cellular neuroscience 9:41) and dysfunction/cell death in the SOD1 G93A transgenic mouse model will also be evaluated.

b. The P65 Subunit of NF-κB as a Putative Direct Target of Novel Compounds

Figure 7:
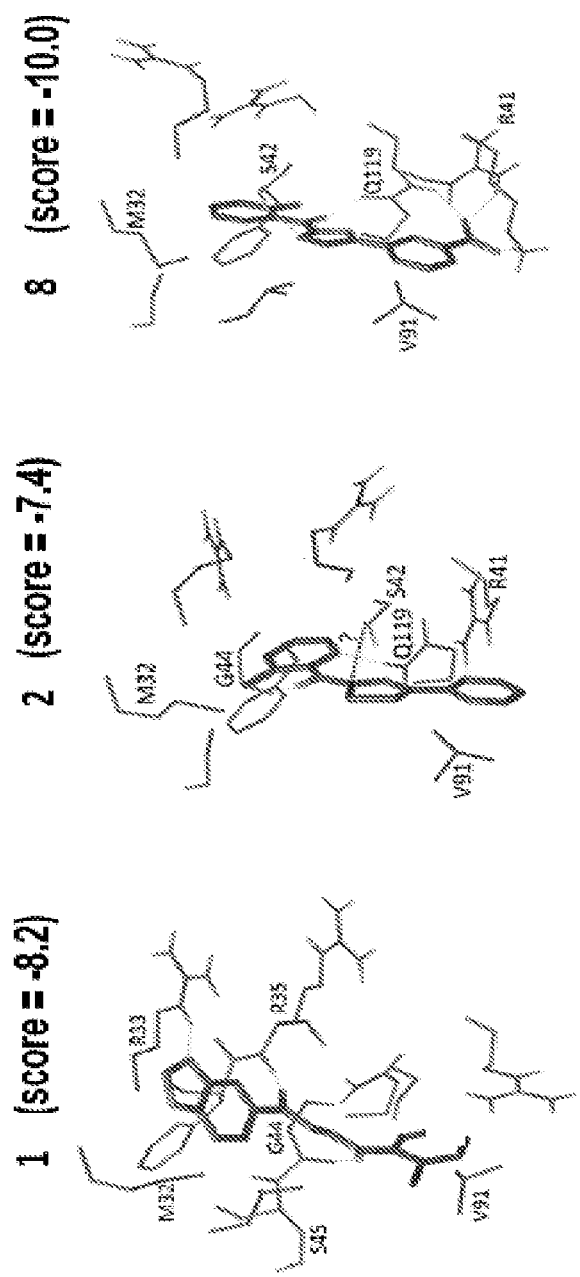
FIG. 7 shows representative computational models illustrating proposed interactions between critical residues of p65 and novel compounds.

Regarding the potential targets of these molecules, computational molecular docking experiments indicated that the compounds could be enhancing NF-κB activity by binding to the p65 subunit (Writing et al. (2017) *The Lancet Neurology* 16(7):505-12). The ability of compound no. 1 and compound no. 2 to interact with the p65/P50 region, the proposed target, were modeled using Induced Fit Docking approach from Schrödinger®. Small molecules were docked to crystal structures of p65/P50 heterodimers (PDB ID 1VKX, 1LE9, and 1NFI). SiteMap from Schrödinger® and results from previous modeling study (FIG. 7) (Manuvakhova et al. (2011) *Journal of neuroscience research* 89(1): 58-72) were used to predict potential binding sites. Both compounds demonstrate complementarity of polarity and shape with the surrounding residues, implying an ability to bind to the p65 region. Biolayer inferometry (BLI) studies will be performed to determine whether these compounds bind directly to p65.

6. Characterization of 2,5-aryl-oxazole analogs

Figure 16:
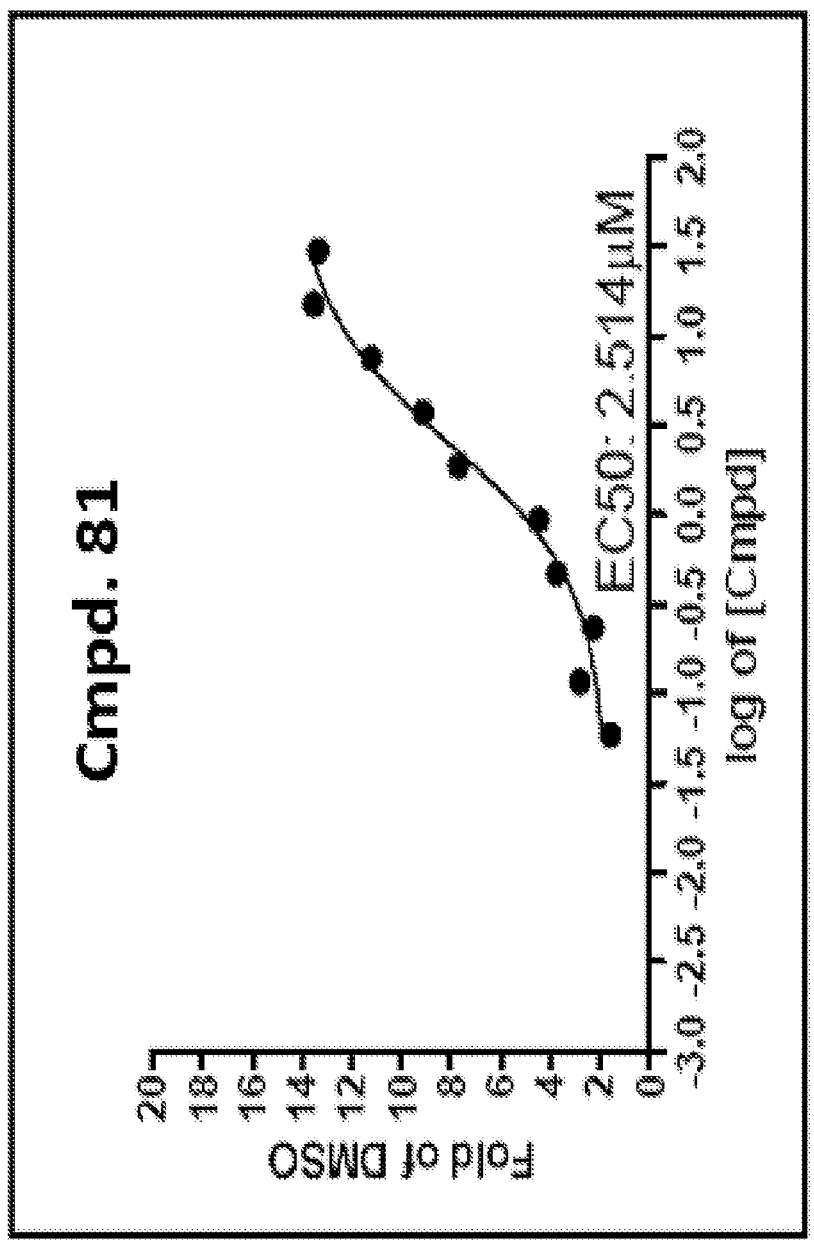
FIG. 16 shows a representative dose response curve for compound no. 81.

A list of compounds evaluated for activity is shown in Table 2 below. An exemplary dose response curve for compound no. 81 is shown in FIG. 16.

TABLE 2

| No. | Structure | Purity (HPLC or LCMS) | MS (M or M + H) | $EC_{50}$ | $E_{max}$ |
|---|---|---|---|---|---|
| 1 22818 | | 98 | 346 | 0.5 | 26 |
| 2 22819 | | 100 | 269.1 | 0.21 | 40 |
| 40 37328 | | 98.1 | 298.07 | 1.03 | 23.53 |
| 41 38875 | | 96.9 | 298.07 | 4.76 | 20.10 |

TABLE 2-continued

| No. | Structure | Purity (HPLC or LCMS) | MS (M or M + H) | $EC_{50}$ | $E_{max}$ |
|---|---|---|---|---|---|
| 42 38878 | | 96.5 | 298.07 | 6.67 | 30.38 |
| 44 38996 | | 95.1 | 316.06 | >10 | 5.94 |
| 45 38997 | | 96.4 | 316.06 | 1.60 | 26.44 |
| 46 38998 | | 100 | 316.06 | 2.92 | 25.50 |
| 47 39441 | | 99.7 | 316.06 | 3.27 | 46.45 |
| 48 39442 | | 99.3 | 334.05 | >10 | 14.13 |
| 49 39447 | | 96.3 | 298.07 | >10 | 10.21 |

TABLE 2-continued

| No. | Structure | Purity (HPLC or LCMS) | MS (M or M + H) | $EC_{50}$ | $E_{max}$ |
|---|---|---|---|---|---|
| 50 39448 | | 96.2 | 298.07 | Inactive | 6.15 |
| 51 39449 | | 99.4 | 298.07 | Inactive | 4.22 |
| 52 39453 | | 96.4 | 316.06 | 5.60 | 11.64 |
| 53 39454 | | 98.5 | 316.06 | Inactive | |
| 54 39464 | | 99.8 | 298.07 | Inactive | 5.37 |
| 55 39461 | | 99.2 | 316.06 | Inactive | 4.46 |
| 56 37326 | | 98.8 | 312.09 | >10 | 3.19 |

TABLE 2-continued

| No. | Structure | Purity (HPLC or LCMS) | MS (M or M + H) | $EC_{50}$ | $E_{max}$ |
|---|---|---|---|---|---|
| 57 38874 | 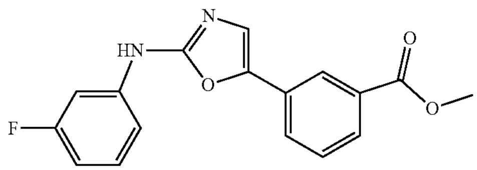 [SMILES: COC(=O)c1cccc(-c2cnc(Nc3cccc(F)c3)o2)c1] | 100 | 312.09 | 0.41 | 17.20 |
| 58 38873 | 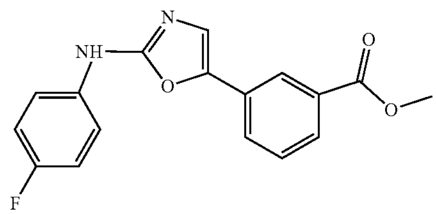 [SMILES: COC(=O)c1cccc(-c2cnc(Nc3ccc(F)cc3)o2)c1] | 100 | 312.09 | 1.29 | 24.34 |
| 59 38877 | 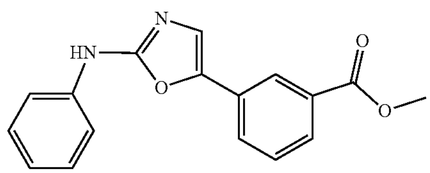 [SMILES: COC(=O)c1cccc(-c2cnc(Nc3ccccc3)o2)c1] | 98.4 | 294.10 | 0.20 | 14.46 |
| 60 38881 | 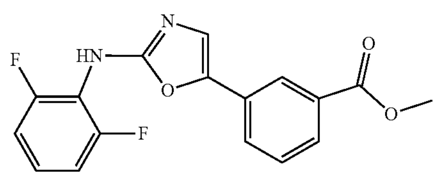 [SMILES: COC(=O)c1cccc(-c2cnc(Nc3c(F)cccc3F)o2)c1] | 98.9 | 330.08 | 2.06 | 19.78 |
| 61 38883 | 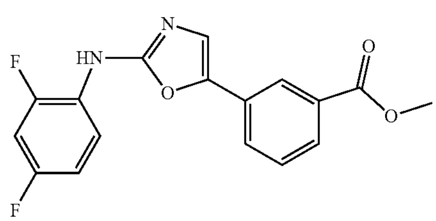 [SMILES: COC(=O)c1cccc(-c2cnc(Nc3ccc(F)cc3F)o2)c1] | 100 | 330.08 | 0.37 | 9.08 |
| 62 38884 | 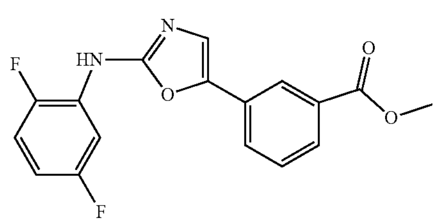 [SMILES: COC(=O)c1cccc(-c2cnc(Nc3cc(F)ccc3F)o2)c1] | 99.05 | 330.08 | 0.18 | 7.64 |
| 63 39439 | 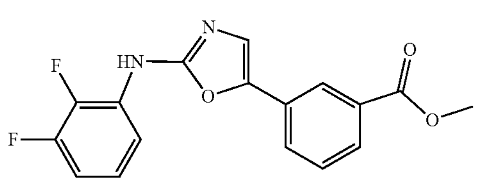 [SMILES: COC(=O)c1cccc(-c2cnc(Nc3cccc(F)c3F)o2)c1] | 98.6 | 330.08 | 3.41 | 8.60 |

TABLE 2-continued

| No. | Structure | Purity (HPLC or LCMS) | MS (M or M + H) | $EC_{50}$ | $E_{max}$ |
|---|---|---|---|---|---|
| 64 39440 | 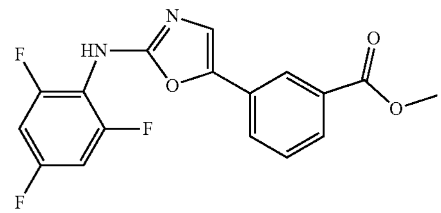 [SMILES: COC(=O)c1cccc(-c2cnc(Nc3c(F)cc(F)cc3F)o2)c1] | 99.2 | 348.07 | >10 | 12.31 |
| 65 39444 | 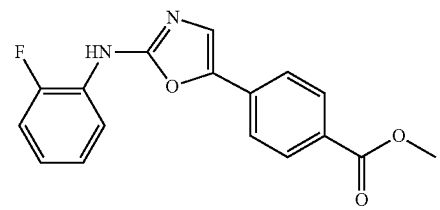 [SMILES: COC(=O)c1ccc(-c2cnc(Nc3ccccc3F)o2)cc1] | 95.0 | 312.09 | 1.20 | 63.18 |
| 66 39445 | 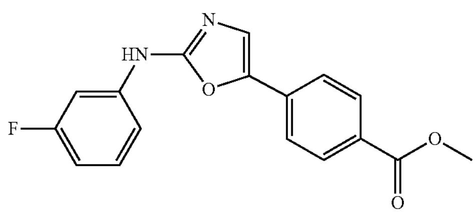 [SMILES: COC(=O)c1ccc(-c2cnc(Nc3cccc(F)c3)o2)cc1] | 99.0 | 312.09 | >10 | 6.71 |
| 67 39446 | 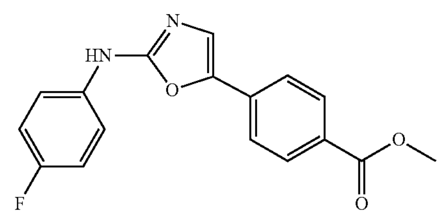 [SMILES: COC(=O)c1ccc(-c2cnc(Nc3ccc(F)cc3)o2)cc1] | 96.7 | 312.09 | Inactive | |
| 68 39450 | 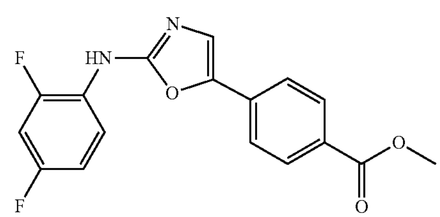 [SMILES: COC(=O)c1ccc(-c2cnc(Nc3ccc(F)cc3F)o2)cc1] | 98.12 | 330.08 | >10 | 4.41 |
| 69 39451 | 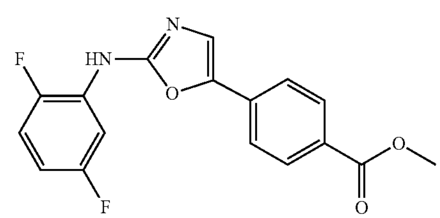 [SMILES: COC(=O)c1ccc(-c2cnc(Nc3cc(F)ccc3F)o2)cc1] | 99.2 | 330.08 | 0.40 | 34.11 |
| 70 39452 | 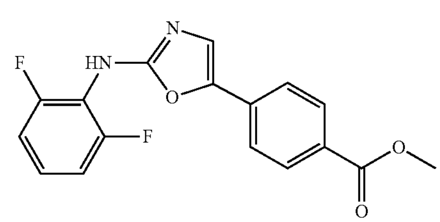 [SMILES: COC(=O)c1ccc(-c2cnc(Nc3c(F)cccc3F)o2)cc1] | 98.9 | 330.08 | 0.16 | 42.48 |

TABLE 2-continued

| No. | Structure | Purity (HPLC or LCMS) | MS (M or M + H) | $EC_{50}$ | $E_{max}$ |
|---|---|---|---|---|---|
| 71 39463 | 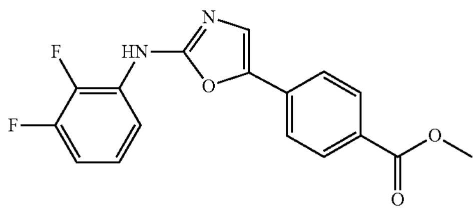 [SMILES: COC(=O)c1ccc(-c2cnc(Nc3cccc(F)c3F)o2)cc1] | 98.5 | 330.08 | Inactive | 7.24 |
| 72 39462 | 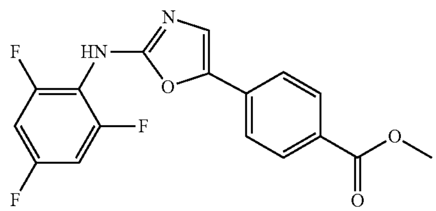 [SMILES: COC(=O)c1ccc(-c2cnc(Nc3c(F)cc(F)cc3F)o2)cc1] | 98.7 | 348.07 | Inactive | 3.97 |
| 73 39455 | 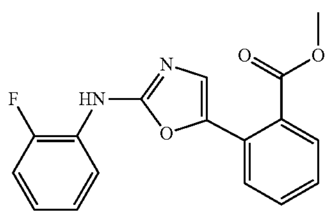 [SMILES: COC(=O)c1ccccc1-c1cnc(Nc2ccccc2F)o1] | 99.8 | 312.09 | Inactive | 2.37 |
| 74 39456 | 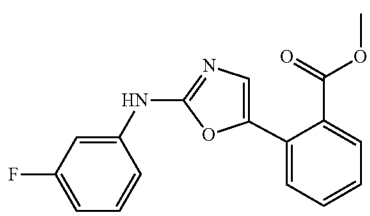 [SMILES: COC(=O)c1ccccc1-c1cnc(Nc2cccc(F)c2)o1] | 99.7 | 312.09 | Inactive | 2.37 |
| 75 39457 | 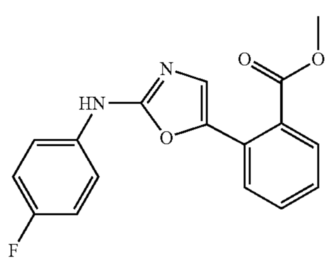 [SMILES: COC(=O)c1ccccc1-c1cnc(Nc2ccc(F)cc2)o1] | 96.4 | 312.09 | Inactive | 2.97 |
| 76 39458 | 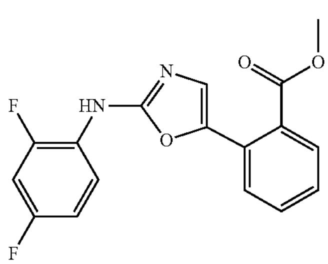 [SMILES: COC(=O)c1ccccc1-c1cnc(Nc2ccc(F)cc2F)o1] | 98.7 | 330.08 | Inactive | 4.45 |

TABLE 2-continued
| No. | Structure | Purity (HPLC or LCMS) | MS (M or M + H) | EC$_{50}$ | E$_{max}$ |
|---|---|---|---|---|---|
| 77 39459 | 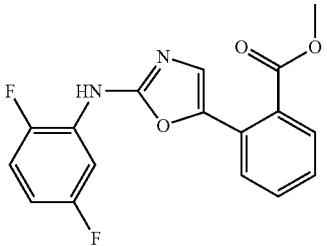 [SMILES: COC(=O)c1ccccc1-c1cnc(Nc2cc(F)ccc2F)o1] | 100 | 330.08 | Inactive | 2.29 |
| 78 39460 | 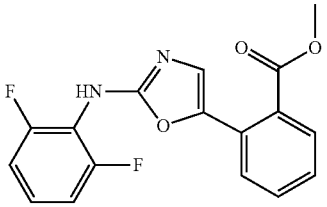 [SMILES: COC(=O)c1ccccc1-c1cnc(Nc2c(F)cccc2F)o1] | 100 | 330.08 | Inactive | 4.36 |
| 79 39438 | 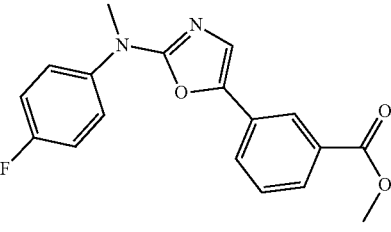 [SMILES: COC(=O)c1cccc(-c2cnc(N(C)c3ccc(F)cc3)o2)c1] | 99.7 | 326.11 | 2.58 | 28.56 |
| 81 36400 | 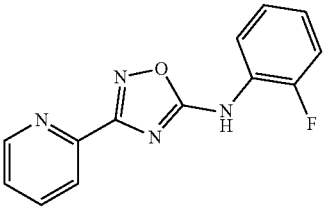 [SMILES: Fc1ccccc1Nc1nc(-c2ccccn2)no1] | 98.0 | 256.07 | 2.51 | 14.44 |
| 82 39968 | 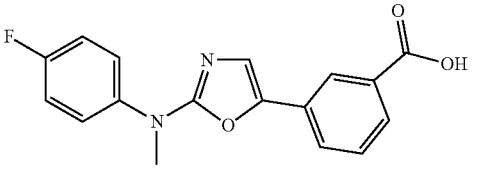 [SMILES: CN(c1ccc(F)cc1)c1ncc(-c2cccc(C(=O)O)c2)o1] | 99.7 | 312.09 | 2.16 | 36.85 |
| 83 40113 | 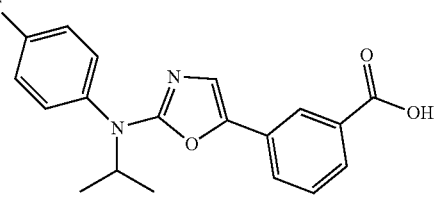 | 98.7 | 340.12 | Inactive | 4.50 |
| 84 40141 | 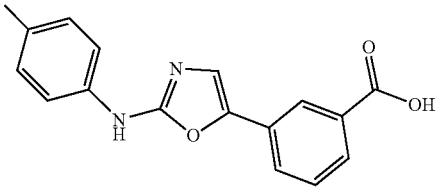 | 99.4 | 314.04 | 0.75 | 11.26 |

TABLE 2-continued
| No. | Structure | Purity (HPLC or LCMS) | MS (M or M + H) | EC$_{50}$ | E$_{max}$ |
|---|---|---|---|---|---|
| 85 39952 | 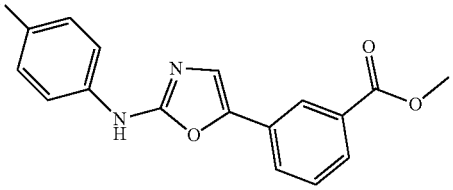 | 100 | 328.06 | Inactive | 5.77 |
| 86 40029 | 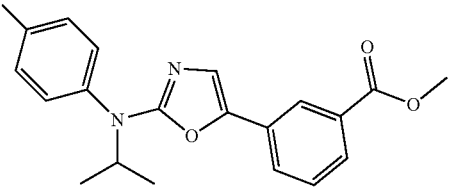 | 97.9 | 354.13 | Inactive | 2.2 |
| 87 40030 | 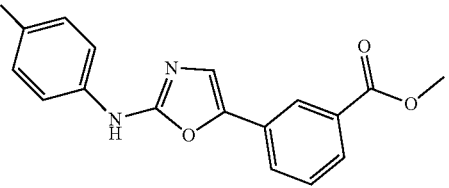 | 100 | 362.08 | Inactive | 5.29 |
| 88 40139 | 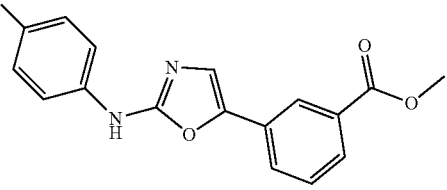 | 99.3 | 319.09 | Inactive | 3.49 |
| 89 40140 | 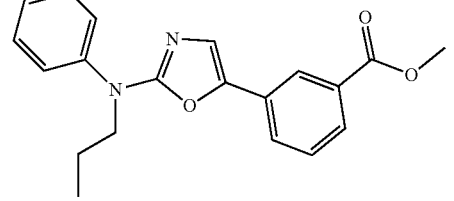 | 98.7 | 354.13 | Inactive | 3.00 |
| 90 41430 | 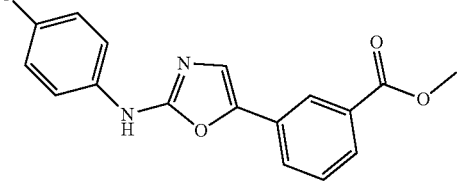 | 100 | 324.11 | Inactive | 2.47 |
| 91 39958 | 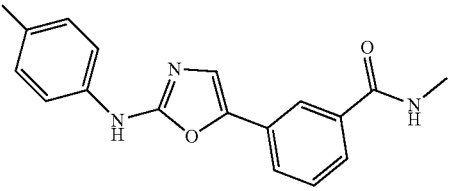 | 100 | 311.10 | 1.93 | 17.44 |

TABLE 2-continued

| No. | Structure | Purity (HPLC or LCMS) | MS (M or M + H) | EC$_{50}$ | E$_{max}$ |
|---|---|---|---|---|---|
| 92 40115 | 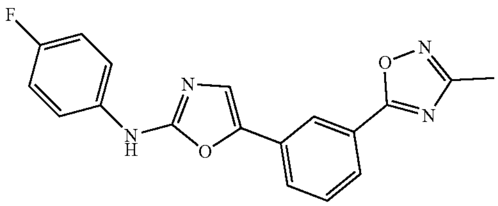 [SMILES: Cc1noc(-c2cccc(-c3cnc(Nc4ccc(F)cc4)o3)c2)n1] | 99.8 | 336.10 | 7.15 | 18.09 |
| 93 41154 | 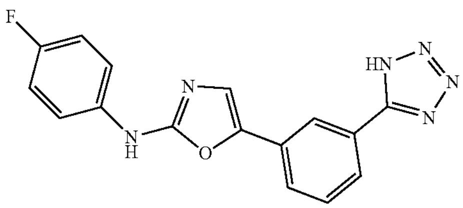 [SMILES: Fc1ccc(Nc2ncc(-c3cccc(-c4nnn[nH]4)c3)o2)cc1] | 99.25 | 322.09 | Inactive | 2.59 |
| 94 41155 | 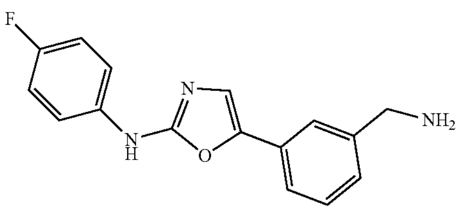 [SMILES: NCc1cccc(-c2cnc(Nc3ccc(F)cc3)o2)c1] | 99.26 | 283.11 | 0.71 | 20.15 |
| 95 41159 | 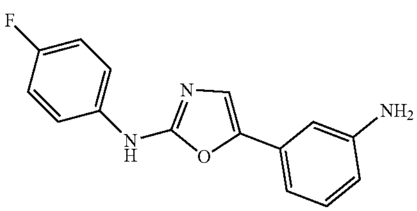 [SMILES: Nc1cccc(-c2cnc(Nc3ccc(F)cc3)o2)c1] | 99.40 | 269.09 | 3.83 | 15.76 |
| 96 41427 | 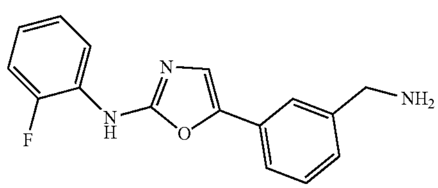 [SMILES: NCc1cccc(-c2cnc(Nc3ccccc3F)o2)c1] | 100 | 283.11 | Inactive | 5.14 |
| 97 41770 | 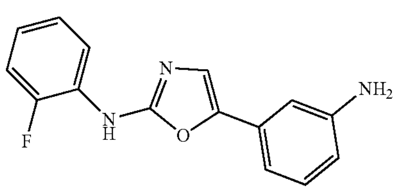 [SMILES: Nc1cccc(-c2cnc(Nc3ccccc3F)o2)c1] | 96.99 | 269.09 | Inactive | 0.55 |
| 98 40216 | 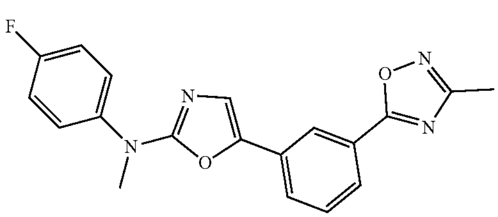 [SMILES: Cc1noc(-c2cccc(-c3cnc(N(C)c4ccc(F)cc4)o3)c2)n1] | 99.52 | 350.11 | Inactive | 3.2 |

TABLE 2-continued

| No. | Structure | Purity (HPLC or LCMS) | MS (M or M + H) | $EC_{50}$ | $E_{max}$ |
|---|---|---|---|---|---|
| 99 40337 | 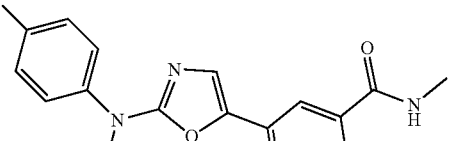 | 100 | 352.12 | 4.89 | 19.72 |
| 100 36884 | 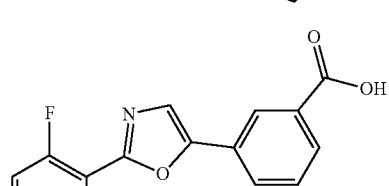 | 97.8 | 284.1 (M + H) | 2.55 | 15.01 |

H. Prophetic Examples

1. In Vivo PK Assay

The experiments will involve the administration of compounds to 5-6 week old CD1 male mice. Mice are dosed by either a 1 mg/kg IV bolus or 5 mg/kg oral gavage. Blood samples are collected by cardiac puncture at 0, 0.25, 0.5, 1, 2, 4, 6, 8, 12, and 24 hrs. There will be three mice per time point. Plasma concentration over time will be determined by LC/MS from which the standard PK parameters of clearance, volume of distribution, $t_{1/2}$ and % F can be derived using WinNoLin software (Pharsight Inc.). This will require a total of 60 mice per compound. Plasma will be analyzed by reverse phase chromatography with MS/MS detection operating in the positive ion mode using multiple reaction monitoring using an internal standard and Applied Biosystems Analyst 1.4 software. Peak time (when maximum plasma drug concentration occurs), peak drug level [approximate maximum concentrations of drug in plasma ($C_{max}$)] and $t_{1/2}$ for drug elimination will be estimated for each tested compound. Bioavailability (F) will be calculated from the ratio of $AUC_{PO}/AUC_{IV}$ and expressed as a percentage. To determine levels in brain, six additional mice will be dosed with 1 mg/kg I.V. and sacrificed at 0.25 and 1 hr. Brain and spinal cord samples will be collected at these two time points, quick frozen in an ice box and kept at −75±15° C. All samples will be weighed and homogenized with phosphate buffered saline (PBS) by brain weight (g) to PBS volume (mL) ratio 1:3 before analysis. The actual concentration is the detected value multiplied by the dilution factor.

2. In Vitro ADME Assay

A standard panel of in vitro ADME assays will be utilized to assess drug-like properties of compounds and to inform subsequent in vivo PK studies. These assays include: (a) Permeability: MDCK (Madin Darby Canine Kidney) cells transfected with the MDR1 gene encoding for the multi-drug resistant transporter (Pgp) will be utilized to determine a compound's ability to permeate the membrane in apical to basolateral (A-B) and basolateral to apical (B-A) directions. The derived apparent permeability coefficient (Papp) provides an estimate of passive permeability; a ratio of Papp in the B-A/A-B direction gives an estimate of transporter efflux; (b) Solubility: Kinetic solubility is an important parameter for accurate determinations of the dose response. This is estimated using the shake flask method with a pSol Explorer (PION, Billerica, MA) at pH 7.4. Compounds are added as a DMSO solution to buffer. The average of two determinations at pH 7.4 will be reported. Solubility at pH 7.4 is relevant for in vitro assays; (c) Metabolic Stability: The potential for a high metabolic clearance compound is estimated using a liver microsome assay. The compounds are incubated in human and mouse liver microsomes with the co-factor NADPH which has oxidative, esterase and protease metabolic activity. The disappearance of the parent molecule is measured by liquid chromatography/mass spectroscopy (LC/MS) detection. Stability of the parent compound is reported as half-life.

3. Biolayer Interferometry (BLI)

To determine whether the new and previously identified compounds bind directly to p65 or other members of the NF-κB complex, BLI will be used. The compounds will be evaluated for binding affinity to recombinant p65 by BLI, by measuring the changes in association rate with increasing concentration of the molecules. BLI studies will be performed on an OctetRed (Pall ForteBio) with anti-penta-His labeled dip-and-read biosensors. Recombinant p65 (Acro Biosystems) will be loaded onto the biosensors at a concentration of 8 μg/mL. Loading will be done for 300 seconds, followed by a baseline reading then an association reading for 300 seconds followed by a 600-second dissociation reading. Amounts of each compound will range in concentration from 2 μM to 0.024 μM in 3:1 serial dilutions for initial binding experiments and 120-1.25 μM for inhibition studies. Binding data will be analyzed using the Octet software analysis system. For inhibition studies, peptide concentration will be varied while protein concentration will be held constant. BLI allows for a calculation of binding coefficients by measuring the difference in interference signal with and without bound ligand. Validation of the system will be done by determining the binding coefficient of recombinant p65 with candidate compounds. His-p65 will be immobilized on an anti-His biosensor at a fixed concentration.

4. SOD Assay

Superoxide dismutase activity will be evaluated in brain, spinal cord, serum, and cell culture using the SOD activity assay kit from Cayman Chemical (Ann Arbor, MI).

5. Docking Studies

The docking of compounds to p65 will be predicted as reported in (Manuvakhova et al. (2011) *Journal of neuroscience research* 89(1):58-72. PubMed PMID: 21046675. Pubmed Central PMCID: 3280078). Compounds will be prepared using LigPrep (Schrödinger®) and docked to mouse and human P65 and P50 using the induced-fit docking (IFD) protocol implemented in Schrödinger small molecule discovery suite (version 2015). Targets for docking are prepared from available crystal structures (1VKX for mouse P65, 1LE9 for mouse P50, and 3GUT for human P65 and P50). Binding sites are defined based on previous study (Manuvakhova et al. (2011) *Journal of neuroscience research* 89(1):58-72. PubMed PMID: 21046675. Pubmed Central PMCID: 3280078) and prediction from SiteMap (Schrödinger®). Both virtual binding modes and IFD scores were examined.

6. ALS Model, Genotyping, and Mouse Colony Maintenance

Wildtype mice (background matched to G93A transgenic line) for target engagement studies will be purchased from JAX 2-4 weeks before initiation of the study. Male SOD1 G93A transgenic mice (C57BL/6 background; JAX: 004435) will be purchased from JAX and bred with wildtype females (trio breeding) to produce experimental mice (transgenics and littermate controls). All experiments will involve equal numbers of males and females. Offspring will be genotyped with assistance by Dr. Cat Lutz (JAX) to evaluate transgene copy number (and avoid use of mice which have reduced copy number below 20). Females will be replaced after giving birth to 3-4 litters.

7. SH-SY5Y, NSC-34, THP-1, Primary Neuronal, and Primary Astrocyte Cultures

SH-SY5Y neuroblastoma cells (ATCC) will be cultured as previously described (Cowell et al. (2009) *Biochemical and biophysical research communications* 379(2):578-82. PubMed PMID: 19118529. Pubmed Central PMCID: 2656381) and the ability of compounds to protect them from hydrogen peroxide-induced toxicity will be determined by MTT viability assays (24 hours post-treatment) and Western blotting for activated caspase 3 (6 hours post-treatment). Cultures will be treated with different doses of the compounds to determine the $EC_{50}$ for neuroprotection for each compound; parallel cultures will be treated for q-RT-PCR analysis of SOD2 mRNA expression to determine the extent of target engagement required for neuroprotection. Mouse primary neuronal cultures will be prepared from embryonic day 18 mice, cultured on coverslips or in 48/96 well plates for immunofluorescence/q-RT-PCR or cell viability assays, respectively. Vulnerability to glutamate or hydrogen peroxide in the presence of the compounds will be assessed with the MTT assay, and oxidative stress and mitochondrial depolarization will be visualized and quantified as in (Berent-Spillson and Russell (2007) *Journal of neurochemistry* 101(2):342-54. PubMed PMID: 17402968). Induction of SOD2 mRNA and protein will be assessed using q-RT-PCR and Western blotting. Blockade of caspase 3 activation will be assessed with immunofluorescence. The identity of cell types expressing SOD2 will be determined using double-labeling immunofluorescence with markers for excitatory (CaMKII) or inhibitory neurons (GAD67). The monocytic cell line (THP-1) or primary astrocyte cultures will be dosed with different concentrations of the compounds to determine whether they cause p65 nuclear translocation (immunofluorescence) or pro-inflammatory cytokine expression (TNF-α, IFN-γ, IL-1β). All cell culture experiments will be performed in triplicate. RT-PCR experiments will be performed with sample sizes of 6-8/group, and the analysis of immunocytochemistry and mitochondrial/oxidative stress experiments will include >20 cells per condition (relative intensity measurements using Image J). Statistics will be performed using Prism, with initial analysis by 2-way ANOVA and post-hoc two-tailed t-tests, if data is distributed in a normal fashion. If data are not normally distributed, a non-parametric test (Kruskal-Wallis) will be performed.

8. Western Blotting

Protein content in cell culture and brain will be semi-quantitatively assessed with antibodies raised against SOD2 (Abcam), activated caspase 3 (Cell Signaling) using secondary antibodies conjugated to infrared fluorophores (Invitrogen) and detected using the ChemiDocMP imaging system.

9. SM-FISH

Brain and lumbar spinal cord will be dissected rapidly on ice and frozen with powdered dry ice and stored at −80° C. for sectioning on a cryostat. Tissue sections (30 μm) will be collected on charged slides and returned to −80° C. until use. mRNA will be localized to specific cell types using multiplex single-molecule fluorescent in situ hybridization (SM-FISH, RNAscope; ACDbio, Newark, CA) and quantified with Image J, with normalization to same-cell actin beta expression. To identify the cellular location of expression, probes for choline acetyltransferase (ChAT; motor neurons) or post-hoc immunostaining for glial fibrillary acidic protein (GFAP; Sigma; astrocytes) or Iba-1 (DAKO; microglia) will be used. Inventoried SM-FISH probes will be purchased from ACD-BIO for SOD2, p65, ChAT, and BDNF exon 9 (as another NF-kB-dependent gene). The percentage of ChAT, GFAP, or Iba-1-positive cell bodies occupied by SM-FISH SOD2 signal will be normalized to the amount of signal for actin R in the same cell, with the analysis of >100 cells in the ventral horn of six sections of lumbar spinal cord (n=8 mice/group).

10. NMJ Analysis

Figure 2:
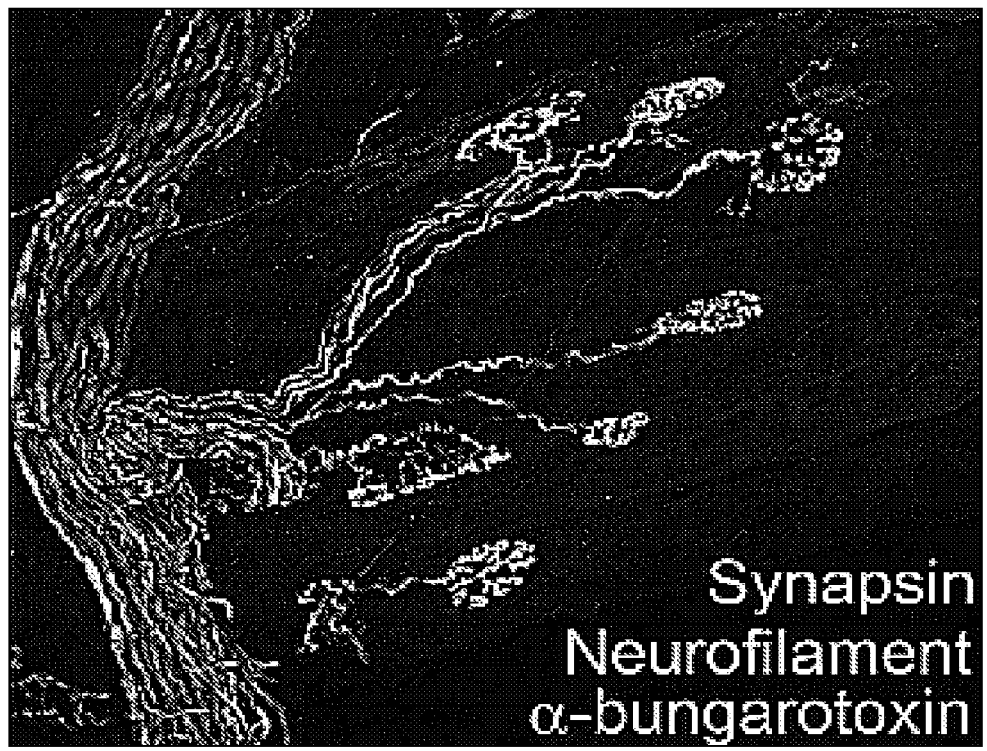
FIG. 2 shows representative staining of neuromuscular junctions to visualize structure and reconstruct images with confocal microscopy.

Fresh mount neuromuscular junctions will be isolated from tibialis anterior (TA) muscle (nerve and associated muscle) and drop-fixed in 4% paraformaldehyde as in Si et al. (2015) *PloS one* 10(9):e0138425. PubMed PMID: 26375954. Pubmed Central PMCID: 4574401; FIG. 2). The extent of colocalization of synaptic markers (synapsin, neurofilament) with fluorescently-tagged bungarotoxin will indicate the integrity of the NMJ (Chen et al. (2009) *The Journal of neuroscience: the official journal of the Society for Neuroscience* 29(35):10909-19. PubMed PMID: 19726649. Pubmed Central PMCID: 2766780). Primary antibodies include the neurofilament sampler kit #9781 and synapsin 1/D12G5, Cell Signaling Technology, Danvers, MA, USA, and fluorescently tagged secondary antibodies from Invitrogen. Preparation of coverslips for confocal microscopy requires ProLong Diamond Antifade Mountant with DAPI (Molecular Probes, Eugene, OR, USA). Z-stacks will be collected at 0.4 m throughout the entirety of the NMJ using a Leica TCS-SP5 laser-scanning confocal microscope and brightness will be adjusted for each NMJ individually to such that pixel intensity, as observed using the Leica LASAF software, does not surpass saturation. Qualitative analysis will be performed as described in (Vaden et al. (2015) *Frontiers in molecular neuroscience* 8:11. PubMed PMID: 25954152. Pubmed Central PMCID: 4407586). NMJ can be qualitatively assessed for terminal swelling and sprouting and quantified by percent total. Endplate area can be determined by tracing the circumference of α-bungarotoxin immunoreactivity and computing area via ImageJ analysis (NIH, Bethesda, MD, USA). Additionally, innervation of the NMJ will be categorized as complete, partial or denervated by whether synaptic markers are present at sites of α-bungarotoxin immunoreactivity throughout the entirety of the Z-stack as depicted in (Martin et al. (2015) *Journal of visualized experiments: JoVE* 25(99):e52605. PubMed PMID: 26066371. Pubmed Central PMCID: 4542903).

11. Flow Cytometry

To investigate whether the compounds affect the inflammatory state of peripheral blood leukocytes, multi-parameter flow cytometry will be used on peripheral blood cells isolated from trunk blood collected at the time of decapitation for the collections of brain and spinal cord tissue. Lineage marker analysis will be used to define the maturation/activation state and relative abundance of various cell populations, in addition to evaluating the expression of the pro-inflammatory cytokines TNF-α, IFN-γ, and IL-1β (Periasamy et al. (2016) *PLoS pathogens* 12(3):e1005517. PubMed PMID: 27015566. Pubmed Central PMCID: 4807818). An aliquot of blood/peripheral leukocytes will be collected for evaluation of SOD2 mRNA expression.

12. Immunofluorescence/Confocal Microscopy

Mice will be intracardially perfused with 4% paraformaldehyde in PBS, and brain, spinal cord, and sciatic nerves will be removed and post-fixed overnight before cryopreserving and freezing for sectioning on a sliding microtome (brain, spinal cord) or vibratome (sciatic nerve). Next, it will be determined whether the compounds increase the translocation or abundance of the NF-κB subunit p65 in the nucleus of motor neurons and/or other cells with double-labeling immunofluorescent labeling with antibodies raised against ChAT, GFAP, or Iba-1 (Philips and Rothstein (2015) *Current protocols in pharmacology* 69:5, 67:1-21. PubMed PMID: 26344214. Pubmed Central PMCID: 4562058).

13. Motor Neuron Stereology

Lumbar motor neurons will be quantified using stereology, as in Nardo et al. (2016) *Brain pathology* 26(2):237-47. PubMed PMID: 26780365, in serial sections stained with cresyl violet or ChAT, to avoid bias from changes in the expression of ChAT.

14. Sciatic Nerve Electron Microscopy (EM)

Sciatic nerves will be removed from fixed mice (above) and drop-fixed overnight in 1% glutaraldehyde and 4% paraformaldehyde before embedding, thin sectioning, staining, and imaging for EM (Vaden et al. (2015) *Frontiers in molecular neuroscience* 8:11. PubMed PMID: 25954152. Pubmed Central PMCID: 4407586). G-ratios will be calculated to determine whether demyelination is prevented by the compounds (Si et al. (2014) *Annals of clinical and translational neurology* 1(10):778-87. PubMed PMID: 25493269. Pubmed Central PMCID: 4241805).

15. CMAP

CMAP measures will be performed once, under isoflurane anesthesia, prior to death as in (Xia et al. (2010) *Muscle & nerve* 41(6):850-6. PubMed PMID: 20151466; Bogdanik et al. (2015) *Proceedings of the National Academy of Sciences of the United States of America* 112(43):E5863-72. PubMed PMID: 26460027. Pubmed Central PMCID: 4629342). Sciatic nerve will be stimulated either distal or proximal to the recording site (ankle), and amplitude will be measured and conduction velocity calculated. Comparison groups will be SOD1 G93A mutant mice and littermate controls (Wilcoxon's rank sum test for non-parametric variables, with significance set at P<0.05). A Pearson's chi-square test was used to determine significance between categorical variables, with significance set at P<0.05.

16. Motor Behavioral Analyses

General neurological status will be evaluated using the scoring system used for the SOD1 G93A mouse model ("Working with ALS mice: JAX handbook"), with the maximum score of 4 being assigned when the mouse is incapable of righting itself after 15-30 seconds (at which point the mouse is euthanized). Progression of decline will be monitored by weighing mice weekly and assessing performance on rotarod after the initial training period (day 50, prior to disease onset). Ambulation and balance will also be assessed with open field and horizontal ladder analyses, respectively (14,15), and overall gait and balance will be assessed with a scoring system (Guyenet et al. (2010) *Journal of visualized experiments: JoVE* 21(39). PubMed PMID: 20495529. Pubmed Central PMCID: 3121238).

17. Description of Approach to Assess In Vivo Target Engagement a. Assessment of Compound Binding to P65 In Vitro.

Without wishing to be bound by theory, it is predicted that these novel compounds activate NF-kB-dependent transcription of SOD2 via binding directly to p65. To this end, it will be determined whether these compounds bind directly to p65 using biolayer inferometry. However, since it is not possible to evaluate compound binding to p65 in vivo, SOD2 expression and activity will be used as a proxy for target engagement.

Figures 8A, 8B:
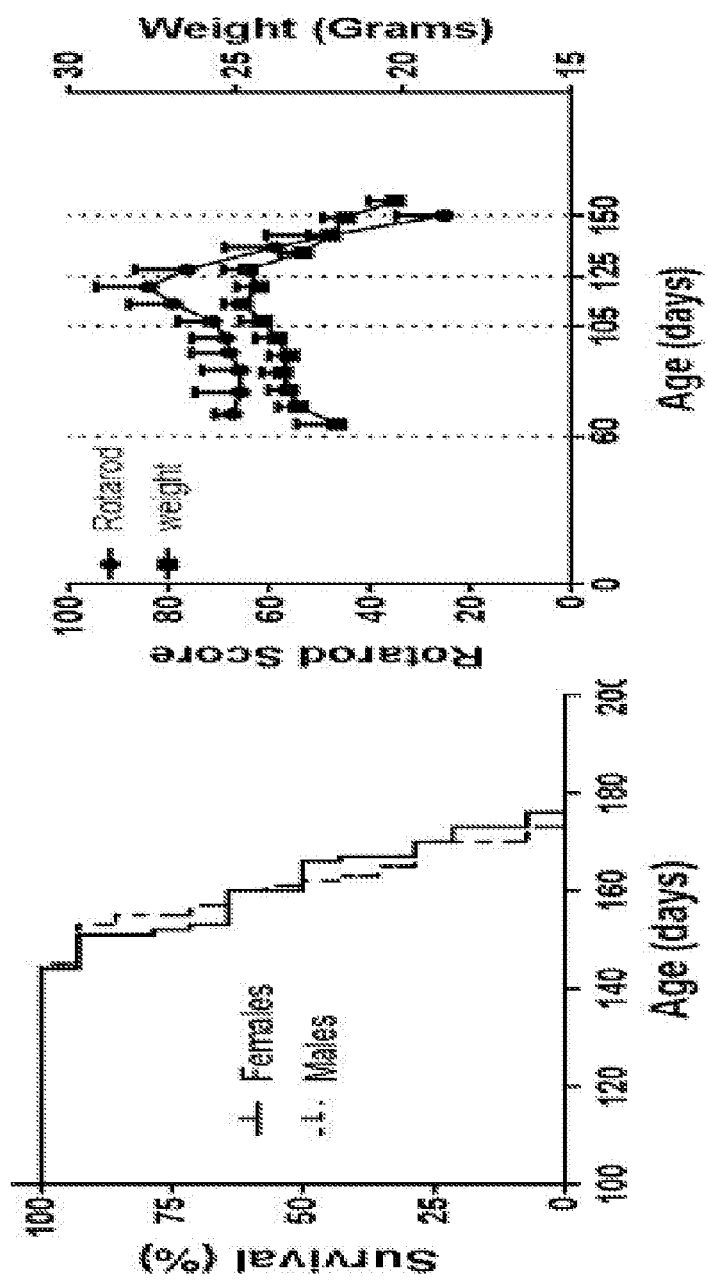
FIG. 8A-D show representative data demonstrating experience with the SOD1 G93A transgenic mouse model and identification of early markers for disease progression.
Figures 8C, 8D:
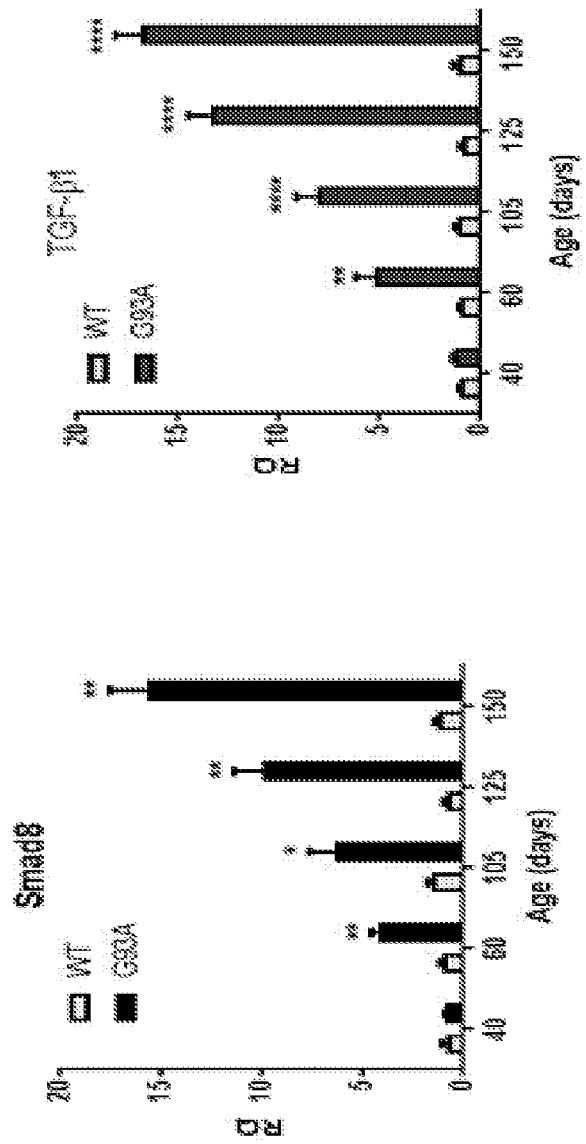
Figures 9A, 9B:
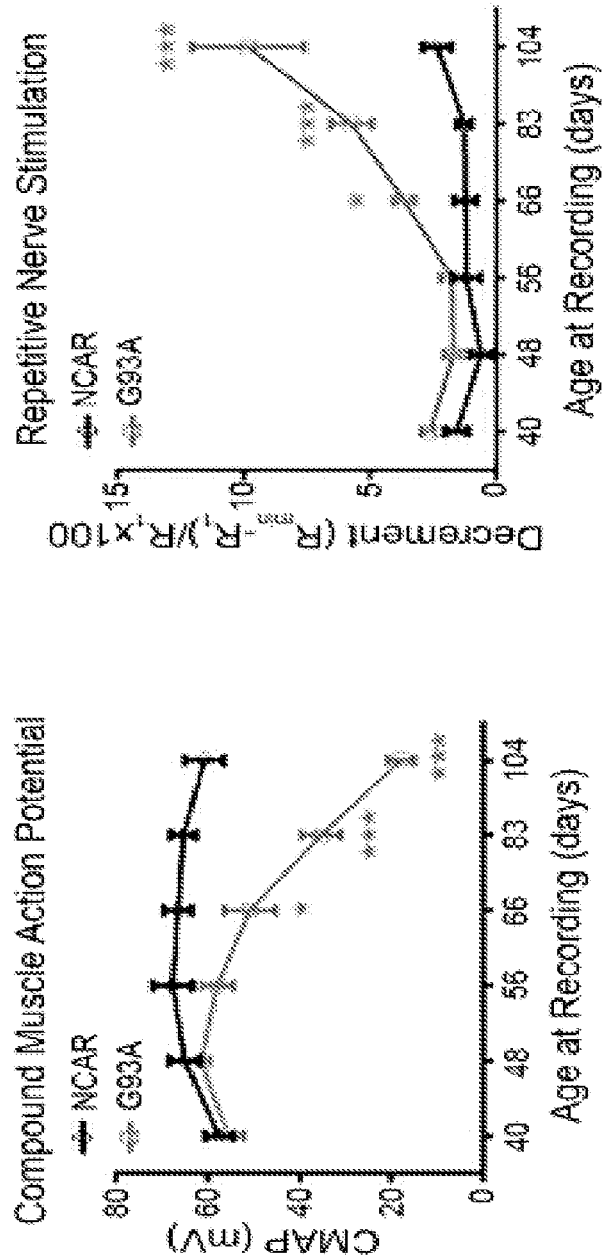
FIG. 9A and FIG. 9B show representative data demonstrating compound motor action potential amplitude and responses to nerve stimulation reveal nerve dysfunction in the SOD1 G93A transgenic mouse.

18. Description of Preclinical Animal Model to Assess In Vivo Efficacy a. Human SOD1 G93A Transgenic Mouse Model Based on the proposed mechanism of action of the novel compounds and the pilot data suggesting potential neuroprotection in mice expressing the human SOD1 G93A mutant transgene, the efficacy of novel compounds will be assessed in this mouse model. A variety of other factors have also informed this decision. This model is the most widely characterized mouse model for ALS (Nardo et al. (2016) *Brain pathology* 26(2):237-47; Philips and Rothstein (2015) Current protocols in pharmacology PubMed PMID: 26344214), with recent data (Si et al. (2014) *Annals of clinical and translational neurology* 1(10):778-87; Si et al. (2015) *PloS one* 10(9):e0138425) demonstrating progressive motor dysfunction and death in both males and females on the C57Bl/6 congenic background (JAX #004435; FIG. 8A and FIG. 8B) and novel readouts of early disease (FIG. 8C and FIG. 8D). Furthermore, it has been determined that the evaluation of compound muscle action potential (CMAP) is a good measure of early peripheral nerve dysfunction in the SOD1 G93A transgenic mouse line (Melanie Leitner PDSM, Ph.D.; Cathleen Lutz, Ph.D. Working with ALS Mice: Guidelines for preclinical testing & colony management. Cambridge, MA: Prize4Life; 2009) (FIG. 9A and FIG. 9B). Without wishing to be bound by theory, it is predicted that compounds which show efficacy in these models will be effective in other models involving motor neuron dysfunction and loss, such as the C9ORF72 mutant mouse line and iPSC models of ALS.

Referring to FIG. 8A-D, female and male SOD1 G93A mice on the C57BL/6 background show similar decline in survival (FIG. 8A), performance on the rotarod (test of motor function), and weight (FIG. 8B). As early as 80 days prior to death and 70 days prior to weight loss and motor impairment, SOD1 G93A mice show an increase in muscle expression of SMAD8 (FIG. 8C) and TGF-31 mRNA (FIG. 8D), markers of cellular stress (n=14 males, 14 females; *p<0.05, p<0.005, *p<0.0005, ****p<0.00005; 2-way ANOVA, post-hoc t-test).

Referring to FIG. 9A and FIG. 9B, male SOD1 G93A mice on the mixed SJL/C57BL/6 background show progressive decline in the amplitude of compound action potentials in the sciatic nerve and a loss of response to nerve stimulation with respect to age-matched littermate controls (NCAR). (n=12-14, two-way ANOVA (for genotype/time) with Sidak multicomparison test, *: p<0.05, ***: p<0.001.

b. SOD2 Expression and Activity as a Proxy and Biomarker for Target Engagement

SOD2 mRNA expression will be measured in brain and spinal cord tissue homogenates with q-RT-PCR and at a single-cell level with single-molecule fluorescence in situ hybridization (SM-FISH, FIG. 10), with a particular focus on motor neurons of the ventral spinal cord and layer V projection neurons of the motor cortex. Protein expression will be evaluated with Western blot and double-labeling fluorescence microscopy, and SOD activity will be measured in spinal cord and brain homogenates, with liver as a comparison tissue. Peripheral leukocytes will also be isolated from blood and SOD2 mRNA and protein expression will be measured, to determine whether these measures can be used as peripheral biomarkers of target engagement.

Figure 10:
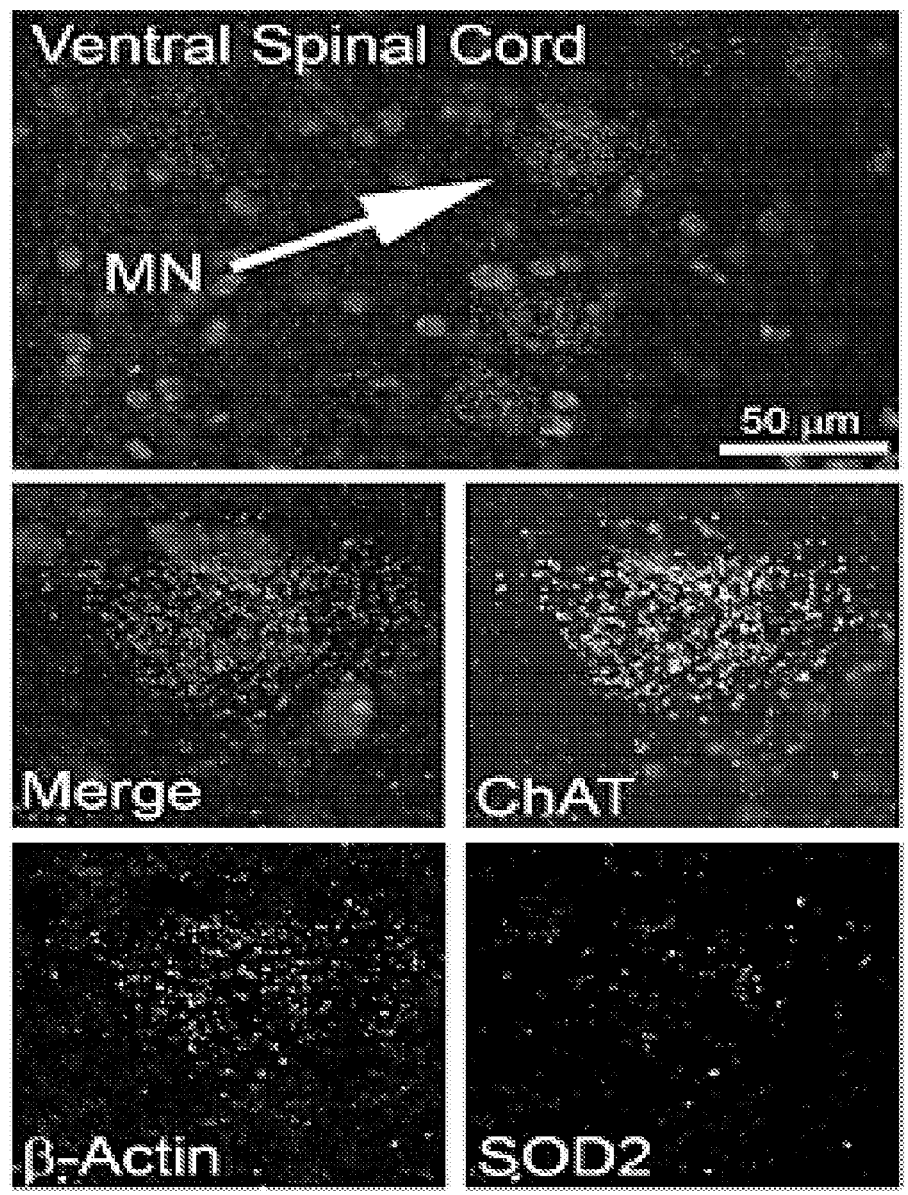
FIG. 10 shows representative data demonstrating single-molecule fluorescent in situ hybridization (SM-FISH) to localize and quantify SOD2 expression to motor neurons.

Referring to FIG. 10, SOD2 mRNA will be quantified selectively in motor neurons and other vulnerable neuronal populations (layer V cortical pyramidal neurons) using SM-FISH in mice treated with different compounds.

Figure 11:
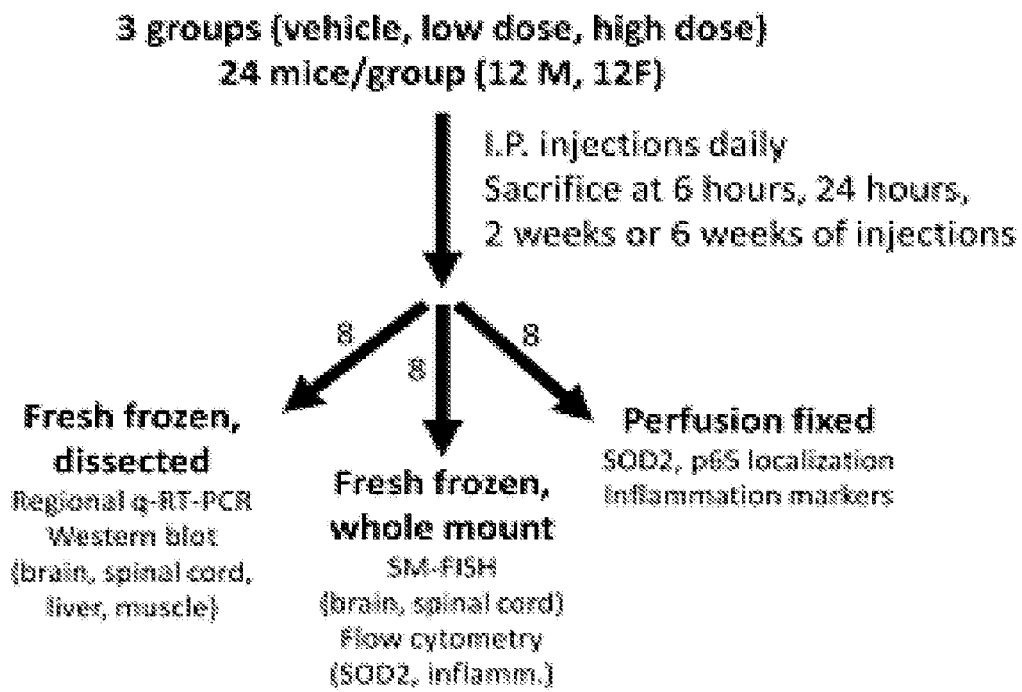
FIG. 11 shows a representative outline of an experimental plan for target engagement.

19. Testing of Target Engagement and Efficacy of Initial Novel Compounds in the SOD1 G93A Transgenic Mouse Line a. Target Engagement The ability of compound nos. 1 and 2 to increase SOD2 expression in mice (daily I.P. injections; 24/group: 12 M, 12 F; 4 time points: 6 hours, 24 hours, 2 weeks, 6 weeks; FIG. 11) will be tested. Drug-induced SOD2 expression will be evaluated in tissue homogenates (q-RT-PCR, Western blotting, SOD activity; n=8/group) and in a cell-specific manner (single-molecule in situ hybridization, double-labeling immunofluorescence; n=8/group) in wildtype mice. Tissue levels of cytokines will be evaluated with q-RT-PCR and ELISA, and gene expression and inflammatory profile will be evaluated in circulating leukocytes to determine whether SOD2 expression can be a peripheral readout of target engagement (n=8/group). If cytokine expression is detected, leukocyte infiltration into the CNS will be evaluated using cell-specific markers for different leukocyte populations. Then, it will be determined whether this is associated with microglial and astrocyte activation (IBA-1 and GFAP immunostaining, respectively).

b. Breeding and Maintenance of the SOD1 G93A Transgenic Mouse Colony

Breeders will be purchased from JAX for trio breeding (one transgenic male per two wildtype females). Breeders will be replaced after 9-12 months (or sooner, depending on productivity). All offspring will be genotyped using a specific genotyping protocol from JAX that allows for the estimation of transgene copy number. See, e.g., Scott et al. (2008) *Amyotrophic lateral sclerosis: official publication of the World Federation of Neurology Research Group on Motor Neuron Diseases* 9(1):4-15 and Gurney et al. (1994) *Science* 264(5166):1772-5.

c. Determination of Progression of Symptoms in SOD1 G93A Colony

Figure 12:
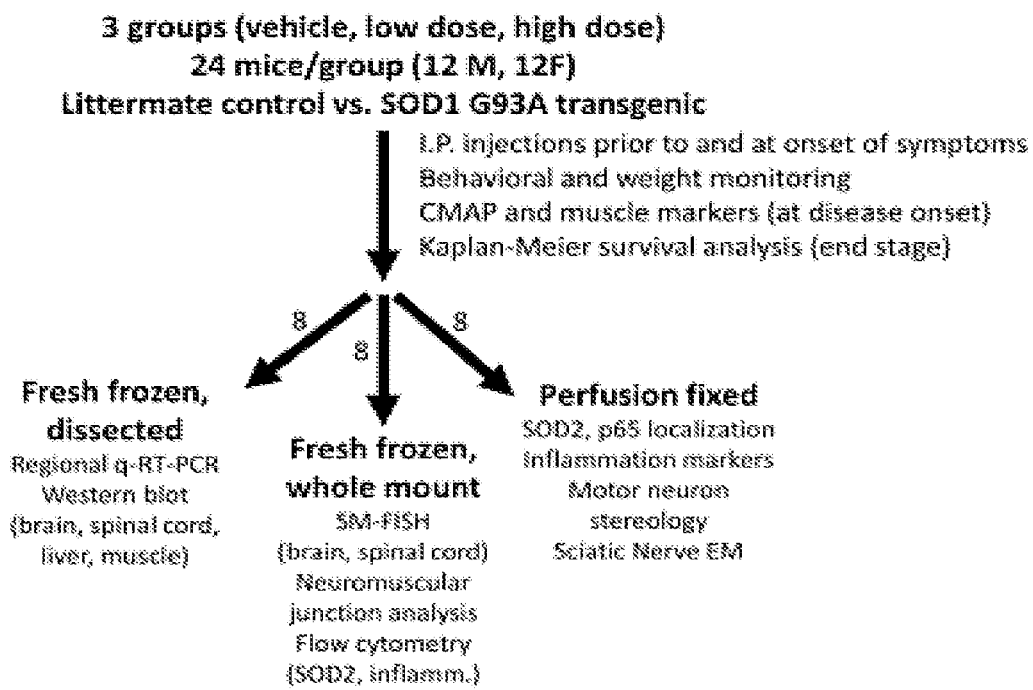
FIG. 12 shows a representative outline of an experimental plan for efficacy in the SOD1 G93A mouse model.

The treatment paradigm that is most likely to be translatable to humans is one that is initiated after the initial onset of measurable symptoms but not too late for intervention. While previous studies have shown changes in muscle biomarkers (SMAD8 and TGF-1β) and reduction in CMAP amplitude between 60 and 70 days of age (C57BL/6 background), this finding will initially be confirmed in one cohort of SOD1 G93A mice (12 M, 12 F; transgenic vs. wildtype littermates). Gross motor behavior assessments will be performed using previously published methods (Guyenet et al. (2010) *Journal of visualized experiments: JoVE* 21(39)). Balance and gait will be evaluated three times per week starting at day 50, with CMAP evaluation to be performed once motor impairment is distinguishable from age-matched littermate controls. The goal for this experiment is to identify two time points for treatment initiation: prior to onset of symptoms and at the time of symptom emergence.

d. Functional Engagement/Efficacy with Drug Treatment Prior to, or at the Time of, Symptom Onset The compound that shows the higher induction of SOD2 expression in the absence of inflammation will be chosen for testing in the SOD1 G93A transgenic mouse line (FIG. 12). Treatment will be initiated before or at the emergence of symptoms (between P60 and P80, as determined by the initial test cohort), with daily I.P. injection (vehicle, 20, or 40 mg/kg compound). Litermate controls or SOD1 G93A transgenic mice (24/group, 12 M, 12 F) will be treated with vehicle, low dose, or high dose compound for behavioral (rotarod) and survival analysis (Kaplan-Meier curve). A second cohort will be treated similarly but sacrificed when the control mice are in the third stage (score of 3="rigid paralysis or minimal joint movement, foot not being used for generating forward motion" from "Working with ALS mice" (Melanie Leitner PDSM, Ph.D.; Cathleen Lutz, Ph.D. Working with ALS Mice: Guidelines for preclinical testing & colony management. Cambridge, MA: Prize4Life; 2009); for CMAP analysis, regional and cell-specific gene expression analyses (SOD2 in brain and spinal cord, SMAD/TGF-β in muscle), neuromuscular junction analysis, sciatic nerve electron microscopy, flow cytometry, and stereology.

Figure 13:
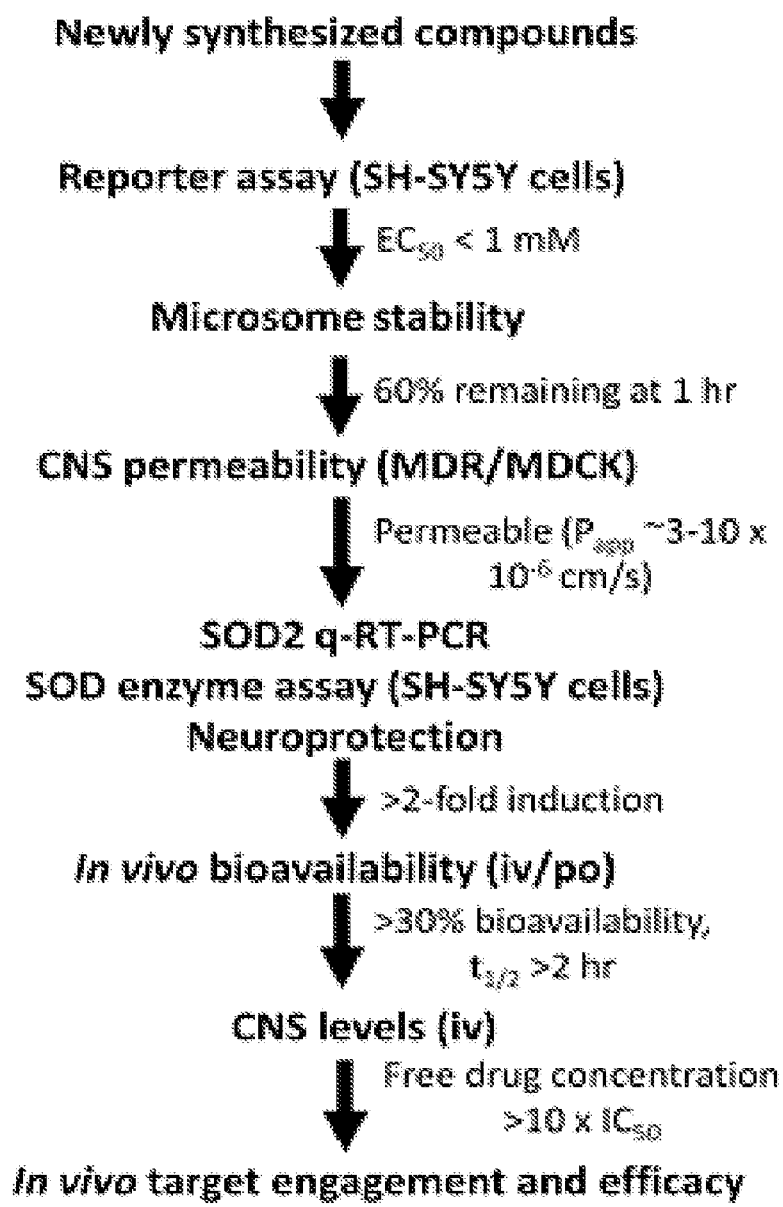
FIG. 13 shows a representative pipeline for the synthesis, testing, and selection of novel compounds.

20. Identification of Novel Compounds that Increase SOD2 Expression In Vitro and In Vivo and Test Whether the Lead Compound can Prevent and/or Slow the Progression of Disease in the SOD1 G93A Transgenic Mouse Line a. Identification of Novel Compounds Based on the New Series (Compound No. 40) and Test their Activity in the NF-κB High Throughput Screen Assay In FIG. 13, a compound progression that will be used to prioritize compounds and drive the program is outlined. The key attributes of the lead compounds will be novelty and demonstrated structure-activity relationships and potency ($EC_{50}$<100 nM) versus the primary NF-κB assay. The lead compounds will be optimized via targeted chemical modifications aimed at improving both activity and drug-like properties.

Figure 14:
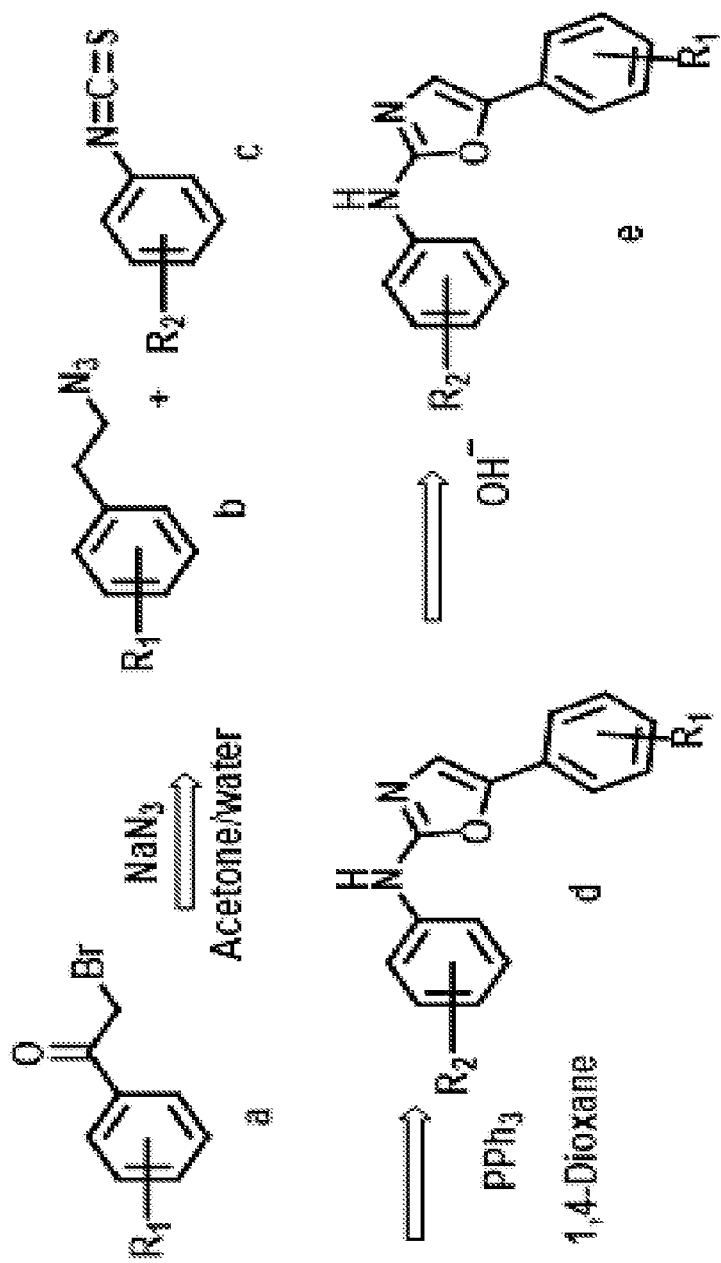
FIG. 14 shows a representative synthesis of oxazole compounds.
Figure 15:
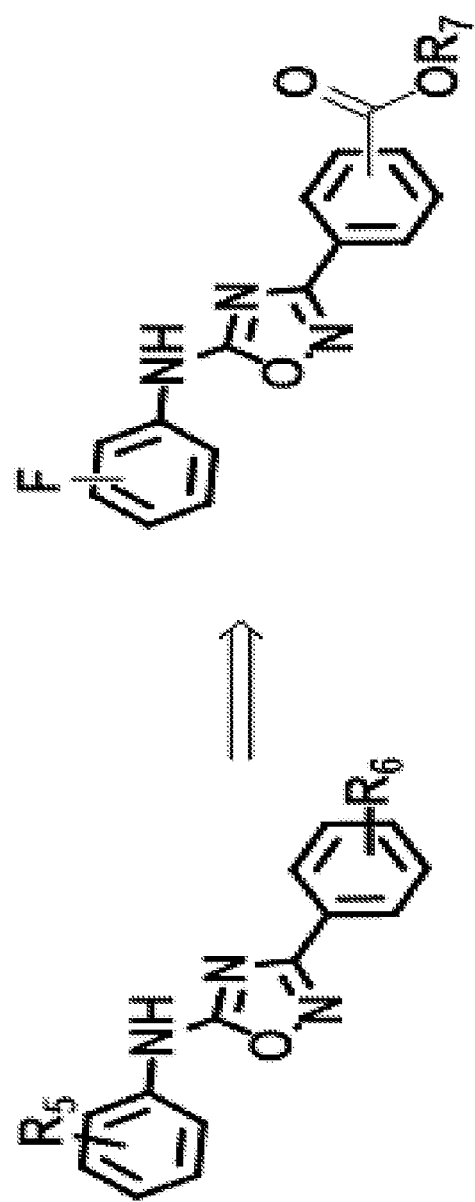
FIG. 15 shows a representative generation of 2-fluoro oxazoles.

The synthesis of oxazole compounds will proceed as shown (FIG. 14) (Bursavich et al. (2010) *Bioorganic & medicinal chemistry letters* 20(5):1677-9). Preliminary studies will be conducted on the oxadiazole series of compounds to determine if they have any advantages. A small set of derivatives will be made consisting of fluorine and carboxylic acid substitutions (FIG. 15; F=H, $CH_3$). The synthesis of the key intermediates and procedures required for the preparation of the oxadiazoles can be adapted from a literature report (Trstenjak et al. (2013) *European journal of medicinal chemistry* 64:302-13; Hammam and Youssif (1985) *Egyptian Journal of Chemistry* 27:515-23).

All newly synthesized compounds will be fully characterized using standard spectroscopic and chromatographic tools (HPLC, LC/MS, NMR, MS, and elemental analysis, as appropriate). Final products will be >98% pure, with no single impurity >0.5%.

b. Determine Permeability in MDR/MDCK Cells, SOD2 Expression and Activity, and Neuroprotective Efficacy In Vitro Appropriate physical chemical properties (solubility and chemical stability), cell permeability, plasma protein binding and CYP inhibition (3A4, 2D6, 2C9) will be determined for key compounds. Then, the likelihood that compounds will cross the blood brain barrier will be predicted using MDCK (Madin Darby Canine Kidney) cells transfected with the mdr1 gene (for the multi-drug resistant transporter Pgp). Subsequent experiments will investigate whether the compounds can induce SOD2 expression at the mRNA and protein levels in human SH-SY5Y, mouse NSC-34, and mouse primary cortical cultures. The compounds that induce SOD2 expression will be tested for their ability to protect neurons from hydrogen-peroxide or glutamate-induced cell death (Cowell et al. (2009) *Biochemical and biophysical research communications* 379(2):578-82) and whether these compounds prevent the depolarization of mitochondria associated with an increase in production of ROS (see methods). In cell cultures, the location of p65 will also be evaluated, as previous studies indicate that some of the drugs may influence gene expression by increasing p65 translocation (Writing and Edaravone (2017) *The Lancet Neurology* 16(7):505-12). At this point, a separate set of studies will use q-RT-PCR to test whether the neuroprotective compounds induce pro-inflammatory genes in THP-1 monocyte-derived cells or in primary astrocyte cultures.

c. Determine Bioavailability and CNS Levels of Top Compounds

Compounds which meet the established in vitro activity parameters will be examined for oral bioavailability and CNS permeability [fraction absorbed (% F)≥25%, $t_{1/2}$>2 h](9) prior to advancing for in vivo testing in a mouse model. Plasma and drug concentration will be determined over the period of 24 hours by mass spectroscopy.

d. Target Engagement with Two Novel Compounds

Initially, the ability of two novel compounds chosen above to increase SOD2 expression in mice will be tested (24/group: 12 M, 12 F; 4 time points: 6 hours, 24 hours, 2 weeks, 6 weeks). Compounds will be delivered via oral gavage daily. Drug-induced SOD2 expression will be evaluated in tissue homogenates (q-RT-PCR, Western blotting; n=8/group) and in a cell-specific manner (single-molecule in situ hybridization, double-labeling immunofluorescence; n=8/group) in wildtype mice. Tissue levels of cytokines will be evaluated with q-RT-PCR and ELISA, and gene expression and inflammatory profile will be evaluated in circulating leukocytes to determine whether SOD2 expression can be a peripheral readout of target engagement (n=8/group).

e. Functional Engagement/Efficacy with Treatment Prior or at the Onset of Symptoms in the SOD1 G93A Mouse Line The compound that shows the higher induction of SOD2 expression in the absence of inflammation will be chosen for testing in the SOD1 G93A transgenic mouse line. Treatment will be initiated prior to or after the emergence of symptoms. The formulation used for these studies will be the same as those used for the bioavailability studies. For example, prior to initiating those studies a suitable formulation is determined. Examples include 5% DMSO/30% PEG 400/65% water for I.V. and 5% DMSO/30% PEG 400/65% water for P.O. Littermate controls or SOD1 G93A transgenic mice (24/group, 12 M, 12 F) will be treated with vehicle, low dose, or high dose compound for behavioral (rotarod) and survival analysis (Kaplan-Meier curve). A second cohort will be treated similarly but sacrificed when the control mice are in the third stage (20) for CMAP analysis, regional and cell-specific gene expression analyses, neuromuscular junction analysis, sciatic nerve electron microscopy, flow cytometry, and stereology.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

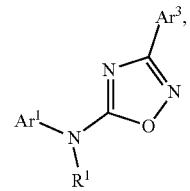

wherein $R^1$ is selected from hydrogen and C1-C4 alkyl;

wherein $Ar^1$ is selected from monocyclic aryl and pyridinyl, and is substituted with 0, 1, 2, or 3 groups independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino;

wherein $Ar^3$ is pyridinyl substituted with 0, 1, 2, or 3 $R^4$ groups; and wherein each occurrence of $R^4$ is independently selected from halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino, or a pharmaceutically acceptable salt thereof.

2. The compound of claim 1, wherein $Ar^1$ is monocyclic aryl substituted with 1, 2, or 3 —F groups.

3. The compound of claim 1, wherein the compound has a structure represented by a formula:

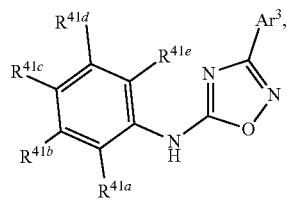

wherein each of $R^{41a}$, $R^{41b}$, $R^{41c}$, $R^{41d}$, and $R^{41e}$ when present, is independently selected from hydrogen, halogen, —CN, —NH$_2$, —OH, C1-C4 alkyl, C1-C4 haloalkyl, C1-C4 hydroxyalkyl, C1-C4 alkoxy, C1-C4 alkylamino, and (C1-C4)(C1-C4) dialkylamino.

4. The compound of claim 1, wherein the compound is:

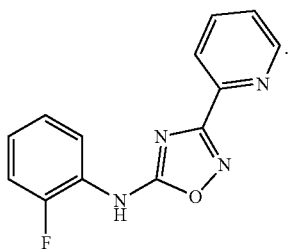 [SMILES: Fc1ccccc1Nc1nc(-c2ccccn2)no1]

5. A pharmaceutical composition comprising a therapeutically effective amount of at least one compound of claim 1 and a pharmaceutically acceptable carrier.

6. A method for the treatment of a disorder in a subject, the method comprising the step of administering to the subject an effective amount of the compound of claim 1 or a pharmaceutically acceptable salt thereof, wherein the disorder is a neurological disorder or a neuromuscular disorder.

7. The method of claim 6, wherein the subject has been diagnosed with a need for treatment of a neurological disorder prior to the administering step.

8. The method of claim 6, further comprising the step of identifying a subject in need of treatment of a neurological disorder.

9. The method of claim 6, wherein the effective amount is a therapeutically effective amount.

10. The method of claim 6, wherein the disorder is a neurological disorder.

11. The method of claim 10, wherein the neurological disorder is ALS.

12. The method of claim 6, wherein the disorder is a neuromuscular disorder.

13. The method of claim 12, wherein the neuromuscular disorder is Duchenne muscular dystrophy (DMD) or amyotrophic lateral sclerosis (ALS).

* * * * *